United States Patent
Altarac et al.

(10) Patent No.: US 11,076,892 B2
(45) Date of Patent: Aug. 3, 2021

(54) ANTERIOR CERVICAL PLATE

(71) Applicant: Neurostructures, Inc., Irvine, CA (US)

(72) Inventors: Moti Altarac, Irvine, CA (US); Joey Reglos, Irvine, CA (US)

(73) Assignee: NeuroStructures, Inc., Irvine, CA (US)

( * ) Notice: Subject to any disclaimer, the term of this patent is extended or adjusted under 35 U.S.C. 154(b) by 318 days.

(21) Appl. No.: 16/054,568

(22) Filed: Aug. 3, 2018

(65) Prior Publication Data

US 2020/0038068 A1    Feb. 6, 2020

(51) Int. Cl.
*A61B 17/70* (2006.01)
*A61B 17/80* (2006.01)
*A61F 2/30* (2006.01)

(52) U.S. Cl.
CPC ...... *A61B 17/7059* (2013.01); *A61B 17/8042* (2013.01); *A61B 17/8047* (2013.01); *A61B 17/8033* (2013.01); *A61F 2002/30476* (2013.01); *A61F 2002/30495* (2013.01); *A61F 2002/30514* (2013.01)

(58) Field of Classification Search
CPC ............ A61B 17/7059; A61B 17/8042; A61B 17/8047; A61B 17/7074; A61B 17/8033; A61B 17/8061; A61B 17/808; A61F 2002/30476; A61F 2002/30492; A61F 2002/30495; A61F 2002/30497; A61F 2002/30499; A61F 2002/30514; A61F 2002/30515; A61F 2002/30517
USPC ............... 606/279, 288, 289, 290, 295, 296
See application file for complete search history.

(56) References Cited

U.S. PATENT DOCUMENTS

| | | | |
|---|---|---|---|
| 3,741,205 A | 6/1973 | Markoff et al. | |
| 5,085,660 A | 2/1992 | Lin | |
| 5,364,399 A | 11/1994 | Lowery et al. | |
| 5,423,826 A | 6/1995 | Coates et al. | |
| 5,549,612 A | 8/1996 | Yapp et al. | |
| 5,616,142 A | 4/1997 | Yuan et al. | |
| 5,616,144 A | 4/1997 | Yapp et al. | |
| 5,725,588 A * | 3/1998 | Errico ................. | A61F 2/30721 623/22.36 |
| 6,045,552 A | 4/2000 | Zucherman et al. | |
| 6,139,550 A | 10/2000 | Michelson | |
| 6,398,783 B1 | 6/2002 | Michelson | |
| 6,527,776 B1 | 3/2003 | Michelson | |
| 6,599,290 B2 | 7/2003 | Bailey et al. | |
| 6,602,255 B1 | 8/2003 | Campbell et al. | |

(Continued)

FOREIGN PATENT DOCUMENTS

| | | |
|---|---|---|
| EP | 1520545 B1 | 11/2006 |
| EP | 1429675 B1 | 10/2007 |

(Continued)

*Primary Examiner* — Marcela I. Shirsat
(74) *Attorney, Agent, or Firm* — Rimas T. Lukas

(57) ABSTRACT

An anterior cervical plate system is provided. The plate is configured to receive bone screws for attachment to and immobilization of adjacent vertebrae of the spine. The system includes a cup retained inside a through hole of the plate by a cup retainer. A bone screw is retained inside the cup by a lock that is movable between a locked position and an unlocked position. The cup is permitted to angulate forward and backward with respect to the plate and the bone screw is permitted to angulate conically with respect to the cup to provide a plate system with extreme angulation for the bone screw.

20 Claims, 46 Drawing Sheets

(56) References Cited

U.S. PATENT DOCUMENTS

| | | |
|---|---|---|
| 6,626,907 B2 | 9/2003 | Campbell et al. |
| 6,652,525 B1 | 11/2003 | Assaker et al. |
| 6,695,846 B2 | 2/2004 | Richelsoph et al. |
| 6,926,718 B1 | 8/2005 | Michelson |
| 6,936,051 B2 | 8/2005 | Michelson |
| 6,964,664 B2 | 11/2005 | Fried et al. |
| 7,175,623 B2 | 2/2007 | Thramann et al. |
| 7,186,254 B2 | 3/2007 | Dinh et al. |
| 7,220,263 B2 | 5/2007 | Cordaro |
| 7,273,481 B2 | 9/2007 | Lombardo et al. |
| 7,276,070 B2 | 10/2007 | Muckter |
| 7,278,997 B1 | 10/2007 | Mueller et al. |
| 7,288,094 B2 | 10/2007 | Lindemann et al. |
| 7,288,095 B2 | 10/2007 | Baynham et al. |
| 7,291,152 B2 | 11/2007 | Abdou |
| 7,306,605 B2 | 12/2007 | Ross |
| 7,318,825 B2 | 1/2008 | Butler et al. |
| 7,524,325 B2 | 4/2009 | Khalili |
| 7,601,170 B2 | 10/2009 | Winslow et al. |
| 7,651,517 B2 | 1/2010 | Konieczynski et al. |
| 7,662,154 B2 | 2/2010 | Ribeiro |
| 7,686,806 B2 | 3/2010 | Rhyne |
| 7,704,255 B2 | 4/2010 | Michelson |
| 7,740,630 B2 | 6/2010 | Michelson |
| 7,803,157 B2 | 9/2010 | Michelson |
| 7,811,285 B2 | 10/2010 | Michelson |
| 7,815,666 B2 | 10/2010 | Baynham et al. |
| 7,824,432 B2 | 11/2010 | Michelson |
| 7,887,547 B2 | 2/2011 | Campbell et al. |
| 8,048,075 B2 | 11/2011 | Michelson |
| 8,206,293 B2 | 6/2012 | Reglos et al. |
| 8,439,924 B1 | 5/2013 | McBride et al. |
| 8,460,308 B2 | 6/2013 | Marino et al. |
| 8,652,182 B1 | 2/2014 | Walker et al. |
| 8,668,723 B2 | 3/2014 | Altarac et al. |
| 9,743,958 B2 | 8/2017 | Ishii et al. |
| 10,016,224 B2 | 7/2018 | Altarac et al. |
| 2002/0120270 A1 | 8/2002 | Trieu et al. |
| 2003/0060828 A1 | 3/2003 | Michelson |
| 2003/0093082 A1* | 5/2003 | Campbell .......... A61B 17/8875 606/104 |
| 2003/0105462 A1 | 6/2003 | Haider |
| 2003/0105466 A1 | 6/2003 | Ralph et al. |
| 2003/0105467 A1 | 6/2003 | Ralph et al. |
| 2003/0125739 A1 | 7/2003 | Bagga et al. |
| 2003/0135216 A1 | 7/2003 | Sevrain |
| 2003/0153920 A1 | 8/2003 | Ralph et al. |
| 2003/0171753 A1 | 9/2003 | Collins et al. |
| 2003/0181912 A1 | 9/2003 | Michelson |
| 2003/0187440 A1 | 10/2003 | Richelsoph et al. |
| 2003/0187442 A1 | 10/2003 | Richelsoph et al. |
| 2003/0187509 A1 | 10/2003 | Lemole, Jr. |
| 2003/0191471 A1 | 10/2003 | Michelson |
| 2003/0191472 A1 | 10/2003 | Michelson |
| 2003/0208204 A1 | 11/2003 | Bailey et al. |
| 2003/0229348 A1 | 12/2003 | Sevrain |
| 2003/0236528 A1 | 12/2003 | Thramann |
| 2004/0006343 A1 | 1/2004 | Sevrain |
| 2004/0015169 A1 | 1/2004 | Gause |
| 2004/0019353 A1 | 1/2004 | Freid et al. |
| 2004/0024081 A1 | 2/2004 | Trieu et al. |
| 2004/0030336 A1 | 2/2004 | Khanna |
| 2004/0034352 A1 | 2/2004 | Needham et al. |
| 2004/0039387 A1 | 2/2004 | Gause et al. |
| 2004/0049279 A1 | 3/2004 | Sevrain |
| 2004/0068319 A1 | 4/2004 | Cordaro |
| 2004/0087945 A1 | 5/2004 | Ralph et al. |
| 2004/0087951 A1 | 5/2004 | Khalili |
| 2004/0092929 A1 | 5/2004 | Zindrick |
| 2004/0092947 A1 | 5/2004 | Foley |
| 2004/0097925 A1 | 5/2004 | Boehm, Jr. et al. |
| 2004/0097934 A1 | 5/2004 | Farris et al. |
| 2004/0097935 A1 | 5/2004 | Richelsoph et al. |
| 2004/0097938 A1 | 5/2004 | Alleyne |
| 2004/0097950 A1 | 5/2004 | Foley et al. |
| 2004/0106924 A1 | 6/2004 | Ralph et al. |
| 2004/0122426 A1 | 6/2004 | Michelson |
| 2004/0127897 A1 | 7/2004 | Freid et al. |
| 2004/0127899 A1 | 7/2004 | Konieczynski et al. |
| 2004/0127900 A1 | 7/2004 | Konieczynski et al. |
| 2004/0133205 A1 | 7/2004 | Thramann et al. |
| 2004/0153088 A1 | 8/2004 | Ralph et al. |
| 2004/0158246 A1 | 8/2004 | Assaker et al. |
| 2004/0177847 A1 | 9/2004 | Foley et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204710 A1 | 10/2004 | Patel et al. |
| 2004/0204712 A1 | 10/2004 | Kolb et al. |
| 2004/0204713 A1 | 10/2004 | Abdou |
| 2004/0210314 A1 | 10/2004 | Michelson |
| 2004/0215192 A1 | 10/2004 | Justis et al. |
| 2004/0215195 A1 | 10/2004 | Shipp et al. |
| 2004/0220571 A1 | 11/2004 | Assaker et al. |
| 2004/0220572 A1 | 11/2004 | Michelson |
| 2004/0225290 A1 | 11/2004 | Ferree |
| 2004/0236333 A1 | 11/2004 | Lin |
| 2004/0236334 A1 | 11/2004 | Michelson |
| 2004/0236335 A1 | 11/2004 | Michelson |
| 2004/0243128 A1 | 12/2004 | Howland |
| 2004/0260306 A1 | 12/2004 | Fallin et al. |
| 2005/0015092 A1 | 1/2005 | Rathbun et al. |
| 2005/0015093 A1 | 1/2005 | Suh et al. |
| 2005/0027296 A1 | 2/2005 | Thramann et al. |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0038436 A1 | 2/2005 | Michelson |
| 2005/0043732 A1 | 2/2005 | Dalton |
| 2005/0059970 A1 | 3/2005 | Kolb |
| 2005/0059971 A1 | 3/2005 | Michelson |
| 2005/0075633 A1 | 4/2005 | Ross |
| 2005/0085816 A1 | 4/2005 | Michelson |
| 2005/0137597 A1 | 6/2005 | Butler et al. |
| 2005/0149021 A1 | 7/2005 | Tozzi |
| 2005/0149026 A1 | 7/2005 | Butler et al. |
| 2005/0149027 A1 | 7/2005 | Campbell et al. |
| 2005/0171551 A1 | 8/2005 | Sukovich et al. |
| 2005/0177160 A1 | 8/2005 | Baynham et al. |
| 2005/0177161 A1 | 8/2005 | Baynham et al. |
| 2005/0177163 A1 | 8/2005 | Abdou |
| 2005/0187552 A1 | 8/2005 | Michelson |
| 2005/0187553 A1 | 8/2005 | Grabowski et al. |
| 2005/0187554 A1 | 8/2005 | Michelson |
| 2005/0192576 A1 | 9/2005 | Michelson |
| 2005/0208095 A1 | 9/2005 | Hunter et al. |
| 2005/0209593 A1 | 9/2005 | Kolb |
| 2005/0216005 A1 | 9/2005 | Howland |
| 2005/0216009 A1 | 9/2005 | Michelson |
| 2005/0216010 A1 | 9/2005 | Michelson |
| 2005/0228386 A1 | 10/2005 | Ziolo et al. |
| 2005/0234455 A1 | 10/2005 | Binder et al. |
| 2005/0261690 A1 | 11/2005 | Binder et al. |
| 2005/0273105 A1 | 12/2005 | Konieczynski et al. |
| 2005/0277930 A1 | 12/2005 | Parsons |
| 2005/0277938 A1 | 12/2005 | Parsons |
| 2006/0009845 A1 | 1/2006 | Chin |
| 2006/0030852 A1 | 2/2006 | Sevrain |
| 2006/0079961 A1 | 4/2006 | Michelson |
| 2006/0082015 A1 | 4/2006 | Happonen et al. |
| 2006/0085001 A1 | 4/2006 | Michelson |
| 2006/0149251 A1 | 7/2006 | Ziolo et al. |
| 2006/0149256 A1 | 7/2006 | Wagner et al. |
| 2006/0155298 A1 | 7/2006 | Mueller et al. |
| 2006/0161157 A1 | 7/2006 | Mosca et al. |
| 2006/0167456 A1 | 7/2006 | Johnston et al. |
| 2006/0189997 A1 | 8/2006 | Guenther et al. |
| 2006/0200134 A1 | 9/2006 | Freid et al. |
| 2006/0200146 A1 | 9/2006 | Doubler et al. |
| 2006/0200147 A1 | 9/2006 | Ensign et al. |
| 2006/0229620 A1 | 10/2006 | Rothman et al. |
| 2006/0235405 A1 | 10/2006 | Hawkes |
| 2006/0241611 A1 | 10/2006 | Castro |
| 2006/0241616 A1 | 10/2006 | Konieczynski et al. |

(56) References Cited

U.S. PATENT DOCUMENTS

| | | |
|---|---|---|
| 2006/0276792 A1 | 12/2006 | Ensign et al. |
| 2006/0287653 A1 | 12/2006 | Rhyne |
| 2007/0083203 A1 | 4/2007 | Ribeiro |
| 2007/0123884 A1 | 5/2007 | Abdou |
| 2007/0167954 A1 | 7/2007 | Sicvol et al. |
| 2007/0185489 A1 | 8/2007 | Abdou |
| 2007/0203492 A1 | 8/2007 | Needham et al. |
| 2007/0213728 A1 | 9/2007 | Lindemann et al. |
| 2007/0213729 A1 | 9/2007 | Lindemann et al. |
| 2007/0213820 A1 | 9/2007 | Magerl et al. |
| 2007/0213828 A1 | 9/2007 | Trieu et al. |
| 2007/0225707 A1 | 9/2007 | Wisnewski et al. |
| 2007/0225717 A1 | 9/2007 | Hawkes |
| 2007/0225718 A1 | 9/2007 | Ensign |
| 2007/0233070 A1 | 10/2007 | Young |
| 2007/0233072 A1 | 10/2007 | Dickinson et al. |
| 2007/0233107 A1 | 10/2007 | Zielinski |
| 2007/0233108 A1 | 10/2007 | Stalcup et al. |
| 2007/0233110 A1 | 10/2007 | Muhanna et al. |
| 2007/0233117 A1 | 10/2007 | Butler et al. |
| 2007/0233118 A1 | 10/2007 | McLain |
| 2007/0233119 A1 | 10/2007 | Markworth |
| 2007/0233120 A1 | 10/2007 | Thramann et al. |
| 2007/0239158 A1 | 10/2007 | Trieu et al. |
| 2007/0270851 A1 | 11/2007 | Erickson et al. |
| 2007/0270965 A1 | 11/2007 | Ferguson |
| 2007/0276371 A1 | 11/2007 | Baynham et al. |
| 2007/0276405 A1 | 11/2007 | Huebner et al. |
| 2008/0021470 A1 | 1/2008 | Ross |
| 2008/0051794 A1 | 2/2008 | Dec et al. |
| 2008/0208260 A1 | 8/2008 | Truckai et al. |
| 2008/0208262 A1 | 8/2008 | Butler et al. |
| 2008/0208263 A1 | 8/2008 | Butler et al. |
| 2008/0208341 A1 | 8/2008 | McCormack et al. |
| 2008/0215097 A1 | 9/2008 | Ensign et al. |
| 2008/0228226 A1 | 9/2008 | Shamie |
| 2008/0228230 A1 | 9/2008 | Ferree |
| 2008/0234680 A1 | 9/2008 | Zaiser et al. |
| 2008/0234681 A1 | 9/2008 | Baynham |
| 2008/0234689 A1 | 9/2008 | Melkent et al. |
| 2008/0234748 A1 | 9/2008 | Wallenstein et al. |
| 2008/0234749 A1 | 9/2008 | Forstein |
| 2008/0234750 A1 | 9/2008 | Woods et al. |
| 2008/0234751 A1 | 9/2008 | McClintock |
| 2008/0234752 A1 | 9/2008 | Dahners |
| 2008/0234753 A1 | 9/2008 | Trieu |
| 2008/0234755 A1 | 9/2008 | Henderson et al. |
| 2008/0269806 A1 | 10/2008 | Zhang et al. |
| 2008/0287999 A1 | 11/2008 | Markworth |
| 2008/0288001 A1 | 11/2008 | Cawley et al. |
| 2009/0131988 A1 | 5/2009 | Bush, Jr. et al. |
| 2009/0149888 A1 | 6/2009 | Abdelgany |
| 2009/0171397 A1 | 7/2009 | Rothman et al. |
| 2009/0177237 A1 | 7/2009 | Zucherman et al. |
| 2009/0177239 A1 | 7/2009 | Castro |
| 2009/0182341 A1 | 7/2009 | Link et al. |
| 2009/0182383 A1 | 7/2009 | Prybyla et al. |
| 2009/0187218 A1 | 7/2009 | Schaffhausen |
| 2009/0192549 A1* | 7/2009 | Sanders ............ A61B 17/8605 606/280 |
| 2009/0210008 A1 | 8/2009 | Butler et al. |
| 2009/0222049 A1 | 9/2009 | Frigg et al. |
| 2009/0259226 A1 | 10/2009 | Michelson |
| 2009/0270926 A1 | 10/2009 | Hawkes |
| 2010/0016901 A1 | 1/2010 | Robinson |
| 2010/0042159 A1 | 2/2010 | Butler |
| 2010/0049256 A1 | 2/2010 | Jeon et al. |
| 2010/0069968 A1 | 3/2010 | Assaker et al. |
| 2010/0234897 A1 | 9/2010 | Fisher et al. |
| 2010/0312279 A1 | 12/2010 | Gephart et al. |
| 2011/0054528 A1 | 3/2011 | Michelson |
| 2011/0106159 A1 | 5/2011 | Nazeck |
| 2011/0118784 A1 | 5/2011 | Baynham et al. |
| 2011/0190770 A1 | 8/2011 | Suh |
| 2011/0230885 A1 | 9/2011 | Weiner et al. |
| 2011/0313477 A1 | 12/2011 | McLean et al. |
| 2012/0109208 A1 | 5/2012 | Justis et al. |
| 2012/0245690 A1 | 9/2012 | Cowan, Jr. et al. |
| 2013/0023936 A1 | 1/2013 | Altarac et al. |
| 2013/0046345 A1 | 2/2013 | Jones et al. |
| 2013/0053895 A1* | 2/2013 | Stoll ................ A61B 17/809 606/279 |
| 2013/0060294 A1 | 3/2013 | Donahue |
| 2013/0245705 A1 | 9/2013 | McBride et al. |
| 2013/0261679 A1 | 10/2013 | McBride et al. |
| 2013/0331892 A1 | 12/2013 | Peterson et al. |
| 2014/0142632 A1 | 5/2014 | Keyer et al. |
| 2014/0148860 A1 | 5/2014 | Rinner |
| 2014/0277145 A1 | 9/2014 | Reiblat et al. |
| 2014/0277206 A1 | 9/2014 | Reitblat et al. |
| 2015/0039035 A1 | 2/2015 | Kruger |
| 2016/0022317 A1 | 1/2016 | Kraus |

FOREIGN PATENT DOCUMENTS

| | | |
|---|---|---|
| EP | 1841376 A2 | 10/2007 |
| EP | 1847229 A2 | 10/2007 |
| WO | WO2006076422 A2 | 7/2006 |
| WO | WO2007037774 A1 | 4/2007 |
| WO | WO2007101266 A1 | 9/2007 |
| WO | WO2007103081 A2 | 9/2007 |
| WO | WO2007121080 A2 | 10/2007 |
| WO | WO2006138291 B1 | 11/2007 |
| WO | WO2007134199 A2 | 11/2007 |
| WO | WO2009089395 A2 | 7/2009 |
| WO | WO2009091770 A1 | 7/2009 |
| WO | WO2009091775 A2 | 7/2009 |

* cited by examiner

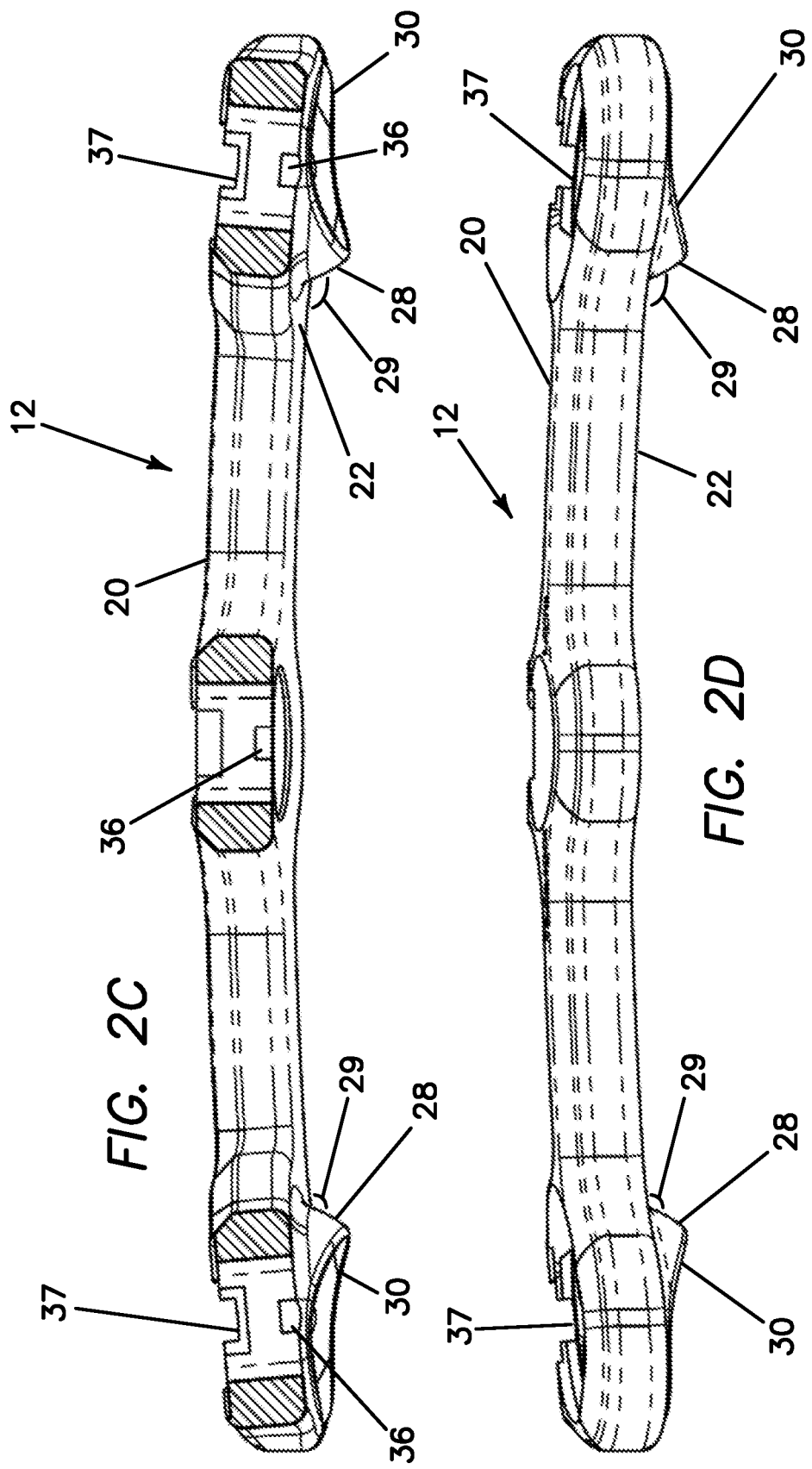

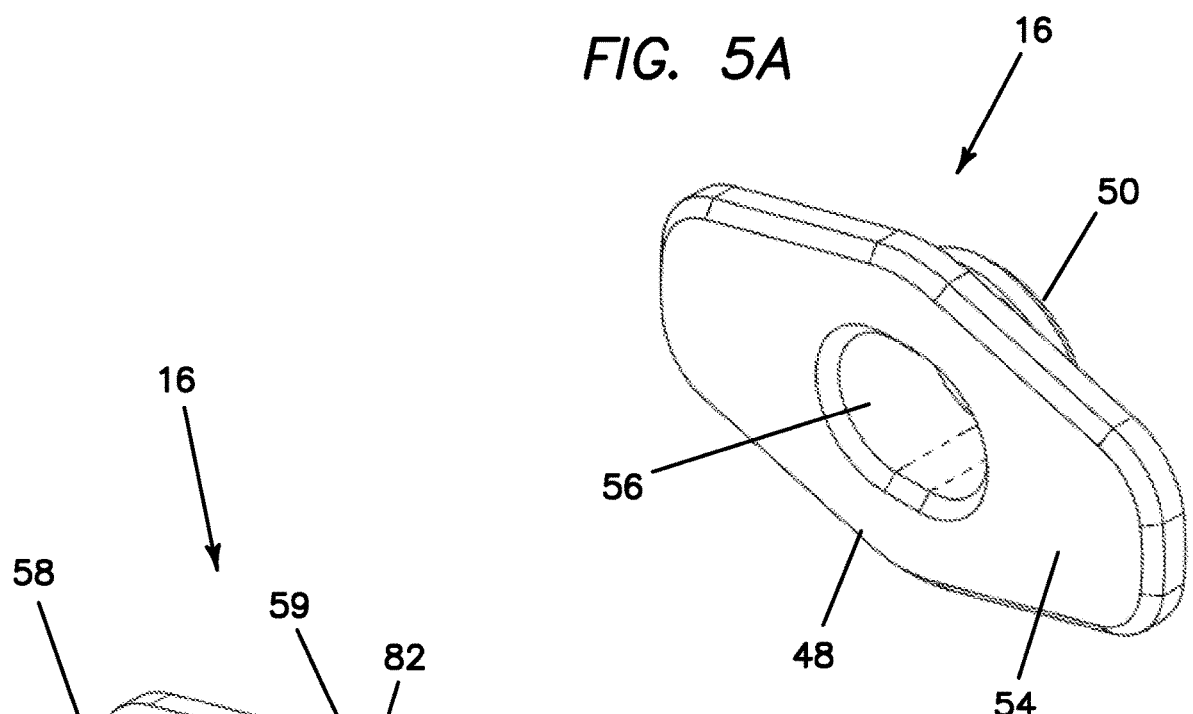
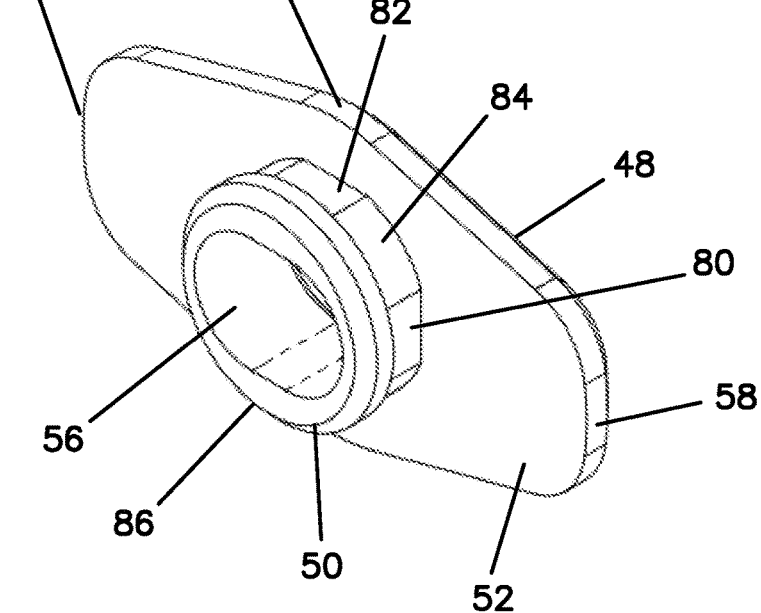

ANTERIOR CERVICAL PLATE

FIELD OF THE INVENTION

The present invention relates to medical devices, and in particular, to bone fixation plates used in spinal surgery.

BACKGROUND OF THE INVENTION

Anterior cervical plates are used for a variety of conditions to immobilize, stabilize or align cervical vertebrae. For example, after cervical spinal fusion surgery, cervical plates are used to add strength and rigidity to the adjoined vertebrae. Also, cervical plates secure vertebrae together where an intervening vertebra has been removed or replaced. In other cases, cervical plates are used to correct instability in the cervical spine caused by trauma, tumors, advanced degenerative discs, infection or congenital or acquired deformities.

A typical cervical plate includes an elongated rectangular plate that spans the distance between two or more vertebrae. The plate is curved to match the natural curvature of the spine at the location to which it is attached and bone screws are used to fasten the plate to the vertebral bodies. A pair of apertures is formed at one end of the plate for passing bone screws through and into a first vertebral body to secure the first end of the plate to the first vertebral body. A second pair of apertures is formed at the other end of the plate for passing bone screws through and into a second vertebral body to secure the second end of the plate to the second vertebral body. Thereby, the plate bridges two vertebral bodies. More vertebrae may be connected with a longer plate and a corresponding increased number of bone screw apertures and bone screws inserted therethrough at the intervening vertebral levels.

The cervical spine can be surgically approached anteriorly or posteriorly. In anterior cervical fusion surgery, an incision is made and the spine is approached from the front of the patient. The carotid sheath, muscles, trachea and esophagus are moved laterally to expose the cervical spine. Holes are drilled into the vertebral bodies or self-tapping screws are employed. The cervical plate is properly aligned on the vertebrae for the receipt of mounting screws and the plate is carefully and firmly attached. Sometimes fusion is accompanied by a discectomy in which a herniated disc is removed and a graft device is placed between the vertebral bodies to assist in fusion across levels. The plate may also include a window formed generally at a location between the two pairs of screw apertures through which bone growth progress may be observed. With the plate in position, the vertebrae are held by the plate in desired spatial relationships and orientations relative to each other, pressure is removed from the nerve roots and pain caused by the herniated disc or other condition is relieved.

Over time, the interface between the screws and the bone may present some problems of stability. Due to the anatomical structure of the cervical spine and the extreme anatomical forces that are brought to bear on the skeleton and transmitted to the cervical spine, the screws securing the plate to the spine may vibrate or toggle out of position. Also, the degeneration of vertebral bone quality may result in the screws loosening or becoming dislodged. As a result, bone screws securing the plate to the spine may move or back out of the vertebral body and plate. Due to the relative location to the esophagus and other connective tissue, if the bone screw securing the plate to the cervical spine backs out, the bone screw could impinge on the adjacent tissue and increase pain. Also, loosened screws may result instability of the joint and lead to increased pain for the patient.

Therefore, there is a need to provide a new and improved anterior cervical plate that resists fasteners, such as bone screws, from backing out of the plate and also from being loosened with respect to the plate before migrating out. Not only an improved and effective fastener retaining mechanism is required, but also, its design cannot add undue bulk to the plate. The anterior cervical plate must have a low profile due to the proximity of the implant site to the esophagus, nerves and other sensitive surrounding tissue. It is also preferable to keep the plate as narrow as possible to reduce the chances that the lateral edges rise off from the underlying vertebral body and cause pain where the curvature of the plate does not exactly match the patient's anatomy. Furthermore, there is a need for the anterior cervical plate to withstand anatomical forces and be easily implanted. Also, the screw retaining mechanism must be easily activated by the surgeon. It is further important that the bone screw have a wide range of angulation to provide optimum positioning. This invention, as described in the detailed description, sets forth an improved anterior cervical plate with anti-back out protection and a wide range of angulation for the bone screws that meets these needs.

SUMMARY OF THE INVENTION

According to another aspect of the invention, a bone plate system is provided. The bone plate system includes a plate having at least one through hole configured to receive a bone screw. The plate has an upper surface and a lower surface interconnected by side surfaces. The plate includes a lock aperture adjacent to the at least one through hole. Two oppositely disposed flat surfaces are formed inside the at least one through hole. The plate includes a groove formed at the at least one through hole. The plate system further includes a bone screw having a head portion connected to a shank portion. The bone screw is sized and configured for insertion into the through hole. The plate system further includes a lock retainer located inside the lock aperture and a lock having a main body connected to a lock post. The lock is connected to the plate by the lock retainer such that the lock is permitted to rotate with respect to the plate between an unlocked position in which the main body of the lock does not cover the head of the bone screw inside the through hole permitting passage of the bone screw in or out of the through hole and a locked position in which at least part of the main body is above the head portion of the bone screw to prevent the bone screw from backing out of the through hole. The plate system includes a cup located inside at least one through hole. The cup has an inner surface and an outer surface. The inner surface defines a lumen sized and configured to receive at least a portion of the bone screw. The outer surface of the cup includes two oppositely disposed flat surfaces. The plate system further includes a cup retainer located inside the groove. The cup retainer is sized and configured to retain the cup inside the at least one through hole. The cup is retained inside the at least one through hole such that the flat surfaces of the cup face the flat surfaces inside the through hole and the cup is movable with respect to the plate.

According to another aspect of the invention, a bone plate system is provided. The bone plate system includes a plate having at least one through hole configured to receive a bone screw. The plate has an upper surface and a lower surface interconnected by side surfaces and a longitudinal axis. The plate system includes a bone screw having a head portion connected to a shank portion. The plate system further includes a cup located inside at least one through hole. The cup has an inner surface and an outer surface. The inner surface of the cup defines a lumen sized and configured to receive at least a portion of the bone screw. The cup is connected to the plate such that the cup is retained and permitted to angulate with respect to the plate. The bone screw is connected to the plate such that the head portion of the bone screw is located inside the cup and the bone screw is permitted to angulate with respect to the cup.

According to another aspect of the invention, a bone plate system is provided. The plate system includes a plate having at least one through hole configured to receive a bone screw. The plate has an upper surface and a lower surface interconnected by side surfaces and a longitudinal axis. A groove is formed near the upper surface of the plate in the location of the at least one through hole. The bone screw includes a head portion connected to a shank portion. The plate system includes a cup located inside at least one through hole. The cup has an inner surface and an outer surface interconnected by a top surface and a bottom surface. The inner surface defines a lumen sized and configured to receive at least a portion of the bone screw. The cup has a shorter front relative to a longer back. The plate system includes a cup retainer located inside the groove. The cup retainer is sized and configured to retain the cup inside the at least one through hole such that the cup is permitted to angulate with respect to the plate. The cup retainer includes a scallop sized and configured to permit angulation/clearance of the back of the cup through the scallop. The bone screw is connected to plate such that the bone screw is permitted to angulate with respect to the cup.

BRIEF DESCRIPTION OF THE DRAWINGS

FIG. 2C is a cross-sectional view taken along line 2C-2C of FIG. 2B of a plate according to the present invention.

FIG. 2D is a side elevation view of a plate according to the present invention.

FIG. 5A is a top perspective view of a lock according to the present invention.

FIG. 5B is a bottom perspective view of a lock according to the present invention.

DETAILED DESCRIPTION OF THE INVENTION

Figure 1:
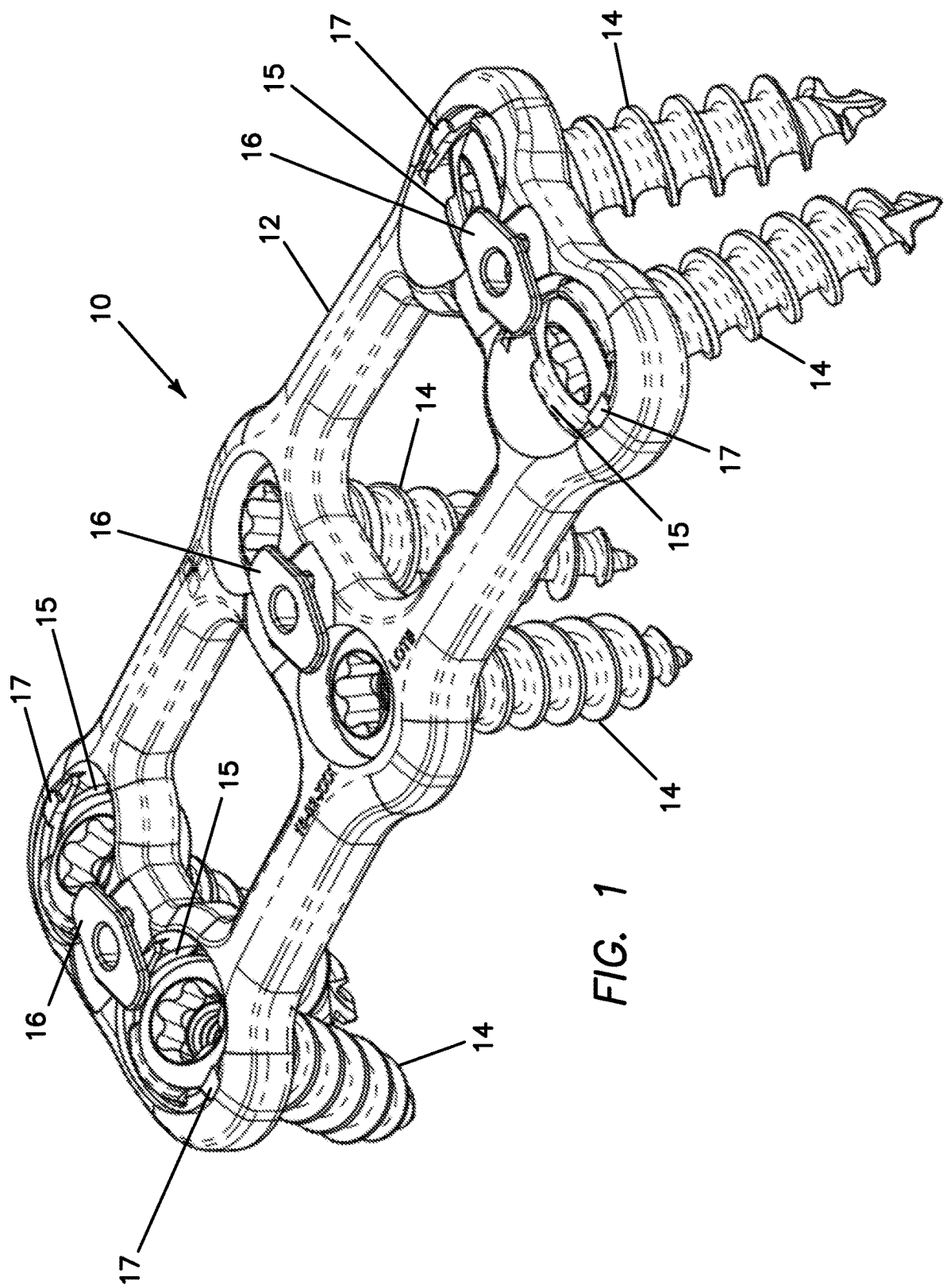
FIG. 1 is a top perspective view of an anterior cervical plate system in a locked position according to the present invention.

FIG. 1 depicts a cervical plate system 10 according to one variation of the invention that may be used to stabilize or fuse vertebral bodies in the cervical or other region of the spine. The anterior cervical plate system 10 that is shown in FIG. 1 is a two-level bone fixation plate that is configured to span across and fixate three vertebrae of the cervical spine; however, the invention is not so limited and the cervical plate system 10 may be a single level or any multilevel anterior cervical plate spanning two or more vertebral bodies and may be used to span any two bone pieces of the human anatomy. The anterior cervical plate system 10 comprises a plate 12 having fasteners 14. The fasteners 14 are prevented from backing out by a lock 16 rotatably connected to the plate 12 with a lock retainer 18 (not visible in FIG. 1). Each fastener 14 is connected to the plate 12 via a cup 15 which is connected with a cup retainer 17 to the plate 12.

Figure 2A:
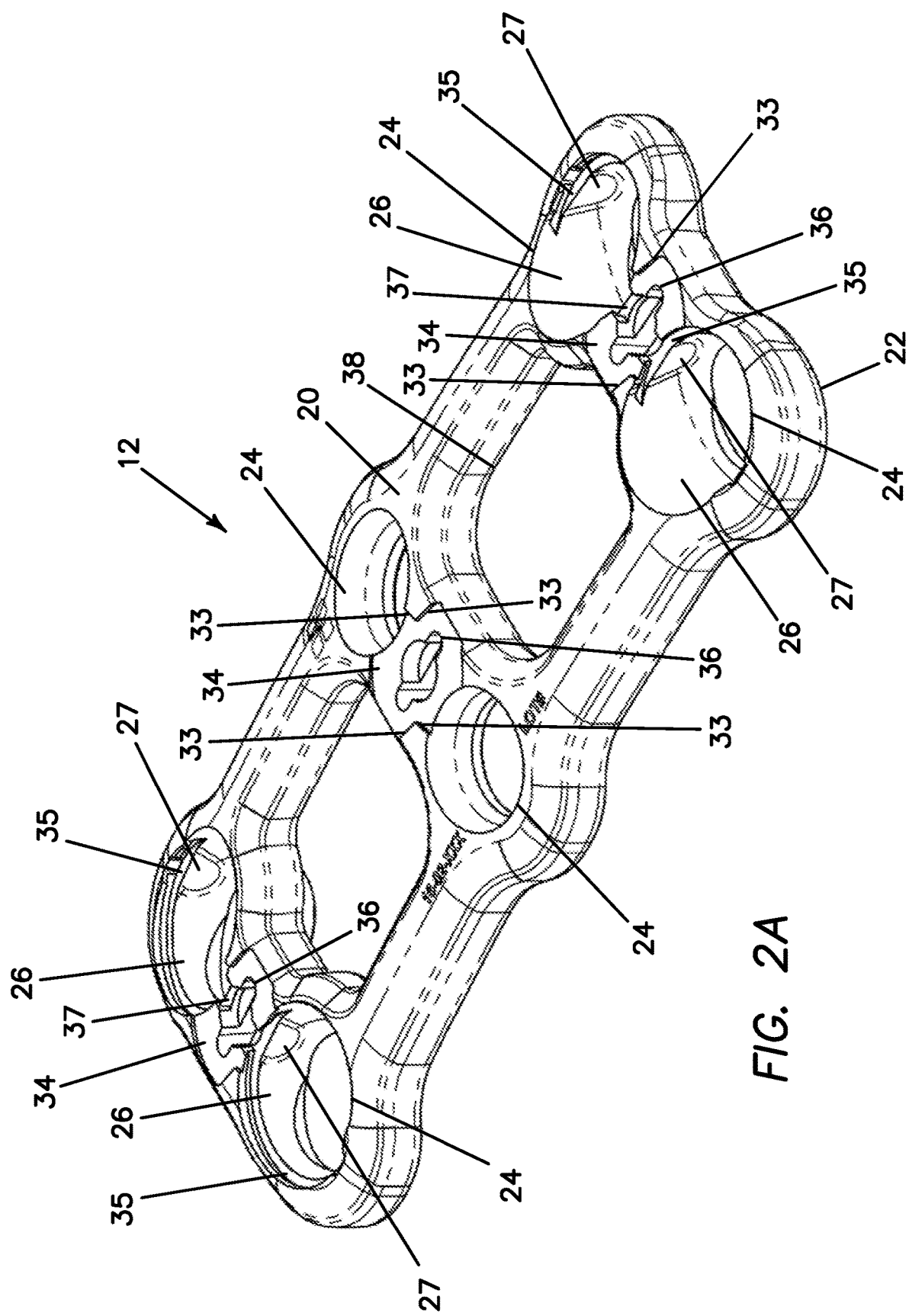
FIG. 2A is a top perspective view of a plate according to the present invention.
Figure 2B:
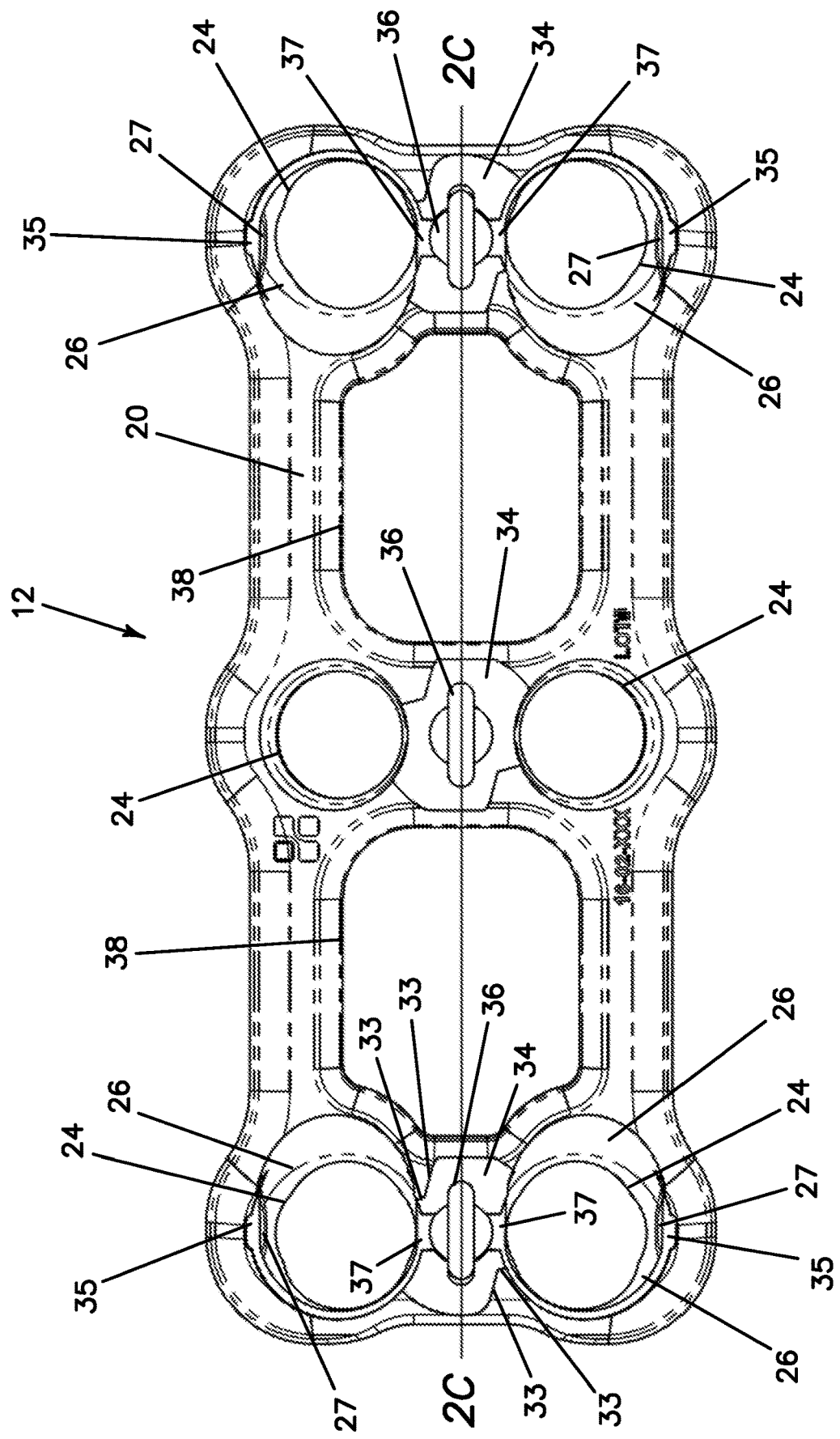
FIG. 2B is a top planar view of a plate according to the present invention.
Figure 2E:
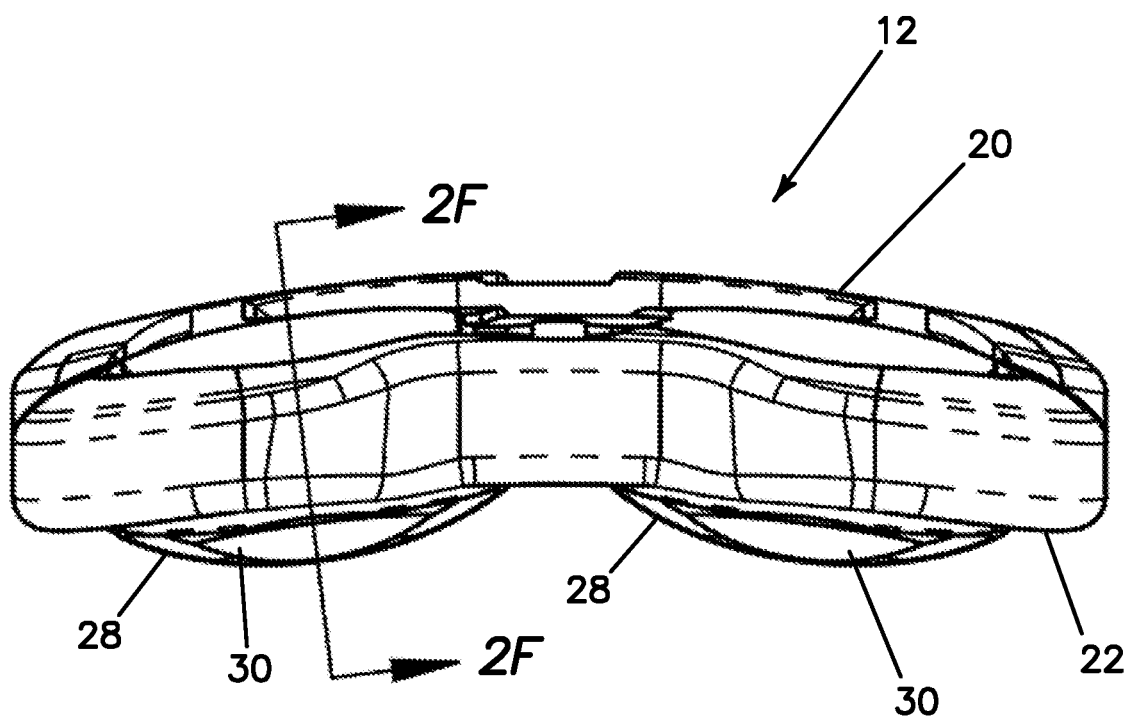
FIG. 2E is an end elevation view of a plate according to the present invention.

With reference to FIGS. 2A-2F, the plate 12 will now be described in greater detail. The plate 12 includes an upper surface 20 or anterior surface that faces the patient's soft tissue and esophagus when installed and a lower surface 22 or posterior surface facing the vertebral bodies to be immobilized. The upper surface 20 and lower surface 22 are interconnected by curved side walls and end walls to form a generally rectangular shape that is symmetrical about a longitudinal axis of the plate 12. As best seen in FIGS. 2C-2D, the gently curved structure of the rectangular plate 12 complements the natural curved structure of the vertebral bodies and lordotic curvature of the cervical spine. The corners of the plate 12 are rounded to reduce or eliminate irritation of the esophagus and the surrounding tissue. The plate 12 is sized and shaped for use on an anterior aspect of the cervical spine although one skilled in the art may use the device in other regions of the spine and other skeletal fixations. The plate 12, which resides atop the vertebral bodies, has a low profile as seen in FIG. 2C-2F so as to minimally impinge on adjacent tissues.

The plate 12 and other components of the cervical plate system 10 are made from suitable biocompatible material such as stainless steel, titanium and or any other metal or metal alloy. One or more components may be made of non-metal materials including but not limited to polymer, carbon reinforced polyetheretherketone (PEEK) or one or more biocompatible ceramics. The plate 12 may be additionally configured to promote bone ingrowth to the plate such as a portion of the plate being made of porous material or being roughened by mechanical blasting or plasma spraying with metal particles of one or more sizes. The plate 12 may also be coated with bio-active material, therapeutic agents for enhancing bone fusion and ingrowth, bone morphogenic proteins, growth factors and the like.

Figure 2F:
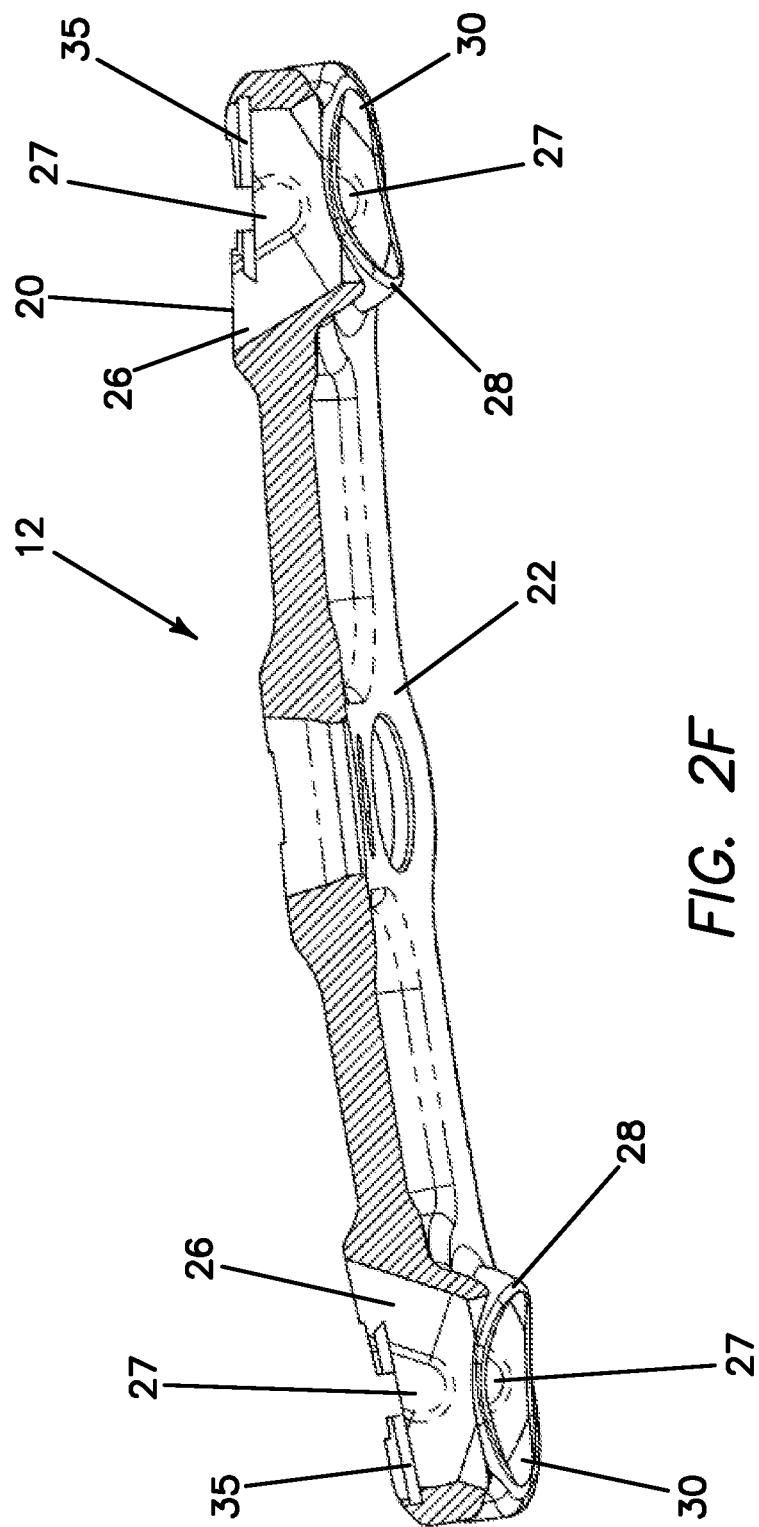
FIG. 2F is a cross-sectional view taken along line 2F-2F of FIG. 2E of a plate according to the present invention.
Figure 3A:
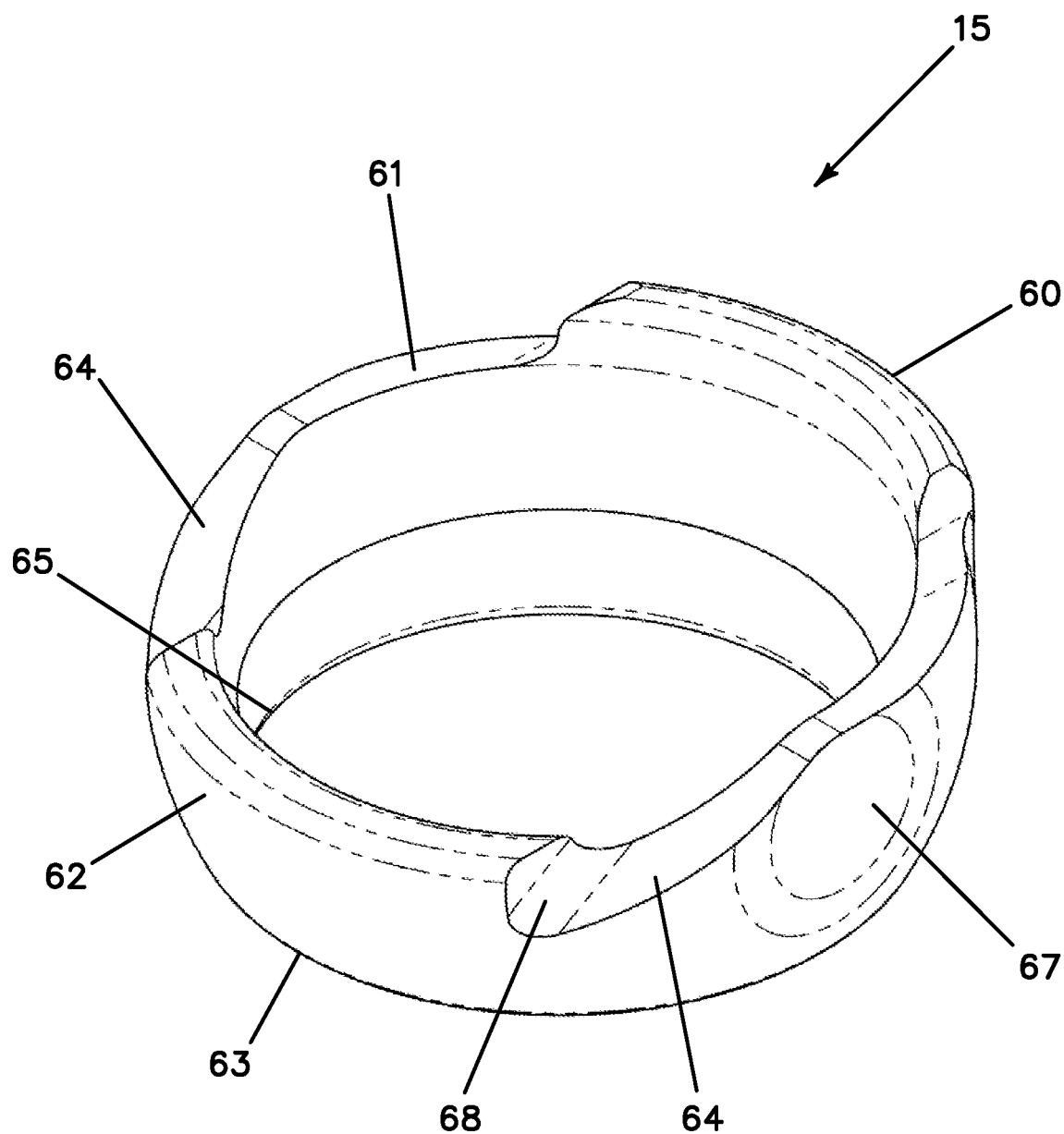
FIG. 3A is a top perspective view of a cup according to the present invention.
Figure 3B:
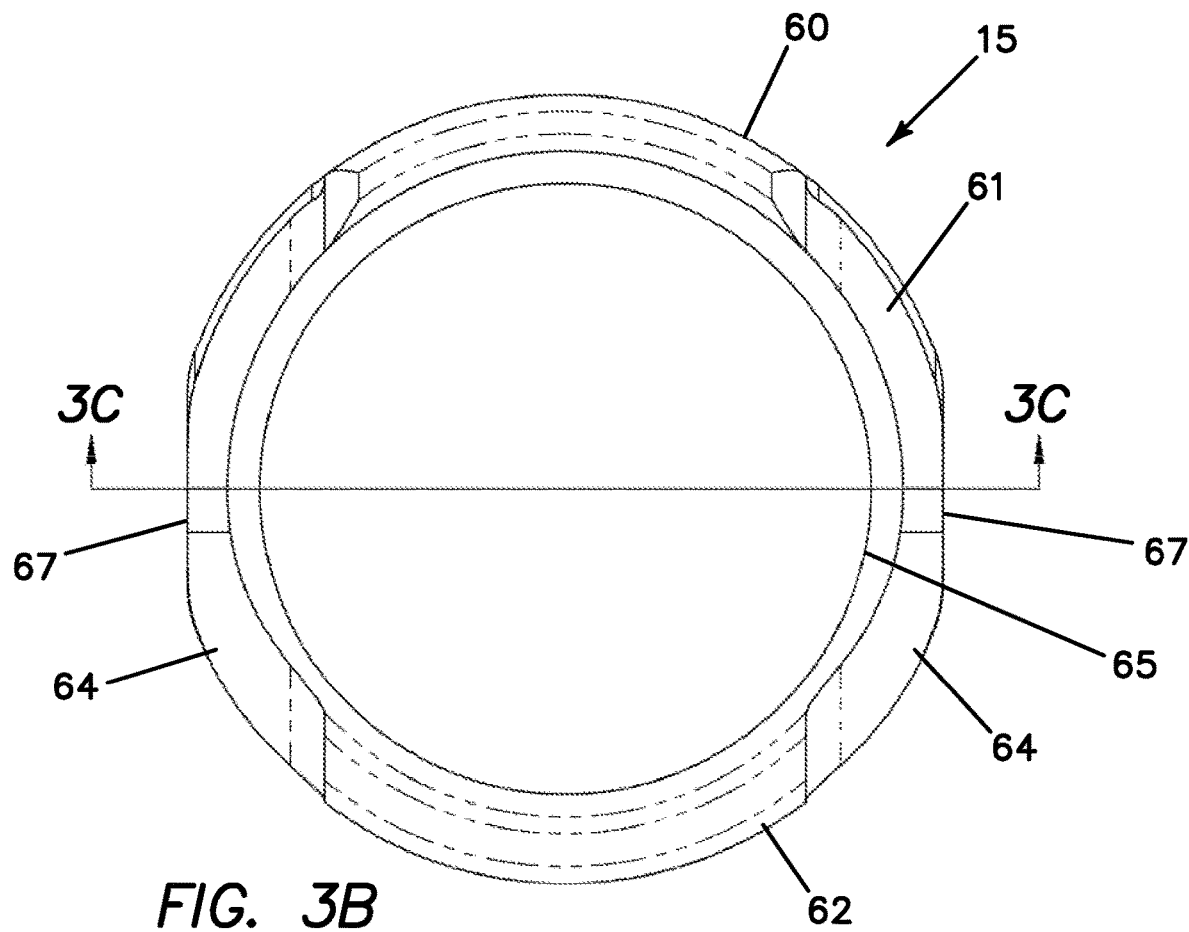
FIG. 3B is a top view of a cup according to the present invention.
Figure 3C:
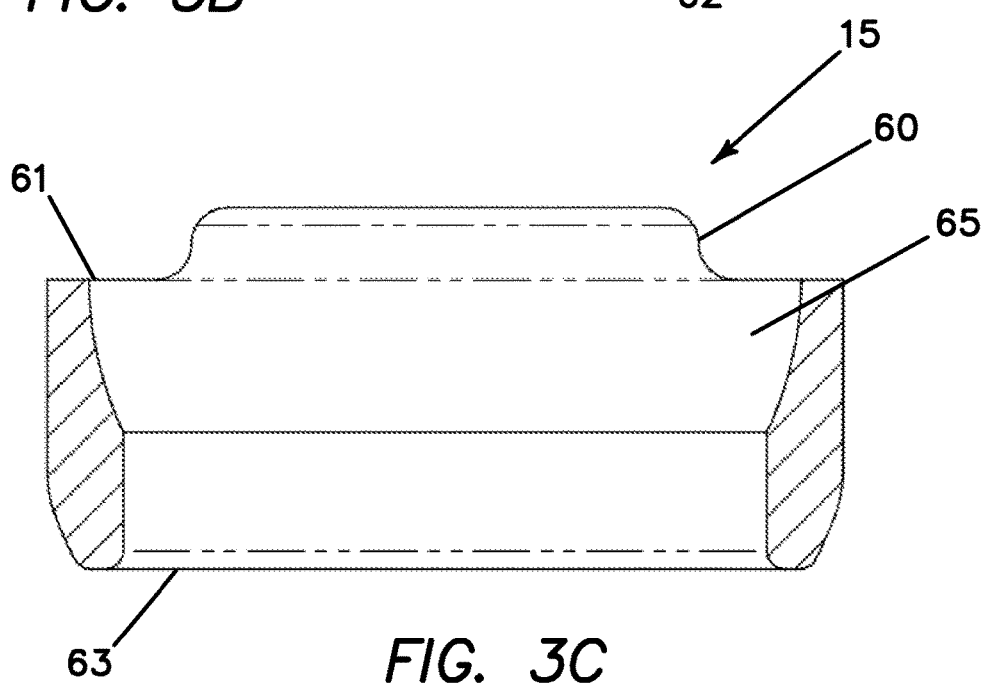
FIG. 3C is a cross-sectional view taken along line 3C-3C of FIG. 3B of a cup according to the present invention.
Figure 3D:
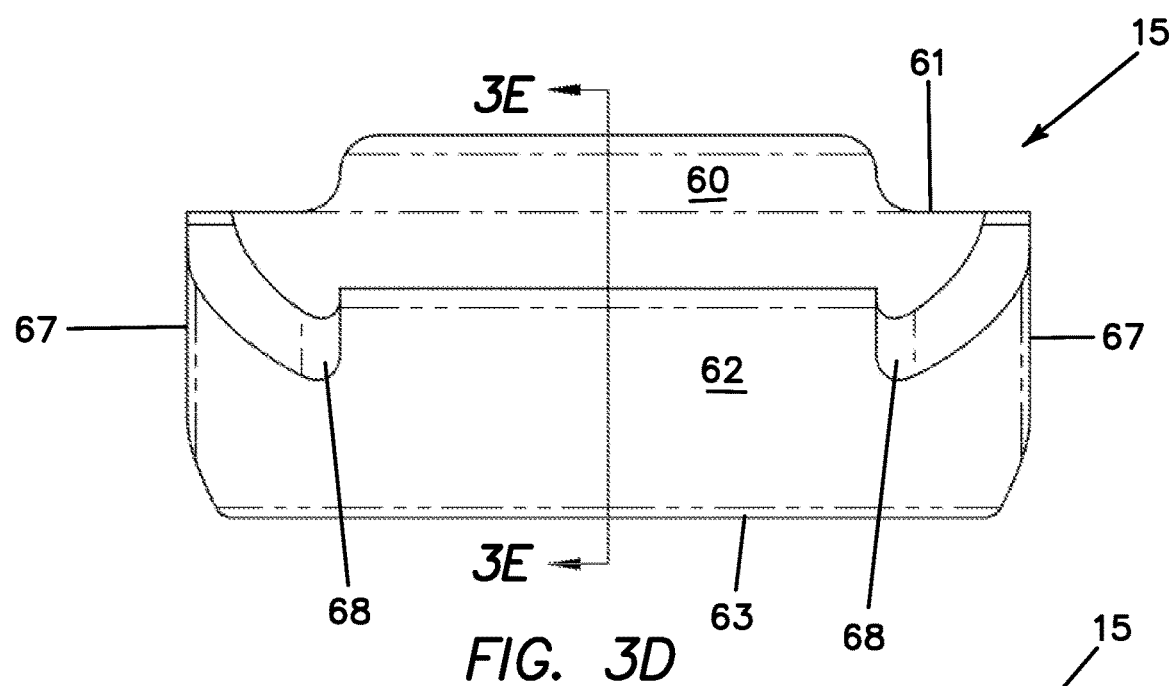
FIG. 3D is a front elevational view of a cup according to the present invention.
Figure 3E:
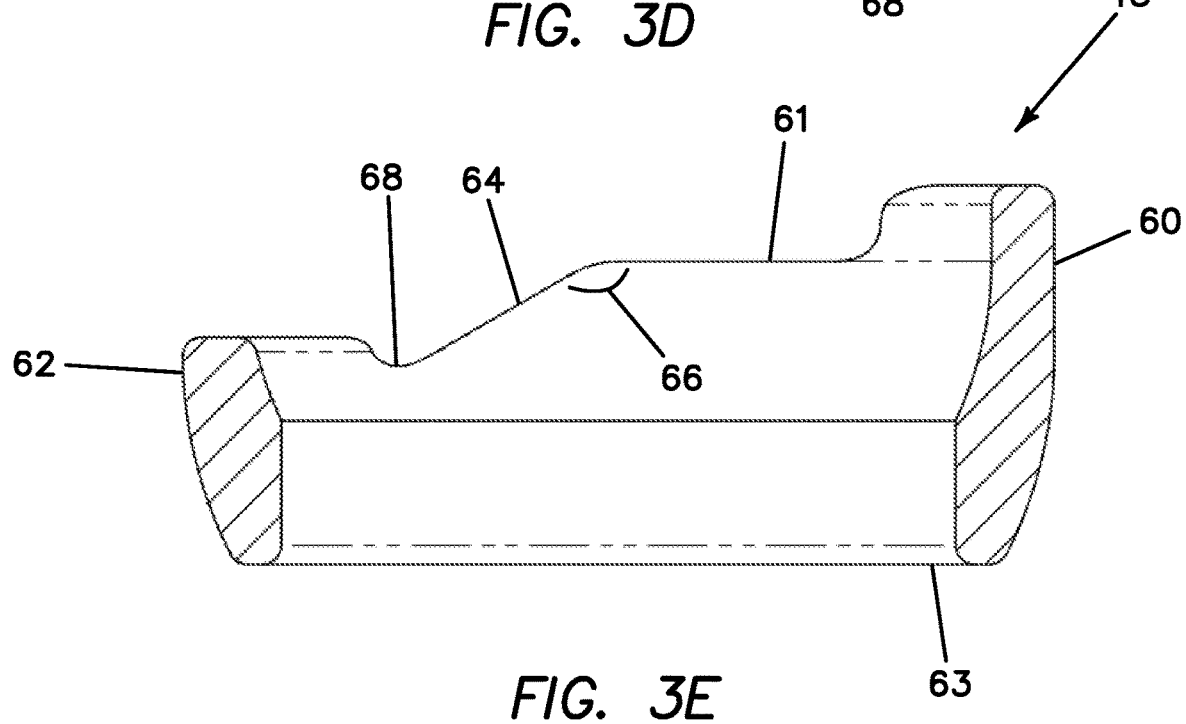
FIG. 3E is a cross-sectional view taken along line 3E-3E of FIG. 3D of a cup according to the present invention.
Figure 3F:
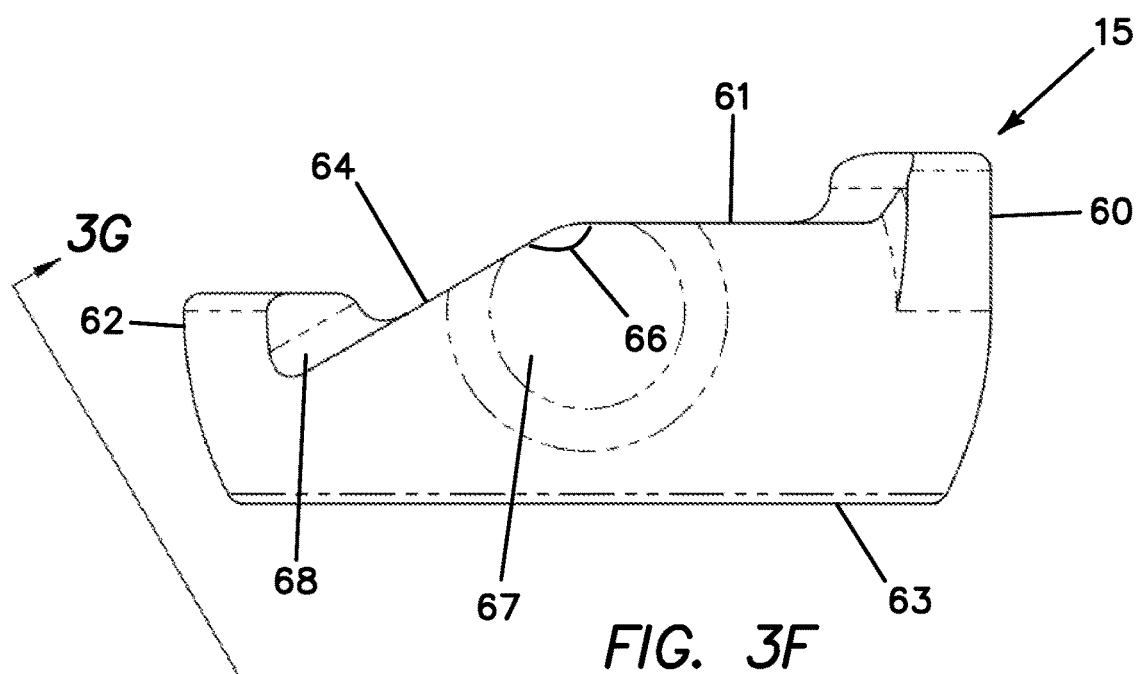
FIG. 3F is a side elevational view of a cup according to the present invention.
Figure 3G:
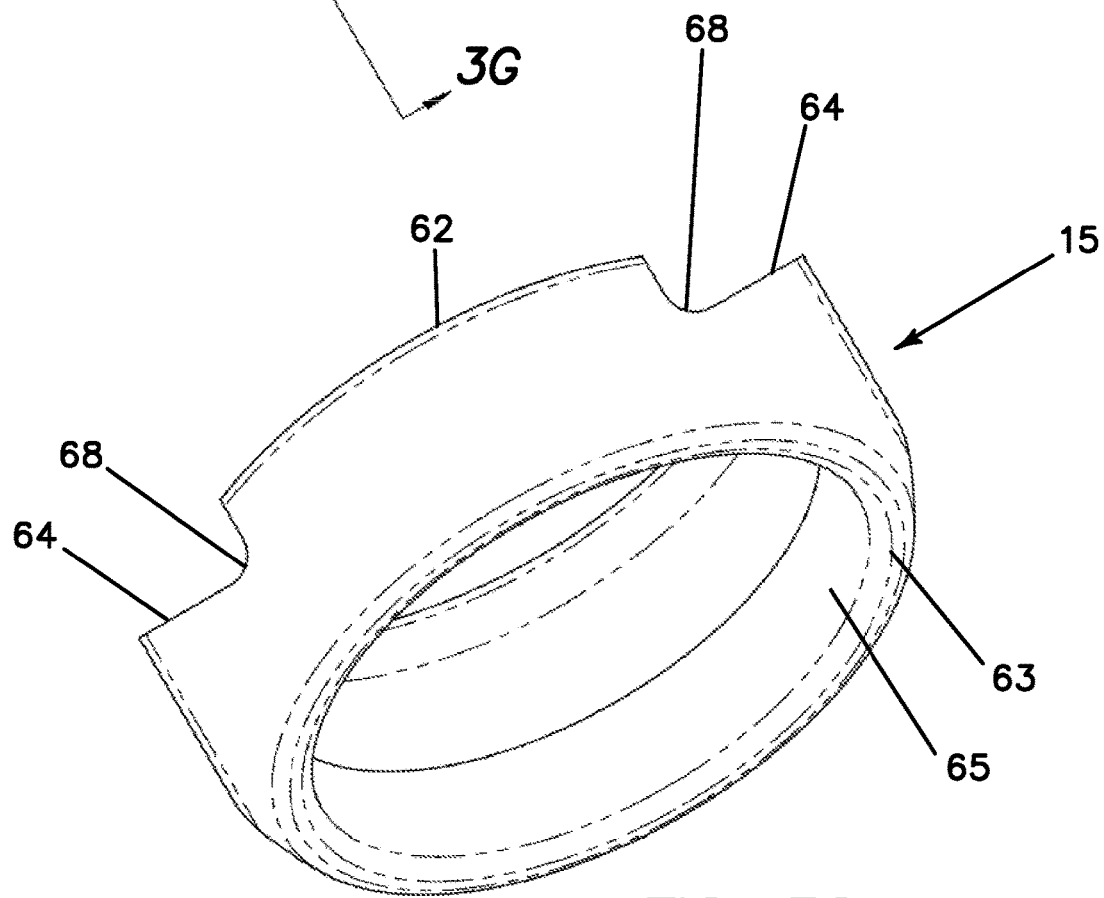
FIG. 3G is a cross-sectional view taken along line 3G-3G of FIG. 3F of a cup according to the present invention.
Figure 4A:
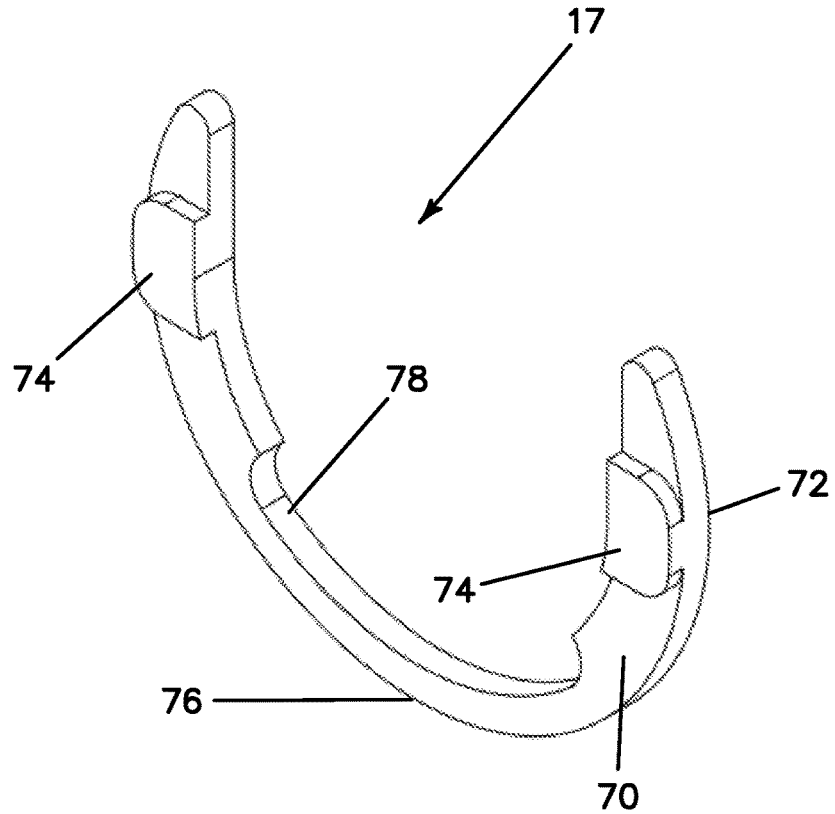
FIG. 4A is a top perspective view of a cup retainer according to the present invention.
Figure 4B:
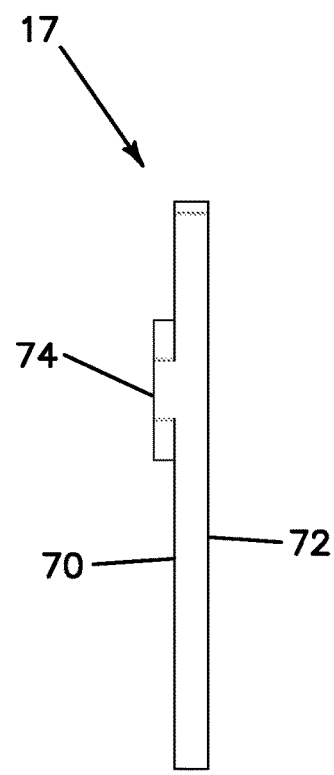
FIG. 4B is a side view of a cup retainer according to the present invention.
Figure 4C:
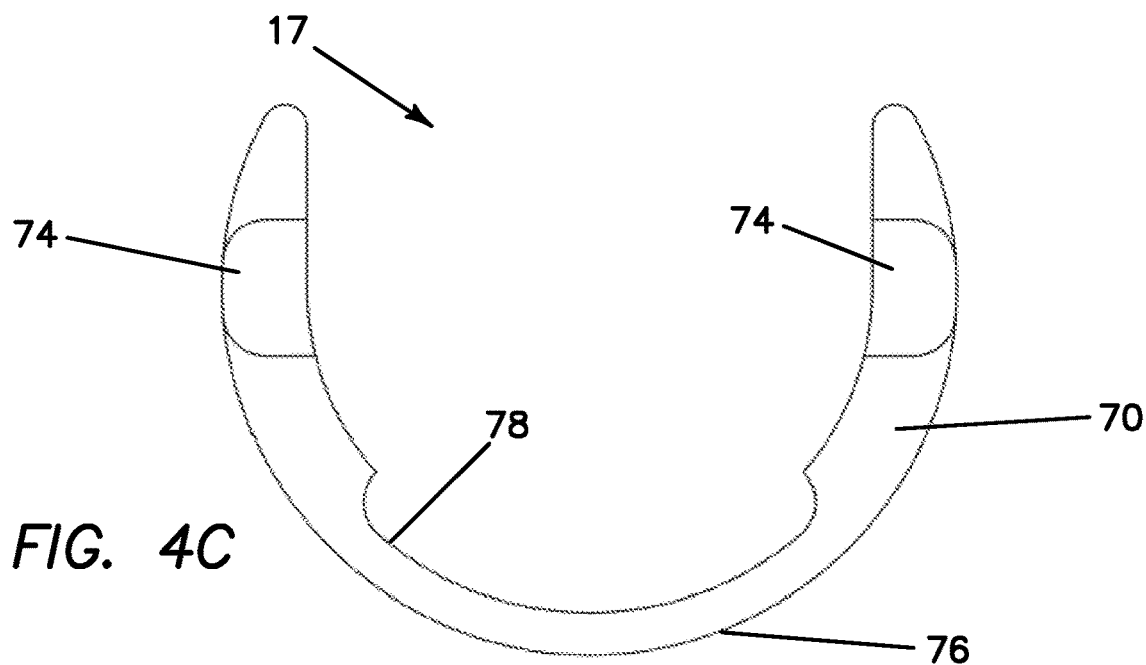
FIG. 4C is a top view of a cup retainer according to the present invention.
Figure 4D:
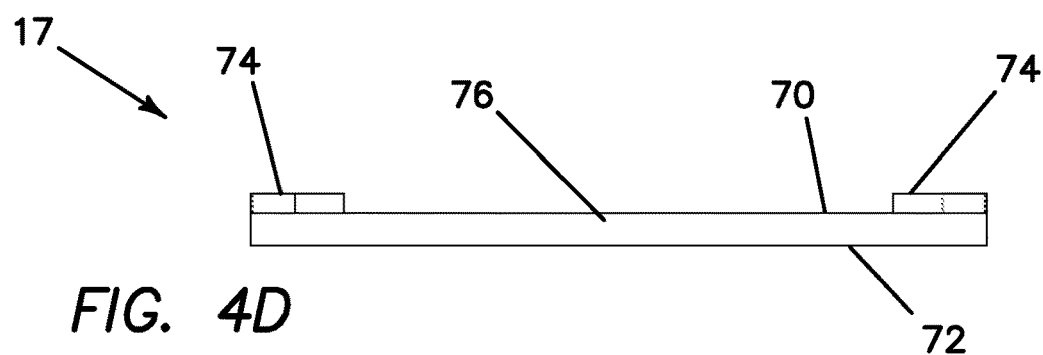
FIG. 4D is a front-elevational view of a cup retainer according to the present invention.
Figure 4E:
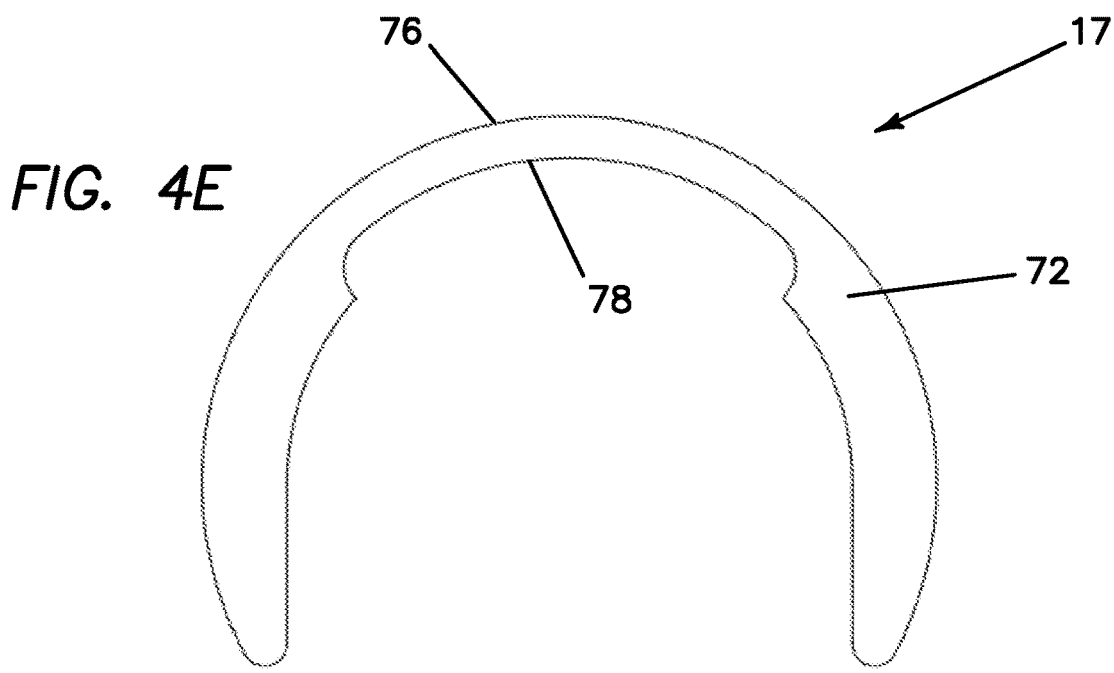
FIG. 4E is a bottom view of a cup retainer according to the present invention.
Figure 5C:
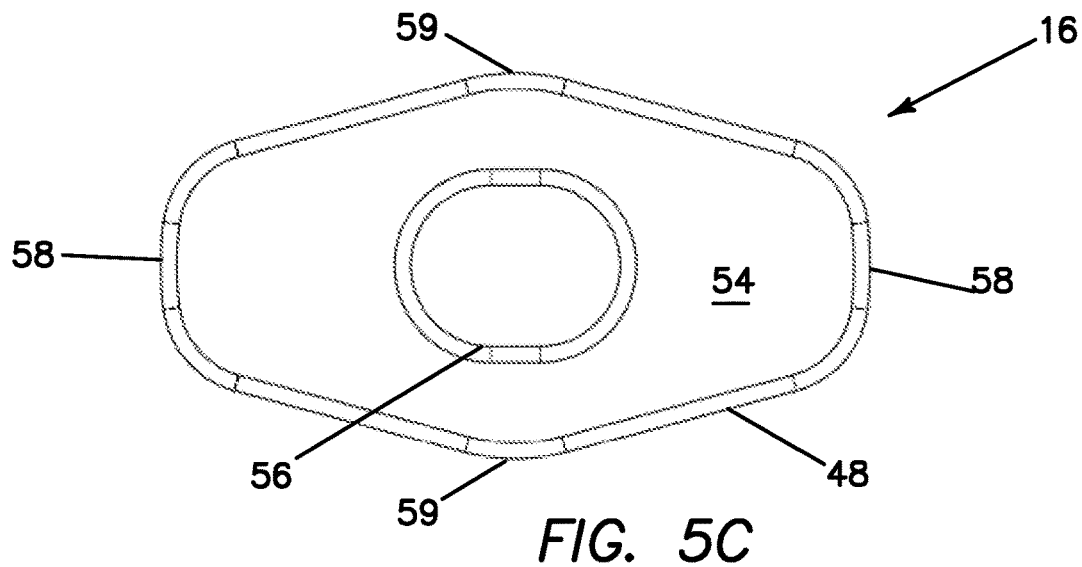
FIG. 5C is a top view of a lock according to the present invention.
Figure 5D:
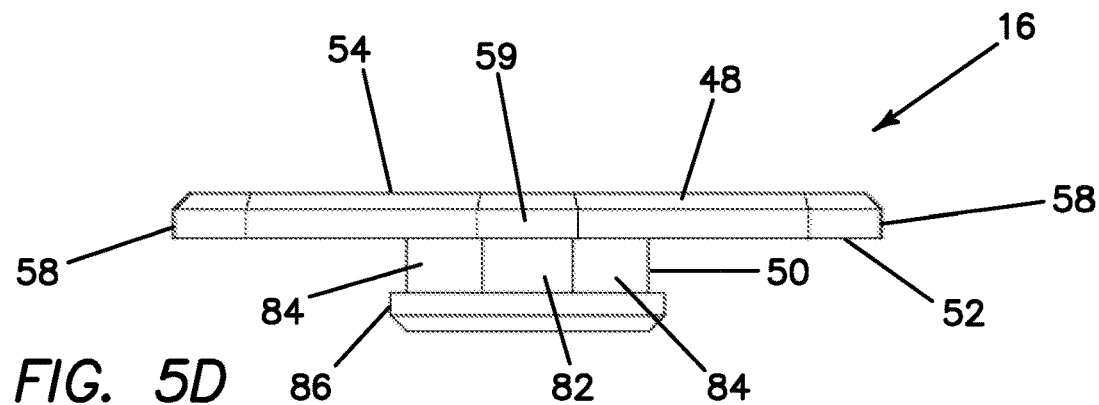
FIG. 5D is a side elevational view of a lock according to the present invention.
Figure 5E:
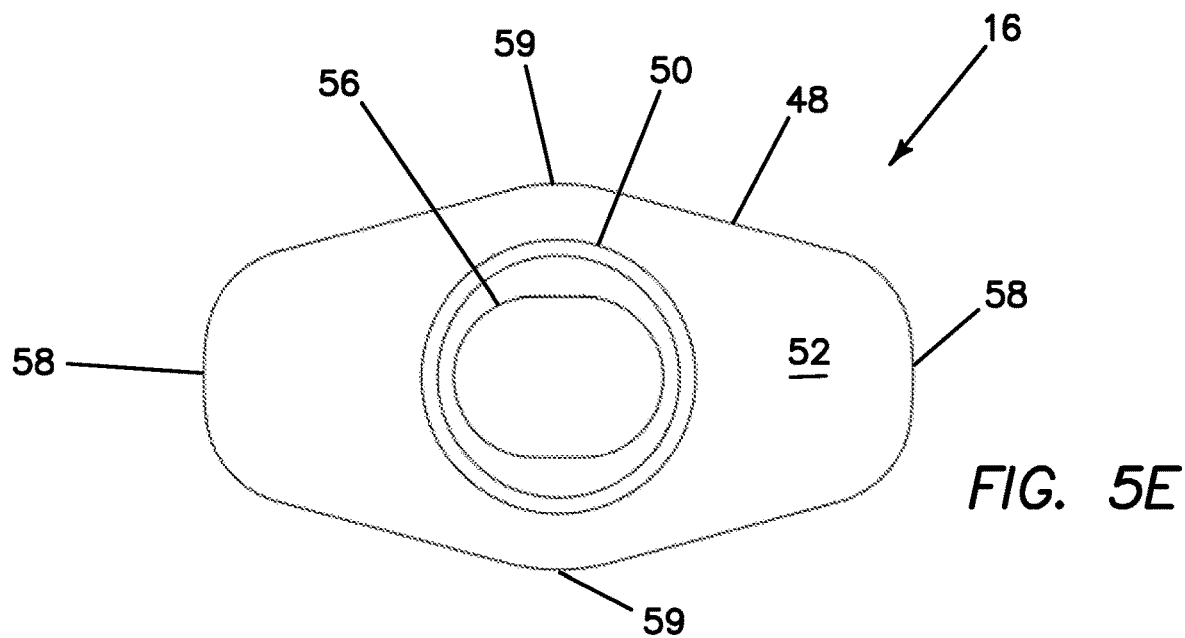
FIG. 5E is a bottom view of a lock according to the present invention.
Figure 5F:
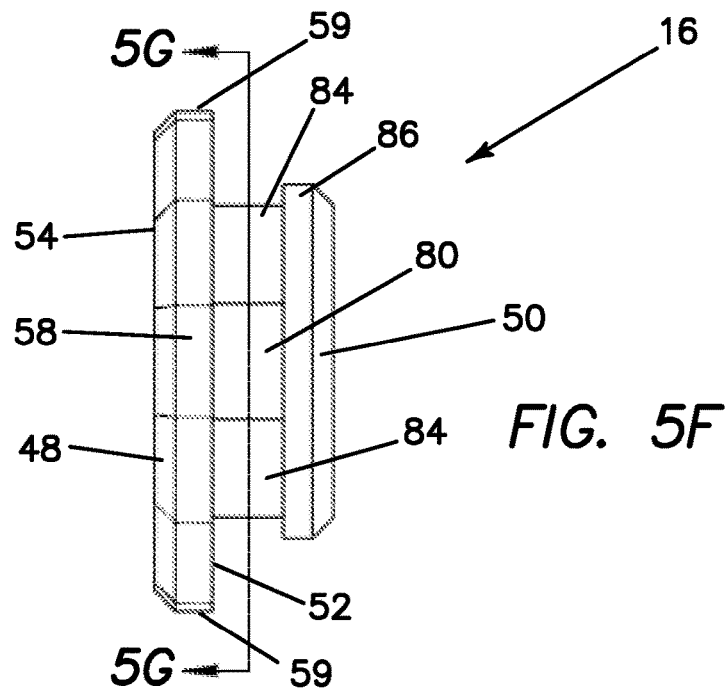
FIG. 5F is an end-elevational view of a lock according to the present invention.
Figure 5G:
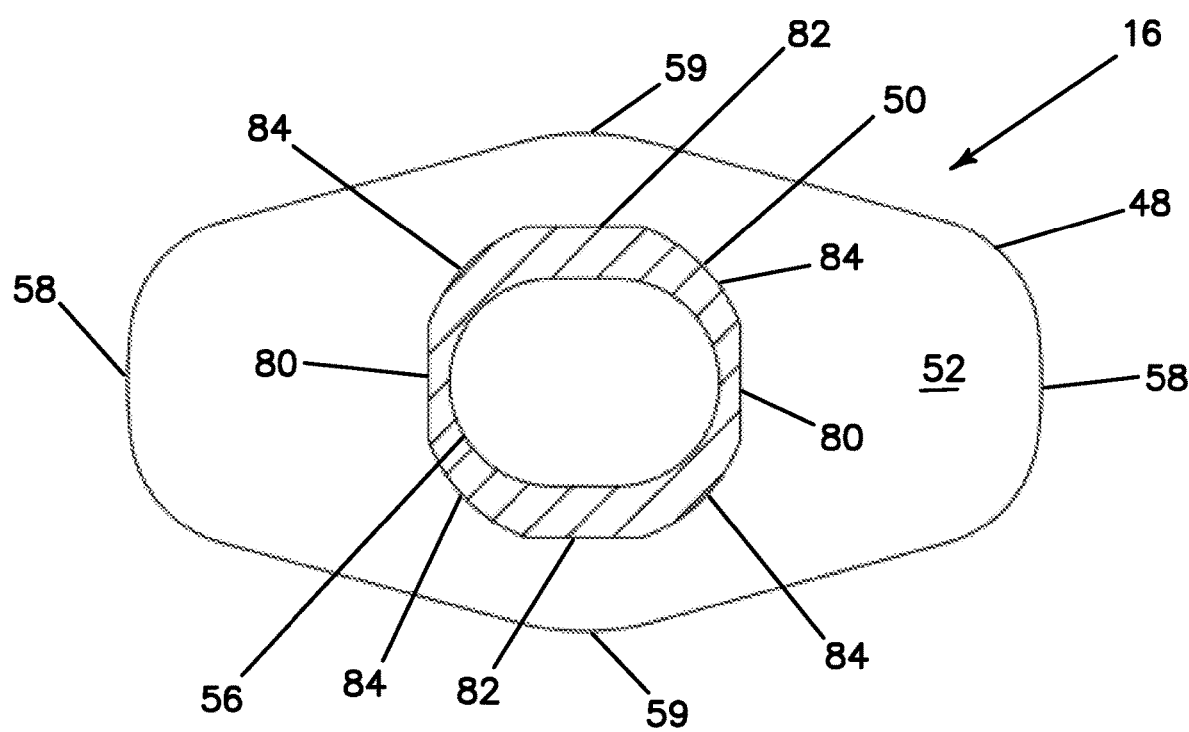
FIG. 5G is a cross-sectional view taken along line 5G-5G of FIG. 5F of a lock according to the present invention.
Figure 6A:
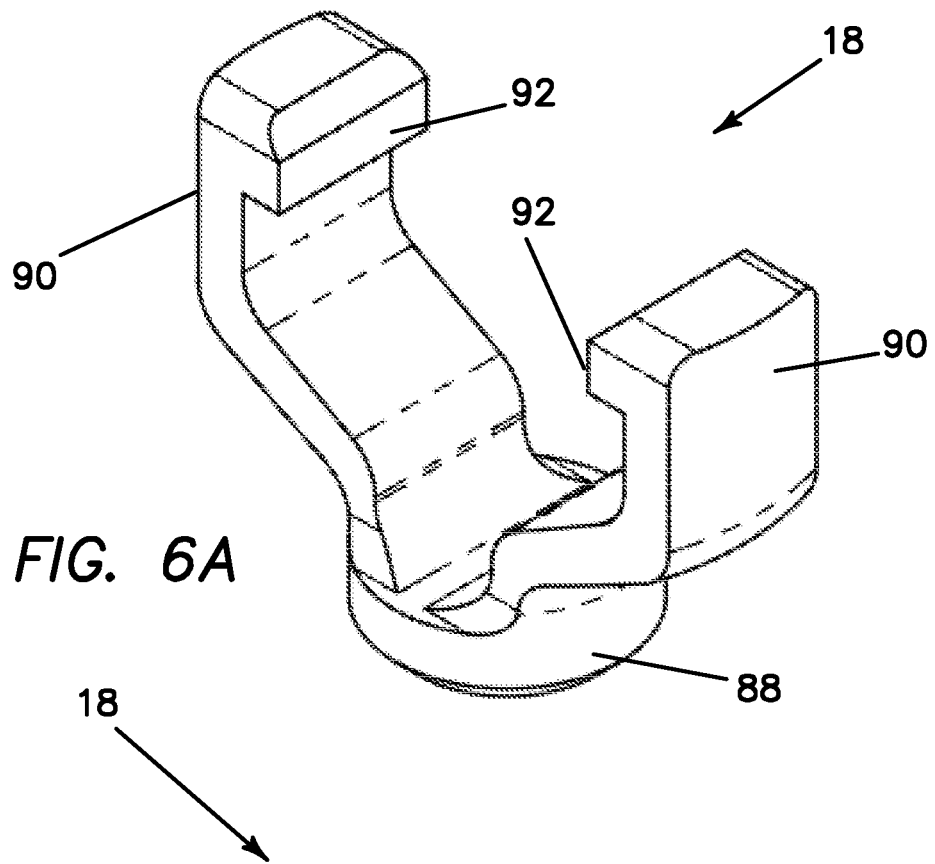
FIG. 6A is a top perspective view of a lock retainer according to the present invention.
Figure 6B:
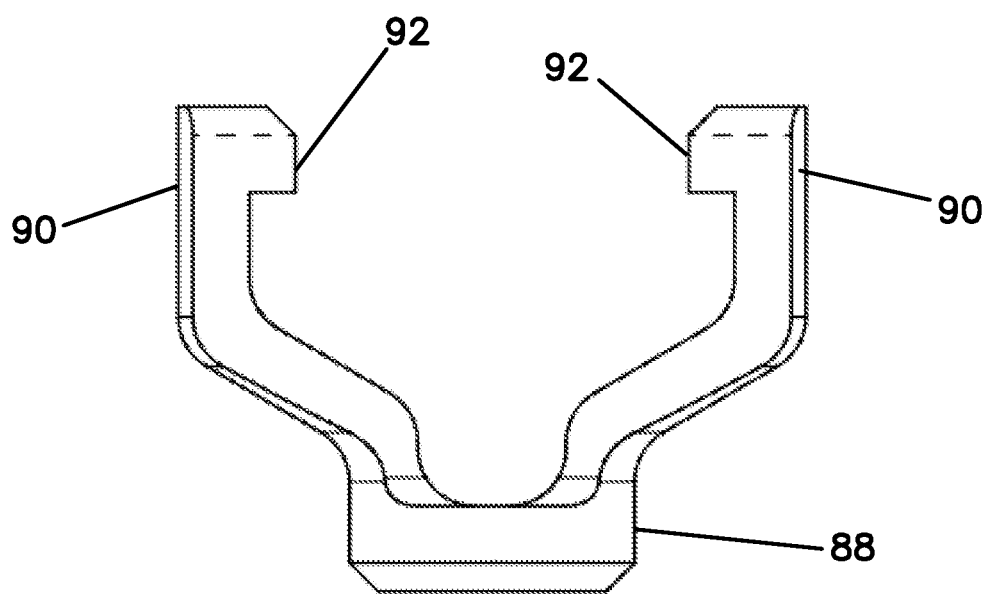
FIG. 6B is a front-elevational view of a lock retainer according to the present invention.
Figure 6C:
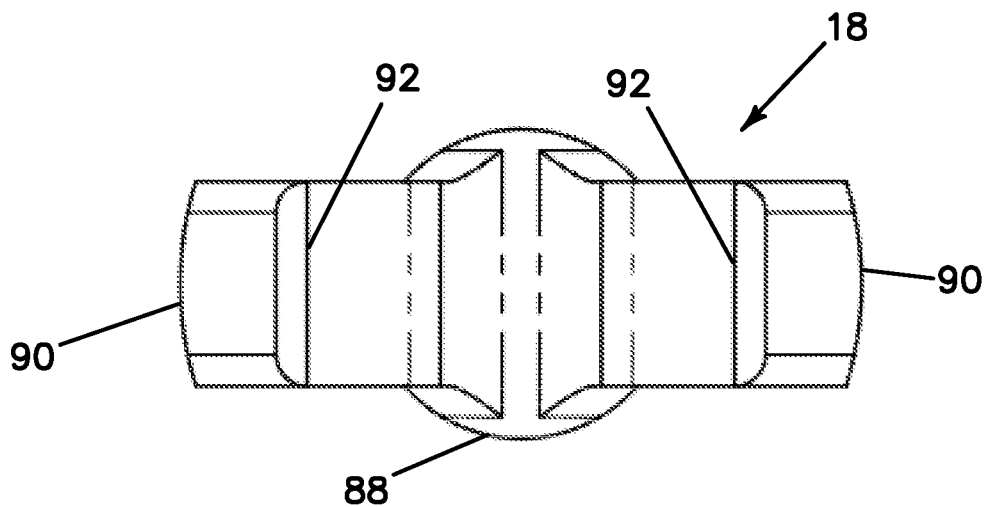
FIG. 6C is a top view of a lock retainer according to the present invention.
Figure 6D:
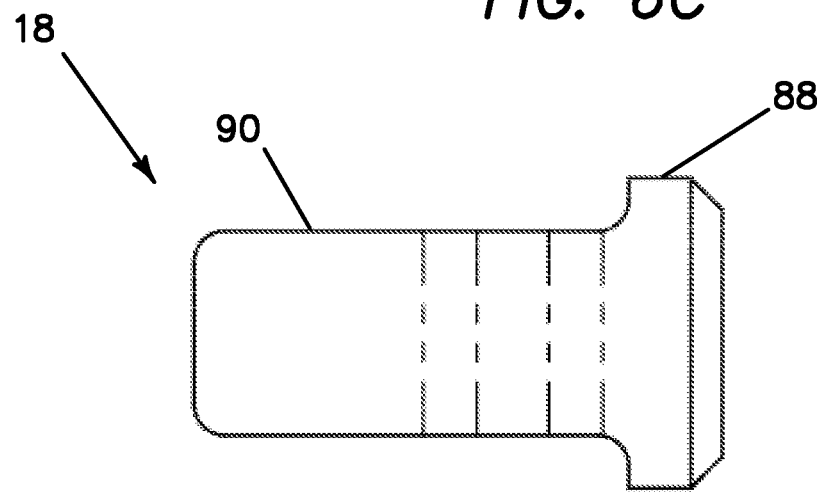
FIG. 6D is a side-elevational view of a lock retainer according to the present invention.
Figure 6E:
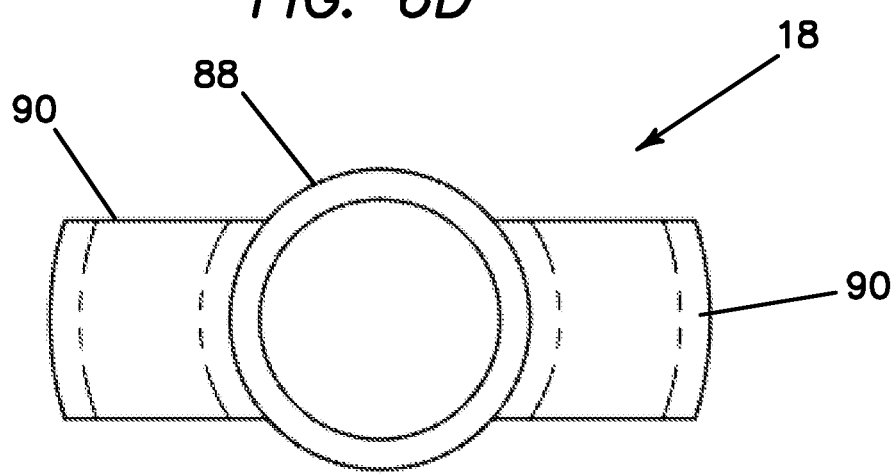
FIG. 6E is a bottom view of a lock retainer according to the present invention.
Figure 12A:
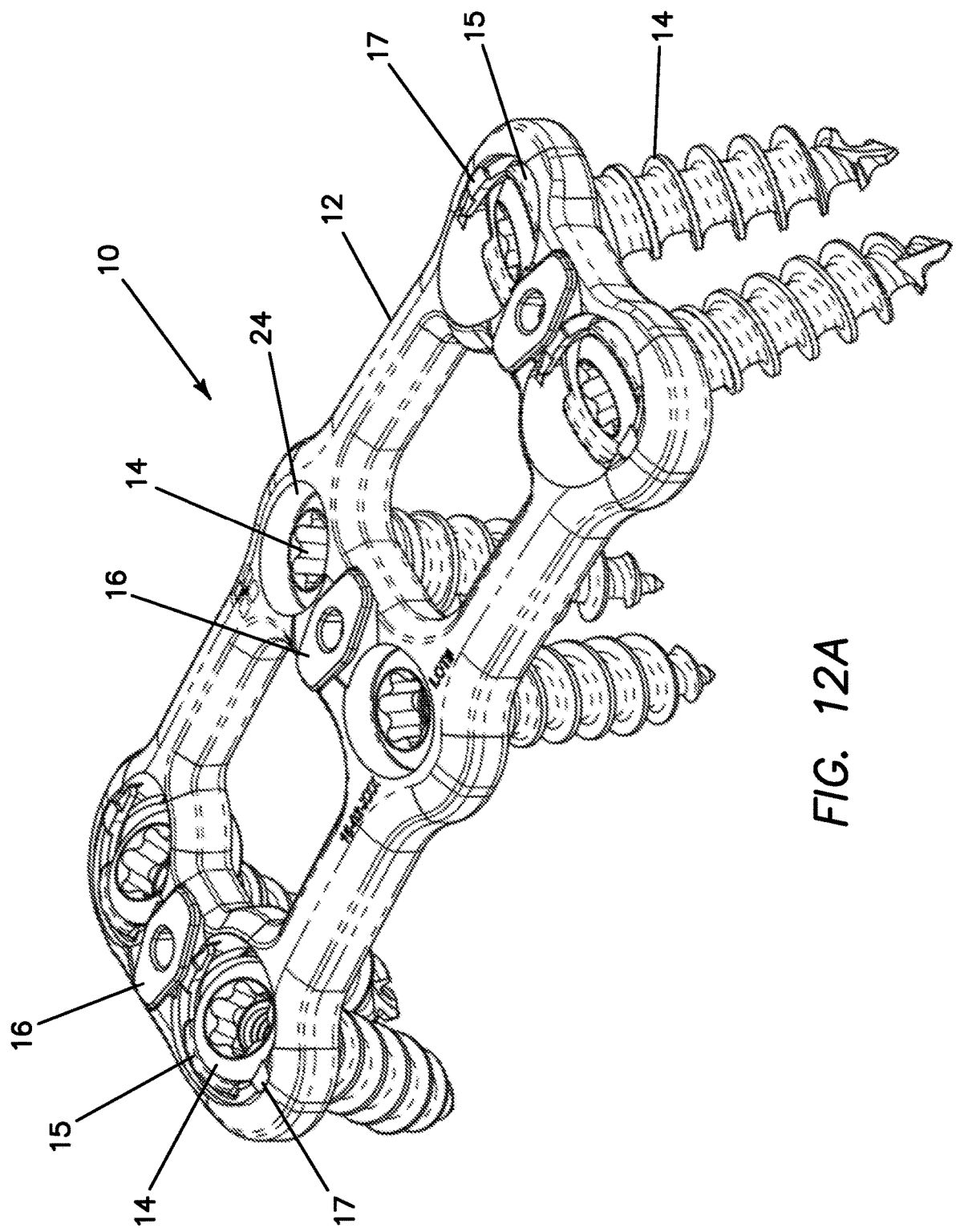
FIG. 12A is a top perspective view of a plate system in an unlocked configuration according to the present invention.
Figure 12B:
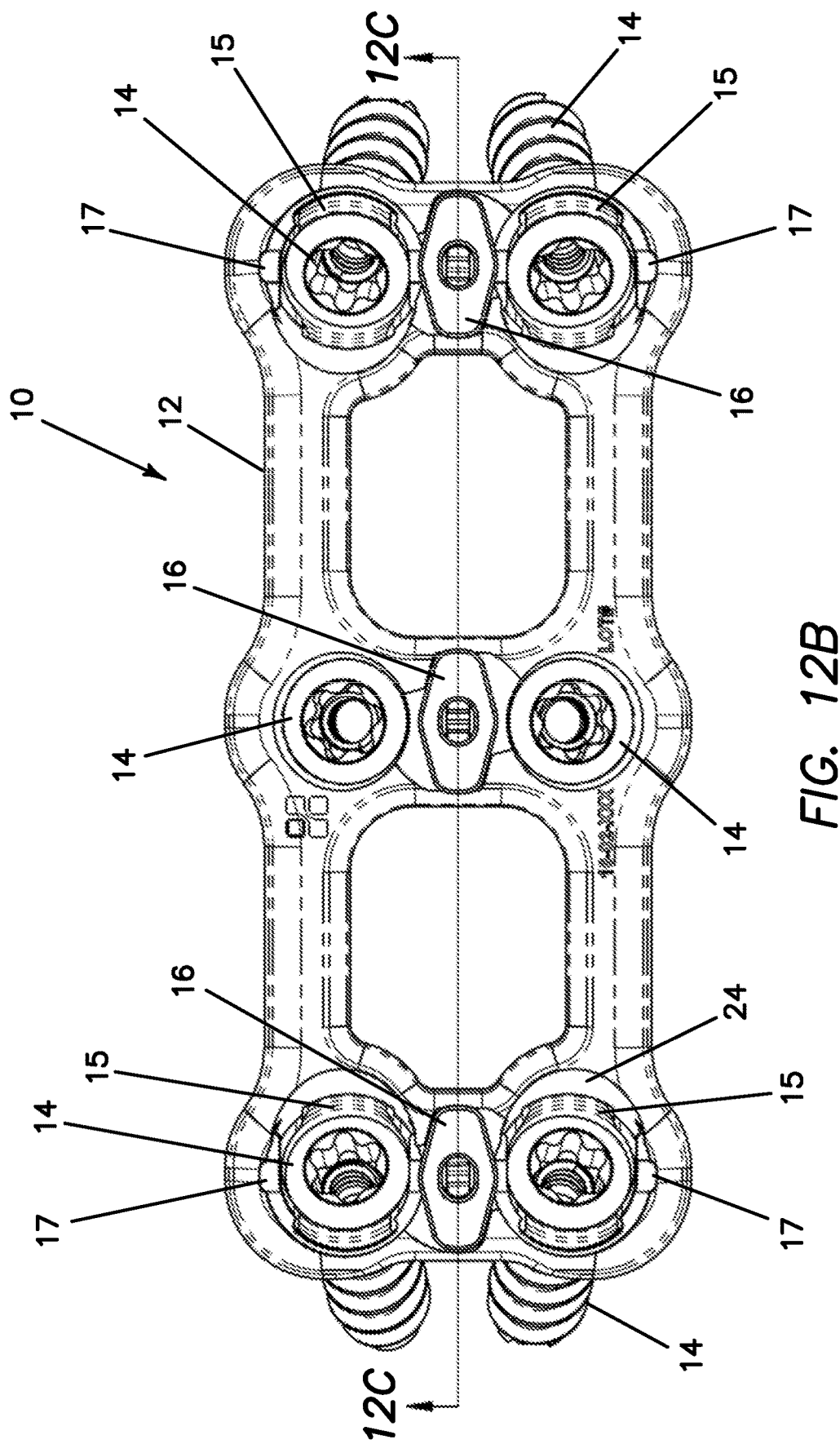
FIG. 12B is a top view of a plate system in an unlocked configuration according to the present invention.
Figure 12C:
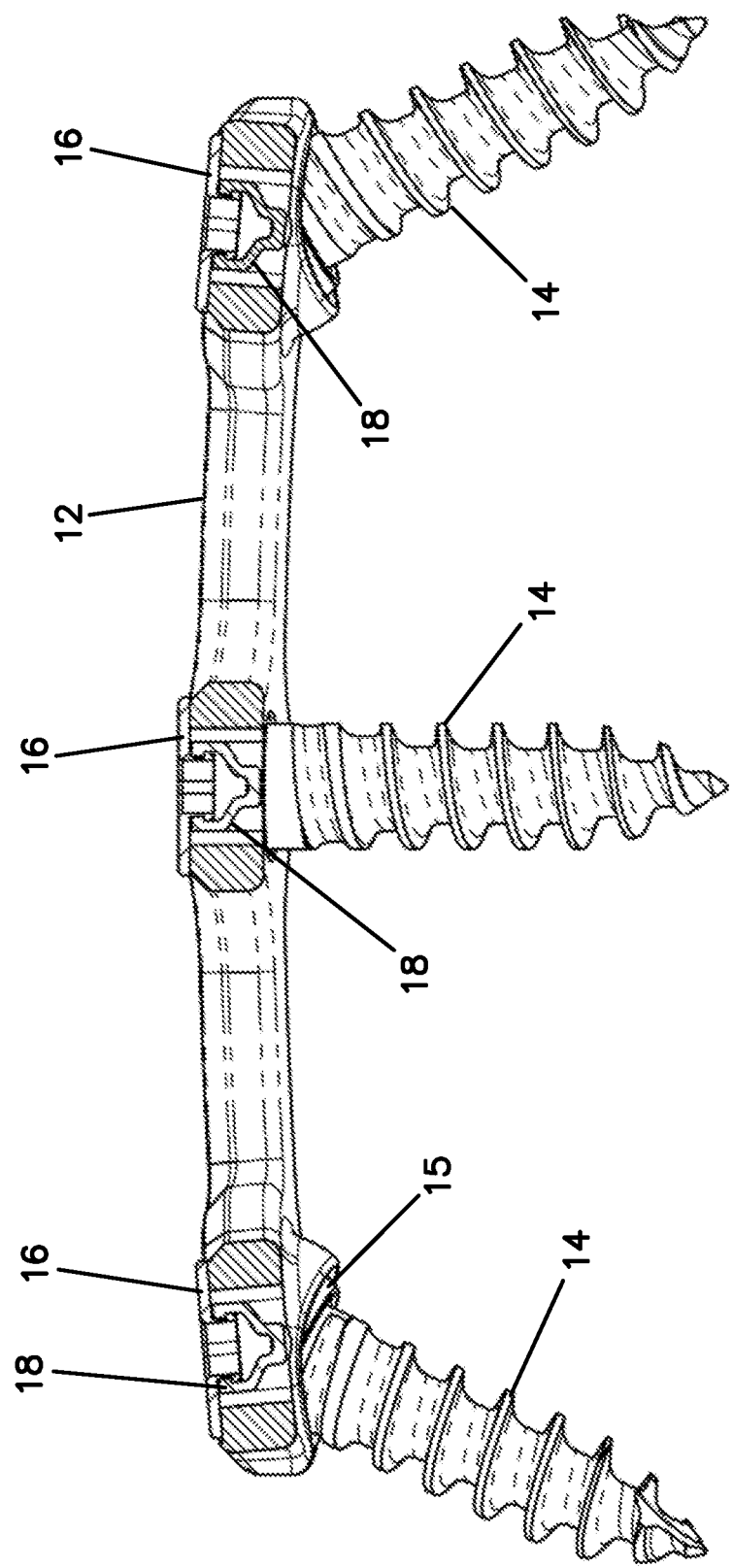
FIG. 12C is a cross-sectional view taken along line 12C-12C of FIG. 12B of a plate system in an unlocked configuration according to the present invention.
Figure 12D:
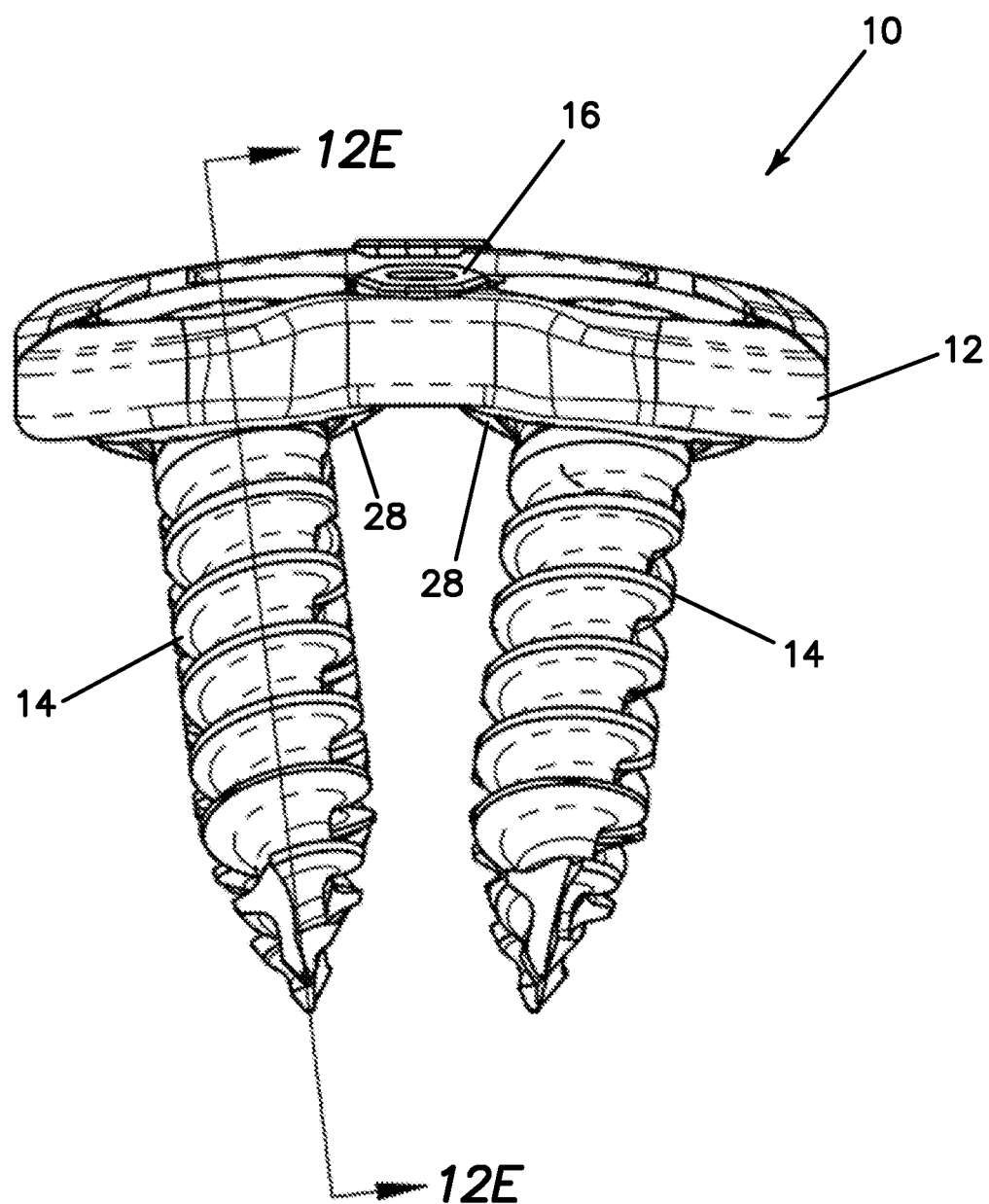
FIG. 12D is an end-elevational view of a plate system in an unlocked configuration according to the present invention.
Figure 12E:
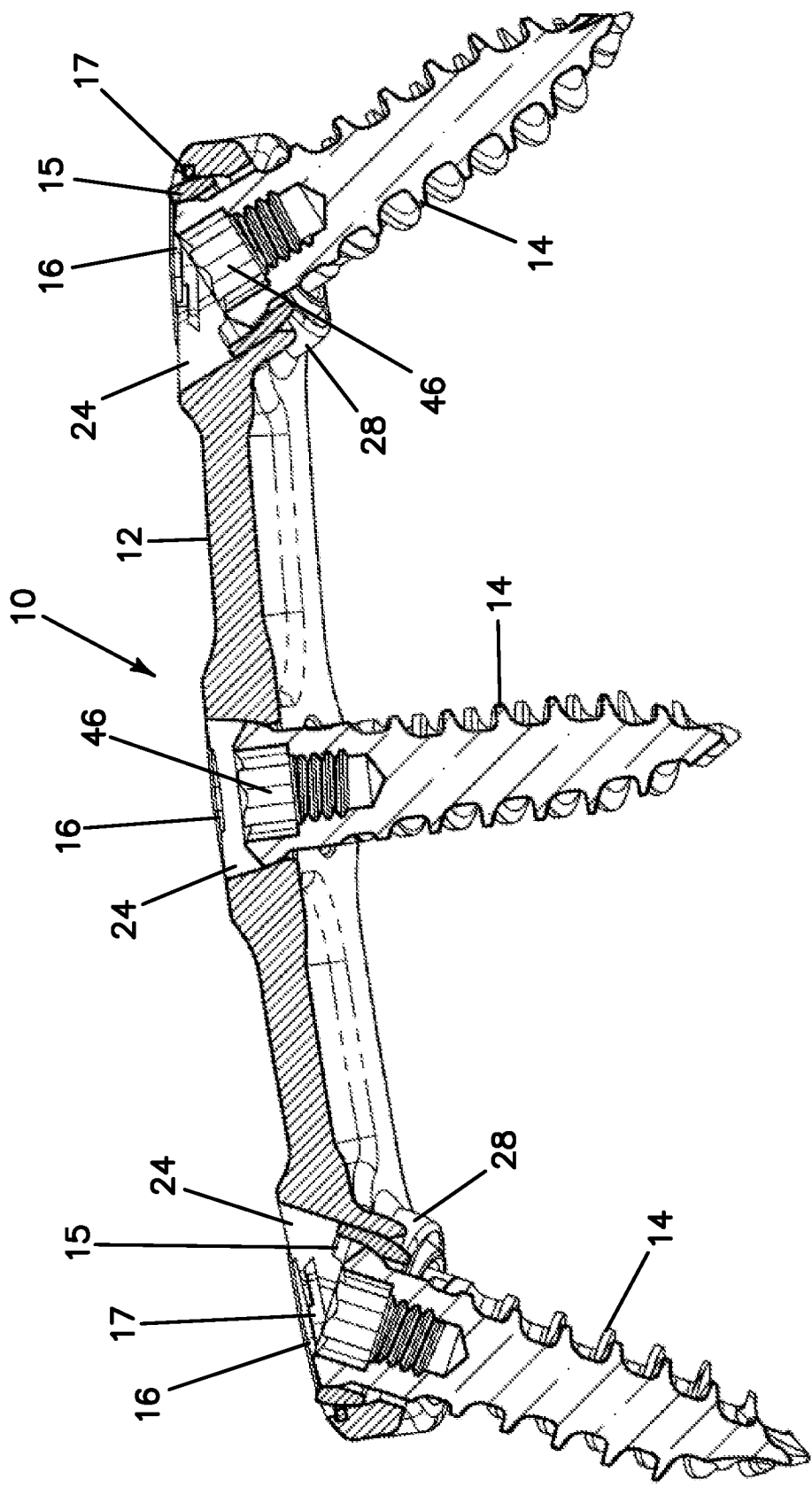
FIG. 12E is a cross-sectional view taken along line 12E-12E of FIG. 12D of a plate system in an unlocked configuration according to the present invention.
Figure 12F:
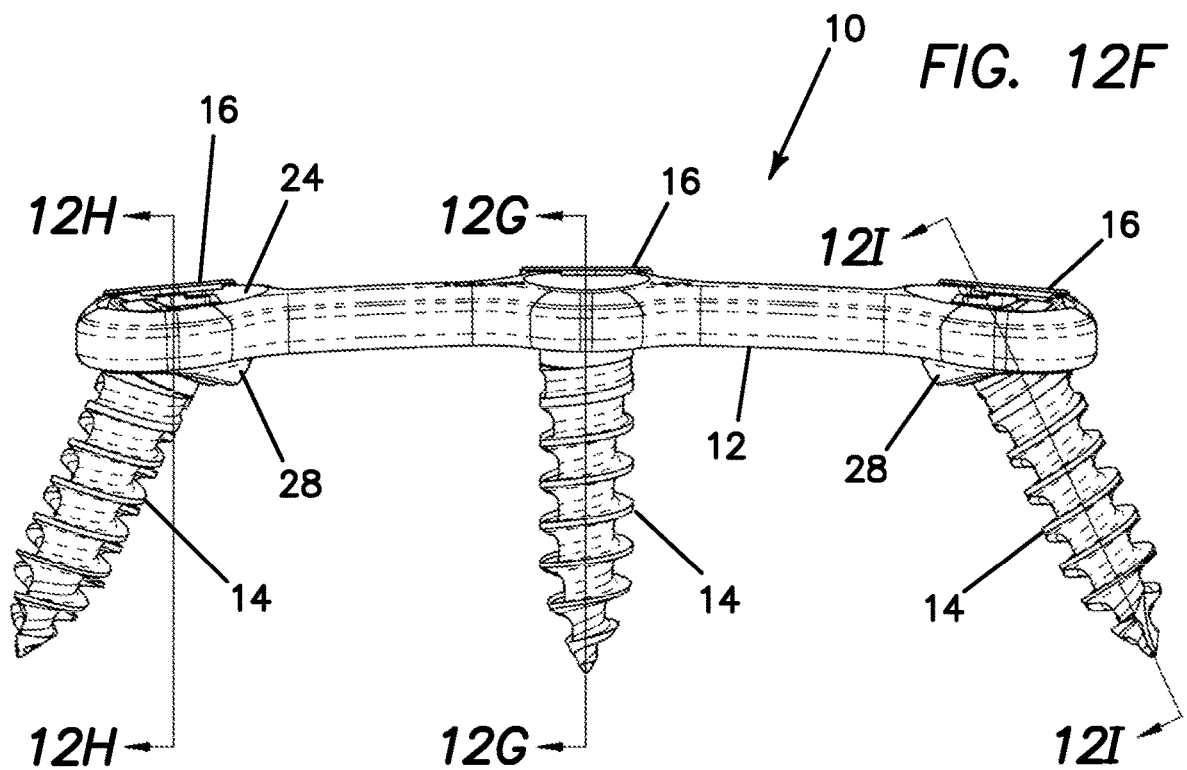
FIG. 12F is a side-elevational view of a plate system in an unlocked configuration according to the present invention.
Figure 12G:
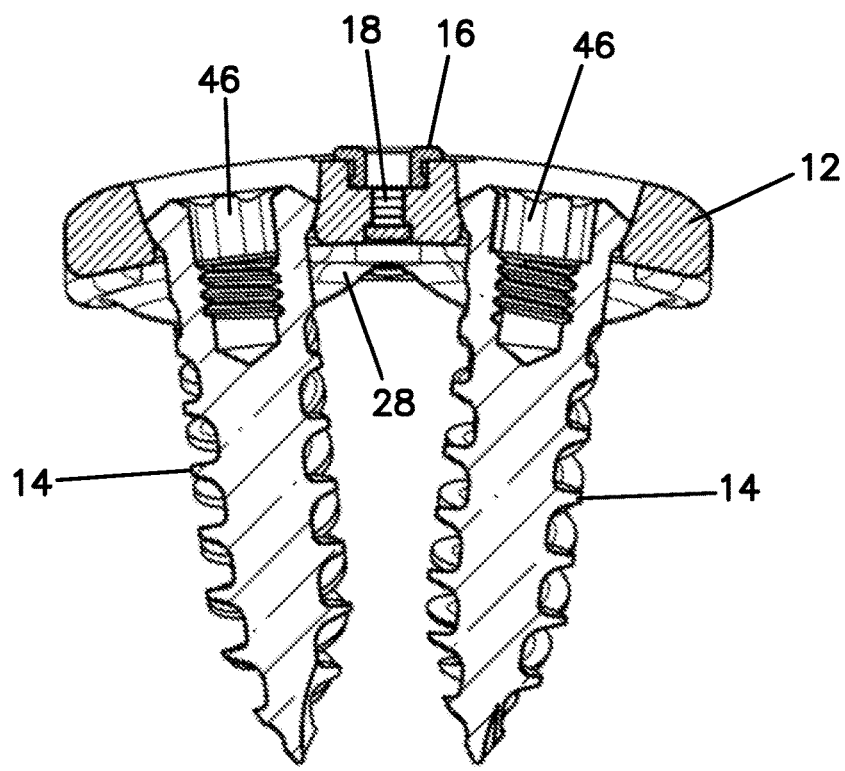
FIG. 12G is a cross-sectional view taken along line 12G-12G of FIG. 12F of a plate system in an unlocked configuration according to the present invention.
Figure 12H:
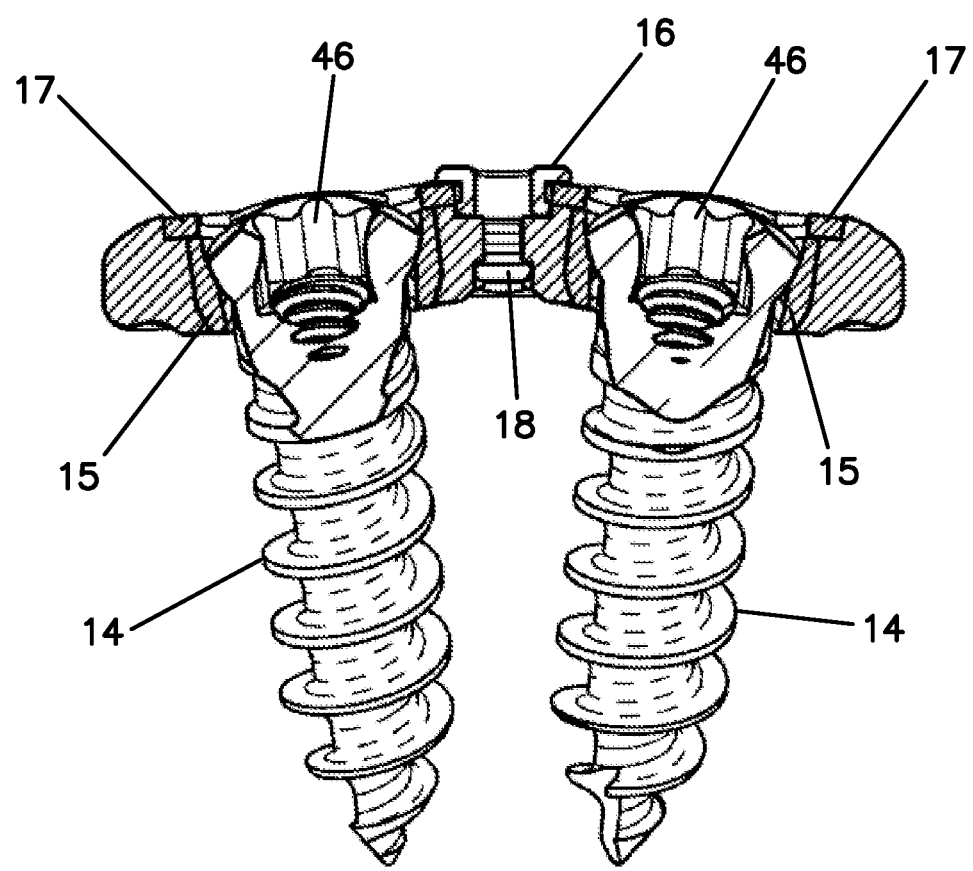
FIG. 12H is a cross-sectional view taken along line 12H-12H of FIG. 12F of a plate system in an unlocked configuration according to the present invention.
Figure 12I:
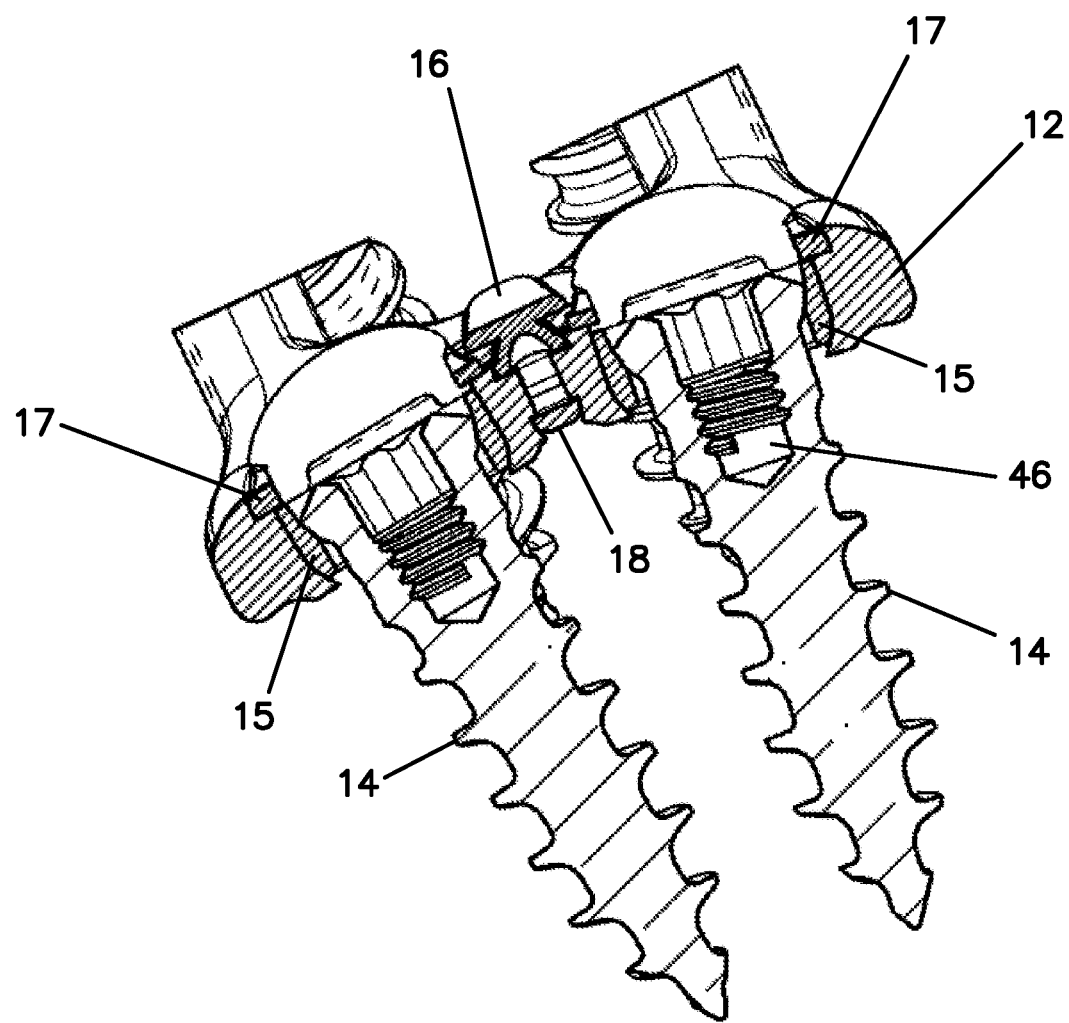
FIG. 12I is a cross-sectional view taken along line 12I-12I of FIG. 12F of a plate system in an unlocked configuration according to the present invention.
Figure 12J:
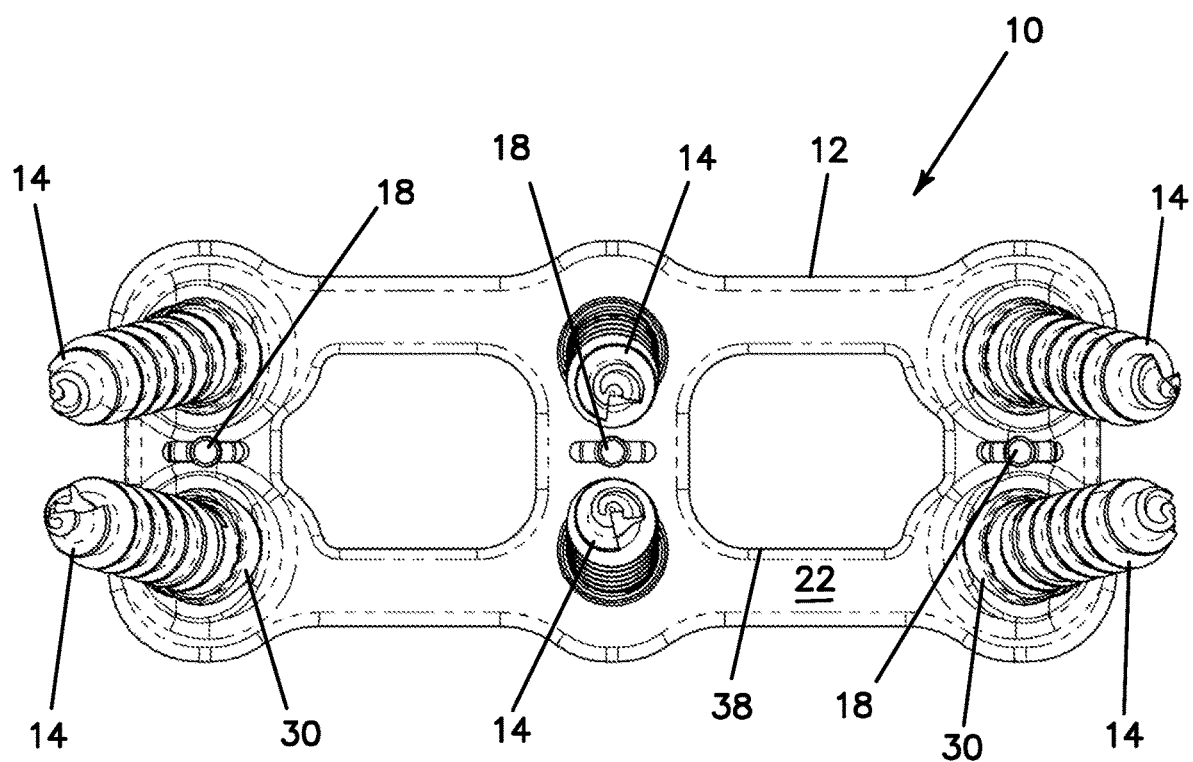
FIG. 12J is a bottom view of a plate system in an unlocked configuration according to the present invention.
Figure 13A:
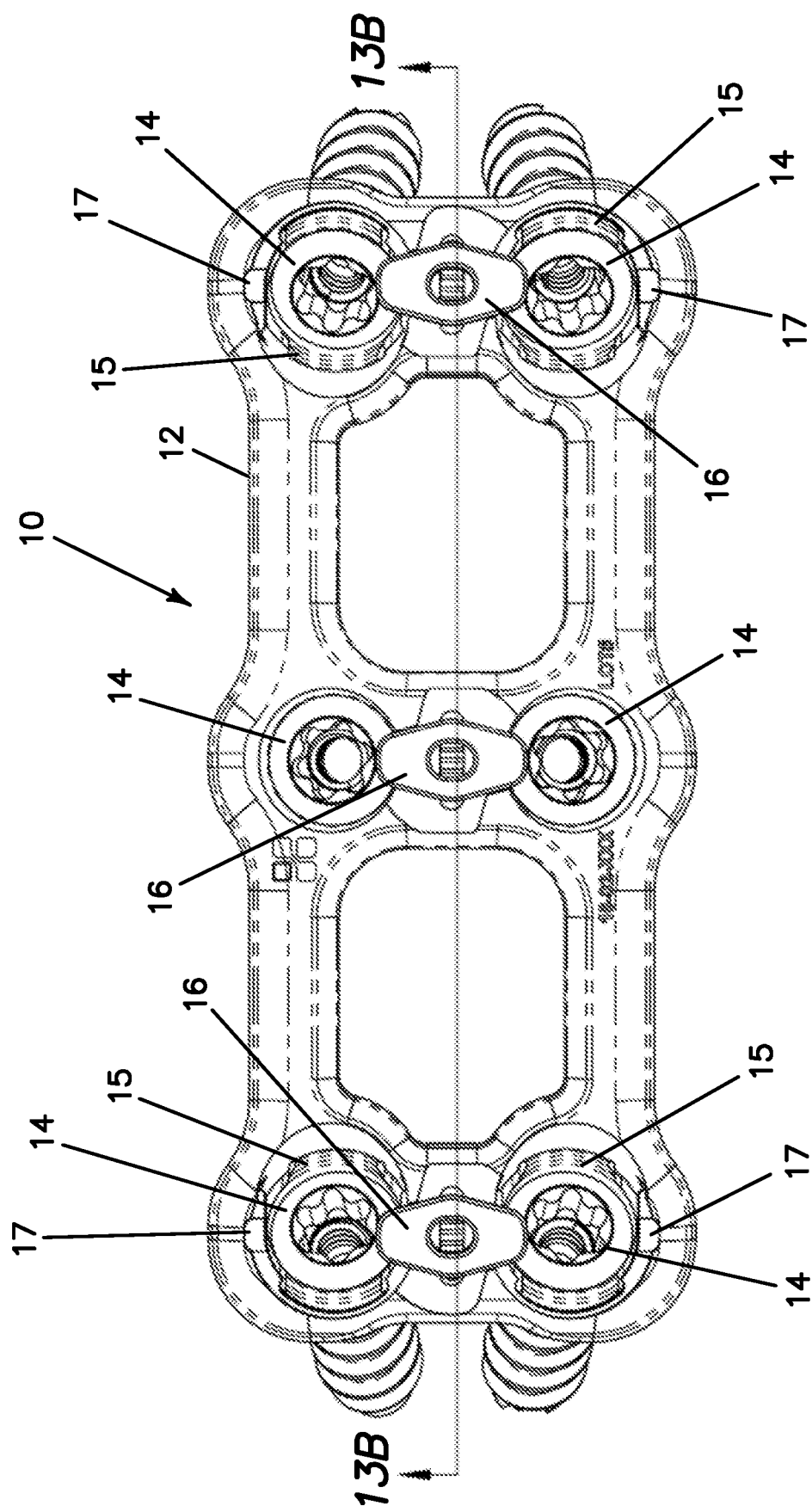
FIG. 13A is a top view of a plate system in a locked configuration according to the present invention.
Figure 13B:
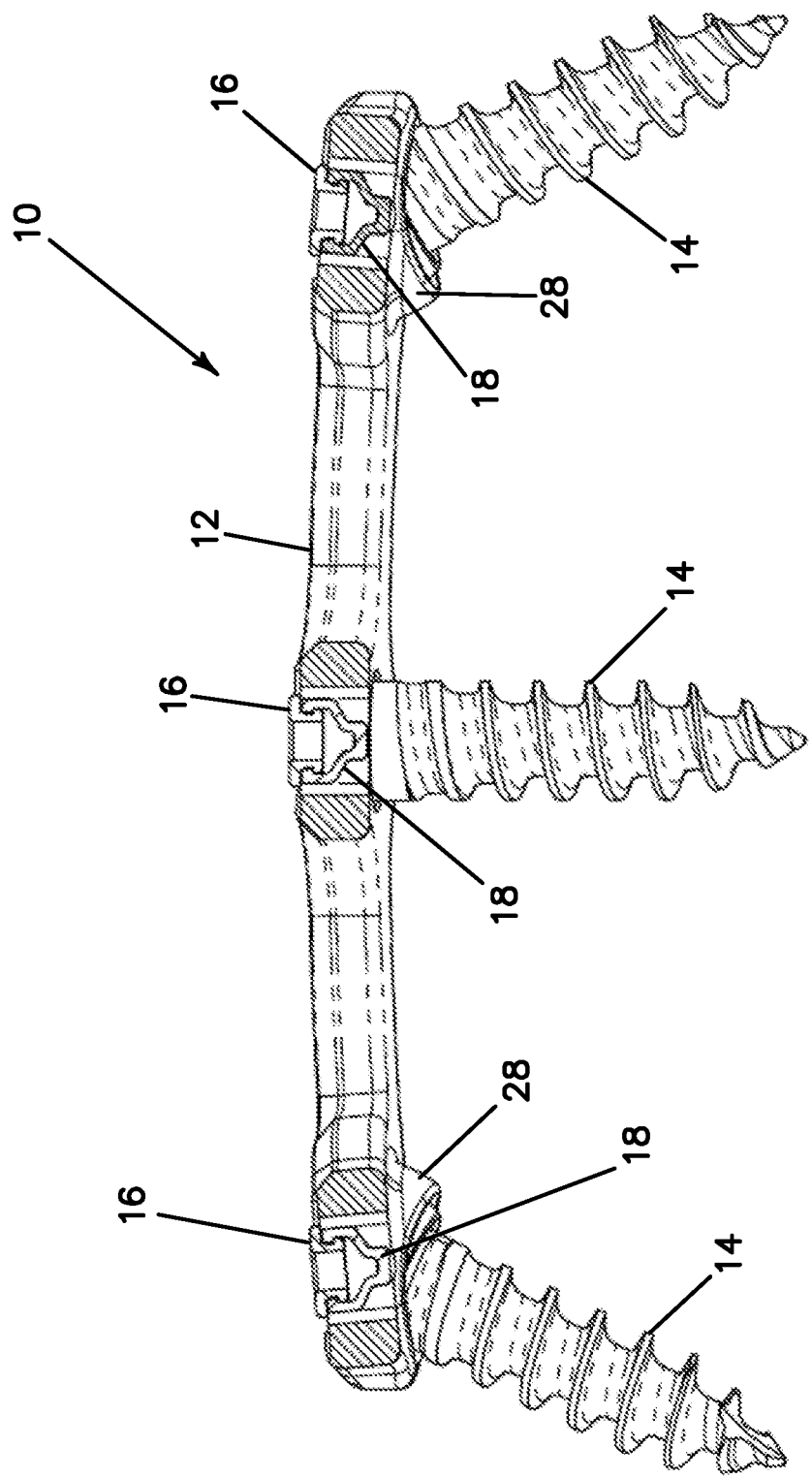
FIG. 13B is a cross-sectional view taken along line 13B-13B of FIG. 13A of a plate system in a locked configuration according to the present invention.
Figure 13C:
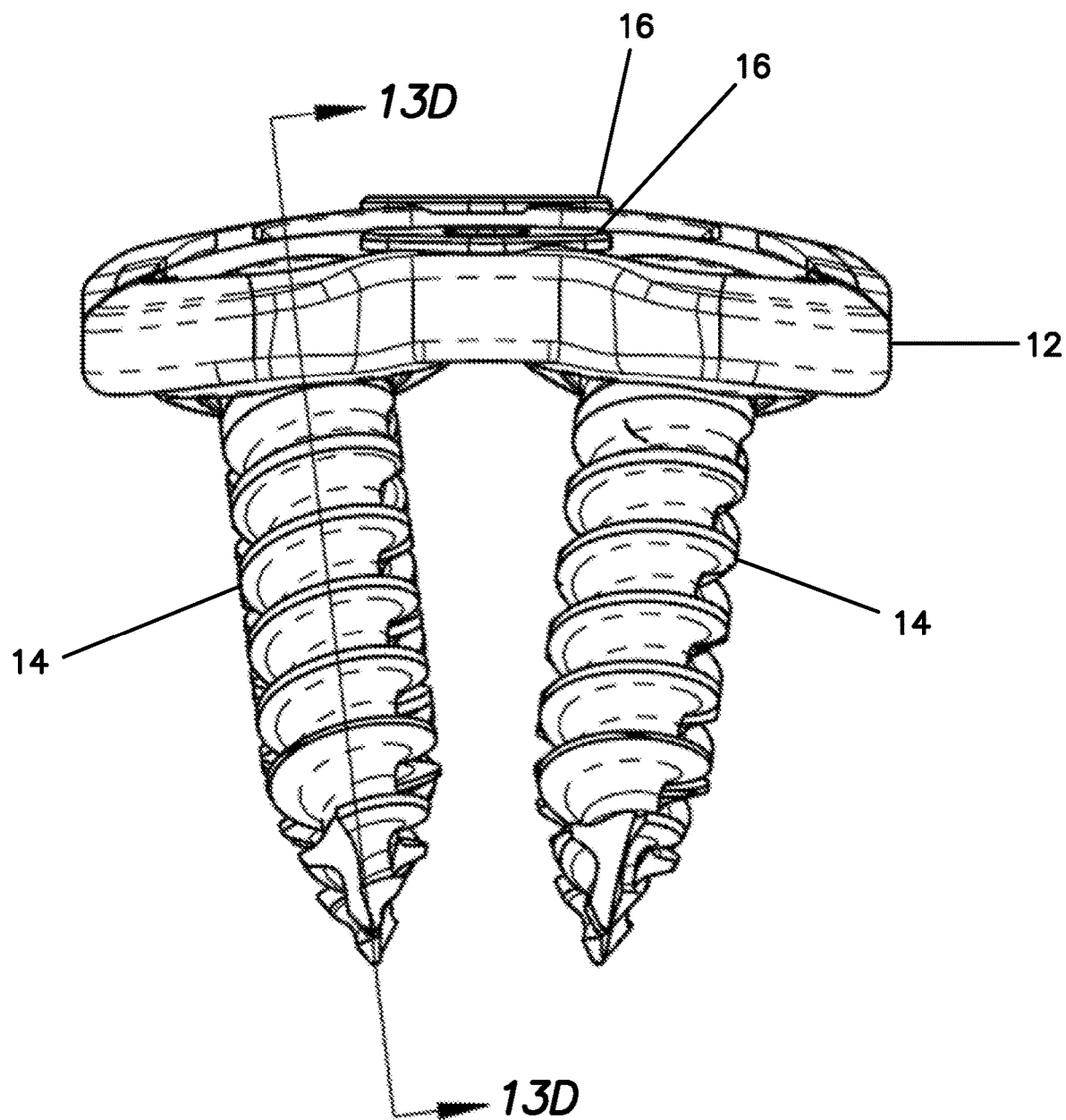
FIG. 13C is an end-elevational view of a plate system in a locked configuration according to the present invention.
Figure 13D:
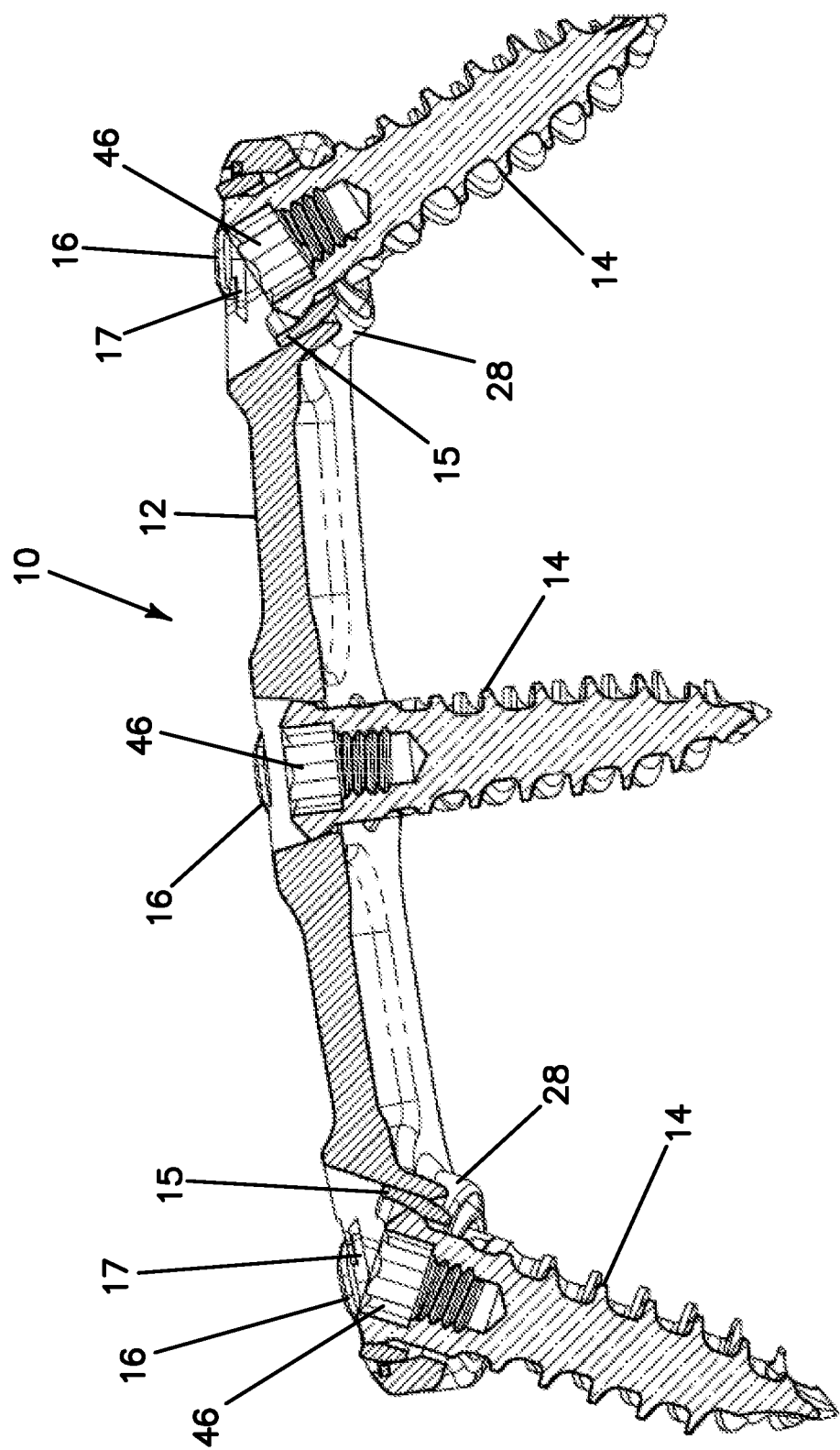
FIG. 13D is a cross-sectional view taken along line 13D-13D of FIG. 13C of a plate system in a locked configuration according to the present invention.
Figures 13E, 13F:
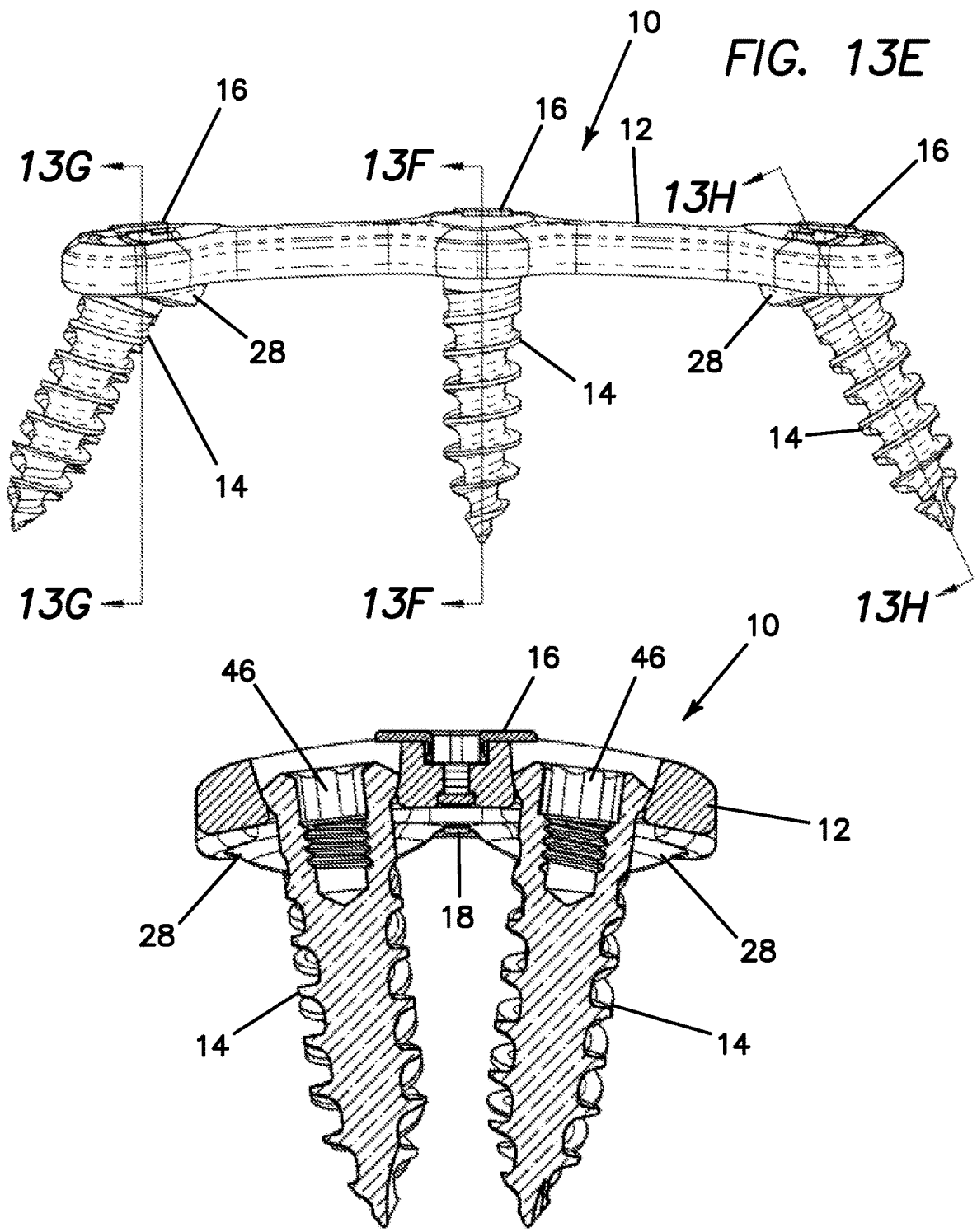
FIG. 13E is a side-elevational view of a plate system in a locked configuration according to the present invention.
FIG. 13F is a cross-sectional view taken along line 13F-13F of FIG. 13E of a plate system in a locked configuration according to the present invention.
Figure 13G:
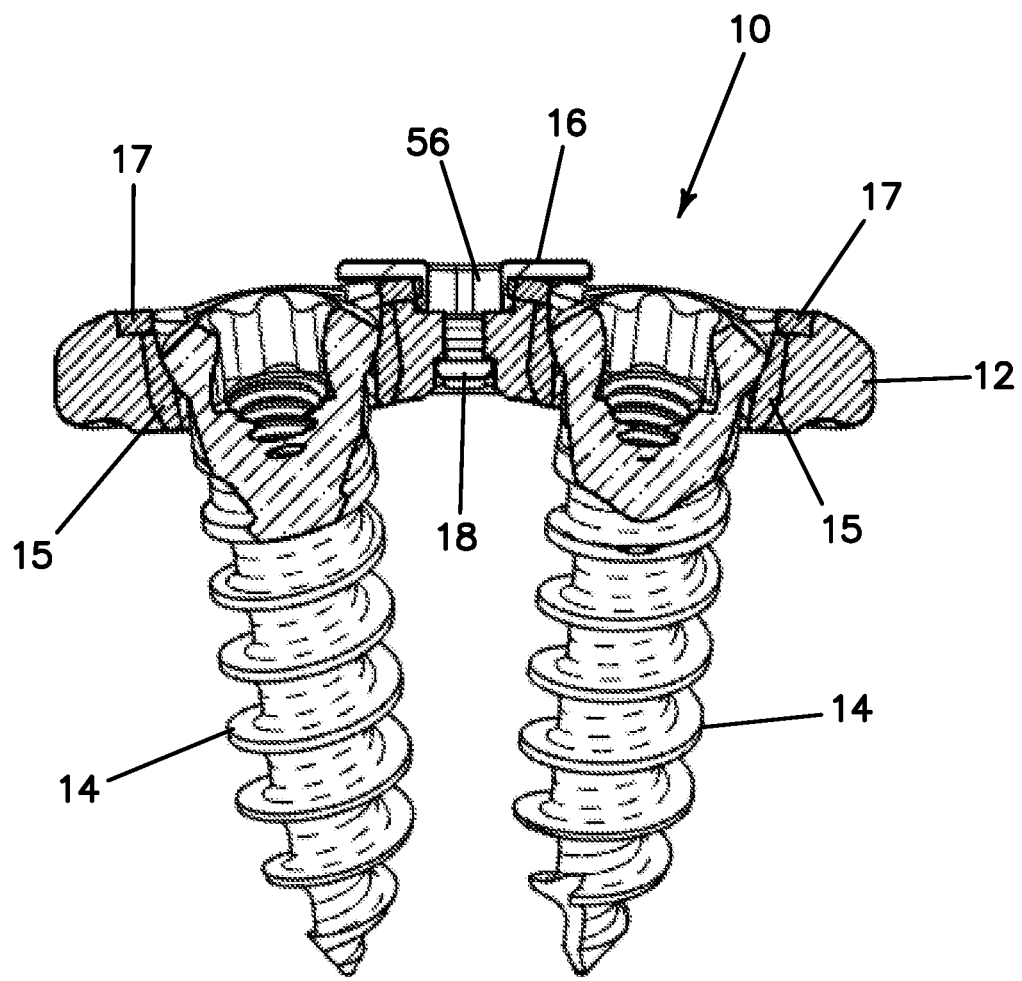
FIG. 13G is a cross-sectional view taken along line 13G-13G of FIG. 13E of a plate system in a locked configuration according to the present invention.
Figure 13H:
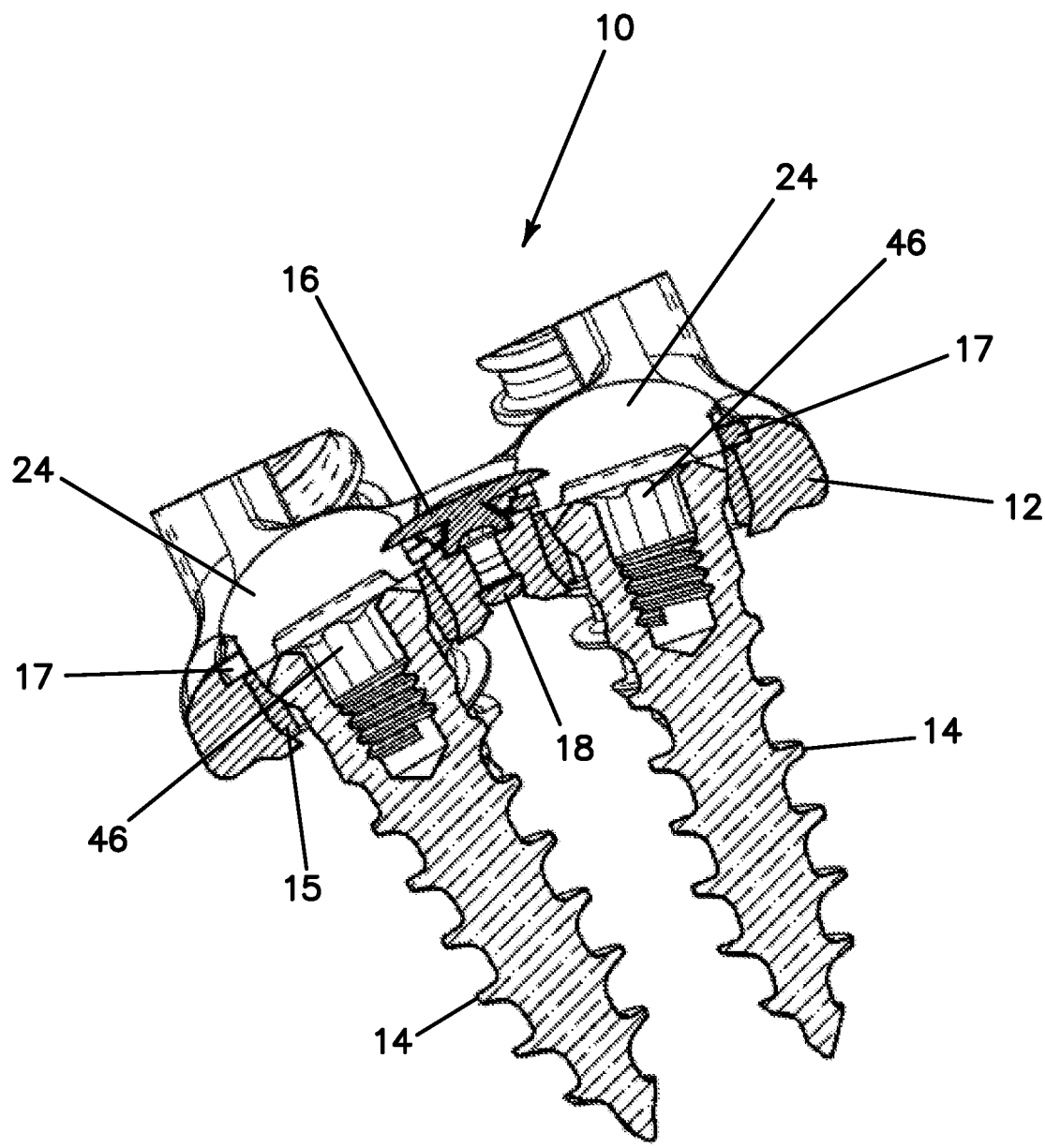
FIG. 13H is a cross-sectional view taken along line 13H-13H of FIG. 13E of a plate system in a locked configuration according to the present invention.
Figure 13I:
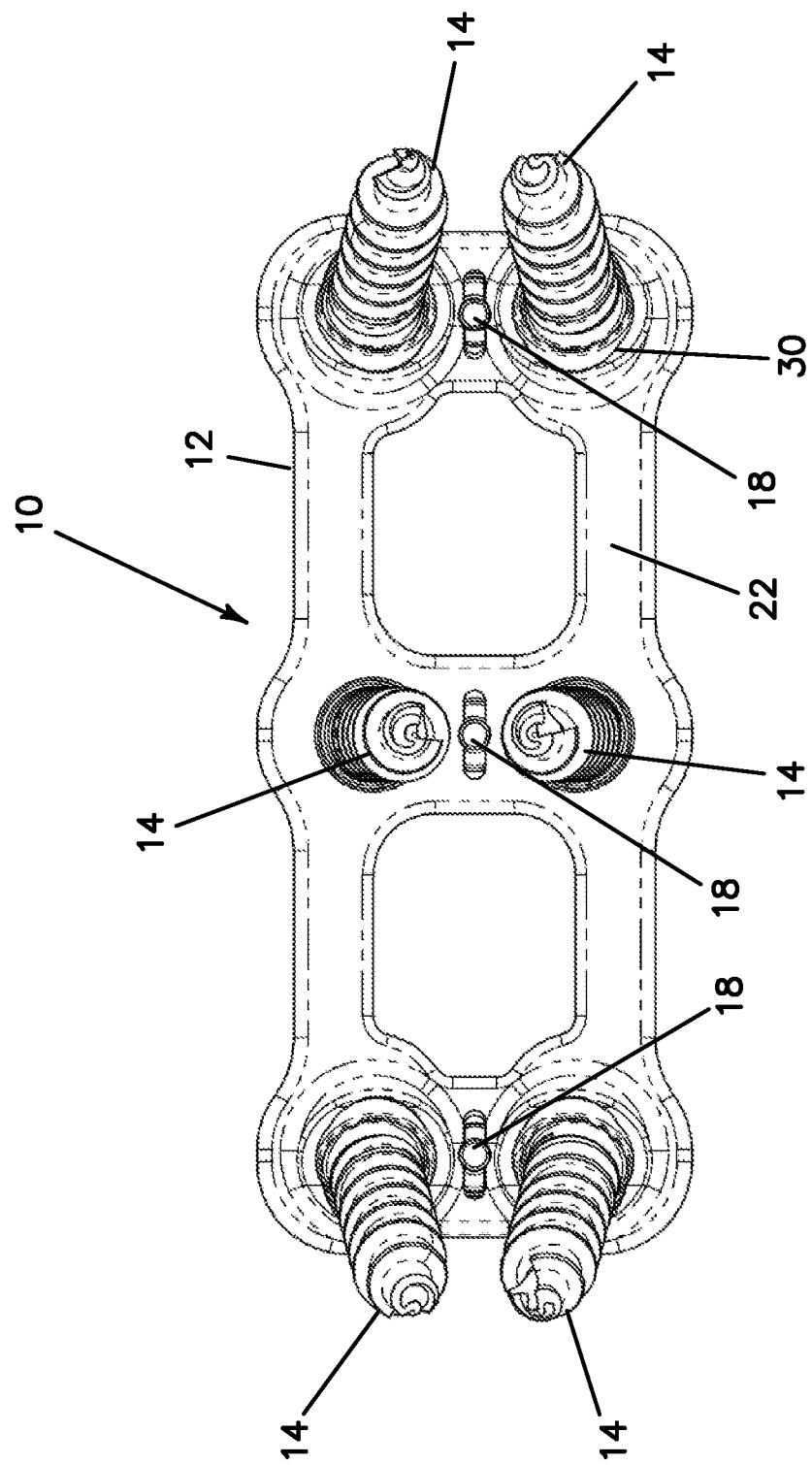
FIG. 13I is a bottom view of a plate system in a locked configuration according to the present invention.

Still referencing FIGS. 2A-2F, the plate 12 includes a plurality of through holes 24 extending through the cervical plate 12 from the upper surface 20 and through the lower surface 22. The holes 24 are configured to receive bone fasteners 14 passed there through. Each hole 24 includes a cup-receiving portion 26 connected to an extending portion 28 near the lower surface 22 as seen in FIG. 2F. The cup-receiving portion 26 is recessed from the top surface 20 such that the cup 15 and the head of the fastener 14, which is received inside the cup 15, does not protrude beyond the upper surface 20 of the plate 12 in order to maintain a low profile for the plate 12. Each cup receiving portion 26 includes two oppositely disposed flat surfaces 27. The flat surfaces 27 are configured to mate with flat surfaces 67 that are oppositely disposed on each cup 15. Each through hole 24 has an exit opening 30 at the lower surface 22 to allow room for the angulation of inserted fasteners 14. The exit opening 30 at the lower surface 22 is oblong/elliptical in shape to correspond with the predominant forward/backward angulation configuration of the cup 15 with respect to the plate 12 when the cup is located inside the cup receiving portion 26. The long axis of the elliptical exit opening 30 runs parallel to the longitudinal axis. The elongated shape of the exit opening 30 is visible in FIGS. 2F, 12J and 13I. The extending portion 28 is provided preferably at the two top and two bottom through holes 24. The middle two through holes 24 do not demand the extreme angulation required at the ends of the plate 12 and, therefore, are not provided with extending portions 28 at the lower surface 22 in a preferred embodiment. The cup-receiving portion 26 forms a part-cylindrical seat or curved surface configured for a complimentary part-cylindrical or curved outer surface of the cup 15. In one variation, the size of the through hole 24 is configured such that the cup-receiving portion 26 is large enough to allow a bone fastener 14 to pass all the way through the plate 12 and wherein the presence of a cup 15 in the through hole 24 reduces the size of the through hole 24 such that the head portion of the fastener 14 is not allowed to pass through the cup 15 and plate 12 combination. The distal lower portion of the through hole 24 includes a cylindrical portion that has a smaller diameter in comparison to the proximal upper portion of the through hole 24 to retain the cup 15 inside the through hole 24. As can be seen in FIGS. 2C-2D, the extending portion 28 is angled at an angle 29 with respect to the lower surface 22 of the plate 12. The angle 29 is greater than 90 degrees. The extending portion 28 advantageously increases the range of angulation for the cup 15 and the fastener 14 located inside the cup 15. Without the depending extending portion 28, the angulation of the fastener 14 would be limited by abutting the plate 12 instead of depending below the plate 12 to increase the range of motion before abutting the plate 12. The fact that the extending portion 28 extends beyond the lower surface 22 of the plate 12 and that the extending portion 28 is further angled with respect to the horizontal advantageously provides an angled starting point for the cup 15 from which the fastener 14 can further angulate from and clear the plate 12 at extreme angles before abutting the plate 12. This feature advantageously permits the fastener 14 to be driven into adjacent vertebral bodies more easily providing the surgeon a larger range of polyaxial angulation for the fastener.

FIGS. 2A-2F depict a plate 12 having three sets or three pairs of fastener through holes 24 spaced apart along the plate centerline for driving fasteners 14 into and stabilizing three vertebral bodies for creating a two-level construct. Each set of fastener through holes 24 includes two holes 24 spaced oppositely apart from each other along the centerline of the anterior cervical plate 12. Each set or pair of through holes 24 is adapted for receiving two fasteners 14 to be driven into a single vertebral body.

Still referencing FIGS. 2A-2F, the plate 12 further includes a recess 34 located between the through holes 24 of each pair of through holes 24. The recess 34 is configured for receiving the lock 16 such that the lock 16 does not substantially protrude from the upper surface 20 of the plate 12 when in a locked position in order to maintain the desired low profile. A lock aperture 36 is formed in the recess 34 at the centerline for coupling the lock 16 to the plate 12. The lock aperture 36 extends all the way to the lower surface 22 of the plate 12. In particular, the lock aperture 36 is sized and configured to receive the lock retainer 18. Also, the lock aperture 36 has a circular recess within recess 34 that is sized and configured to receive the circular lower portion of the lock 16. The recess 34 further includes four stops 33. The stops 33 serve as abutments to limit the rotation of a lock 16 disposed inside the plate 12. The stops 33 limit rotation of the lock 16 to 90 degrees. The recess 34 further includes slots 37 for receiving a part of the cup retainer 17. In particular, the slots 37 are provided in a location that accommodates the protrusions 74 of the cup retainer 17.

The plate 12 also includes two larger openings 38 located between each pair of through holes 24 that effectively reduce the overall weight of the plate 12 and provide a visualization pathway to monitor bone graft progress between the vertebral bodies. Each through hole 24 includes an interior groove 35. The groove 35 is sized and configured to receive the cup retainer 17 such that the cup retainer 17 snaps into groove 35. The groove 35 is provided in those through holes 24 that are at the distal ends, top and bottom, of the plate 12 where maximum fastener angulation is mostly needed. In one variation, the middle two through holes 24 are not sized and configured to receive a cup 15 and, therefore, are also not provided with a groove 35 for the cup retainer 17.

Turning now to FIGS. 3A-3G, the cup 15 will now be described. The cup 15 is substantially cylindrical in shape defining an inner surface, an outer surface, a top surface 61 and a bottom surface 63. The inner surface of the cup 15 defines a lumen 65 that is sized and configured to receive at least a portion of a fastener 14. A longitudinal axis extends through the lumen and along the length of the cup 15. The cup 15 includes a top opening and a bottom opening. The top opening is generally defined by the inner surface intersecting with the top surface 61 and the bottom opening is generally defined by the inner surface intersecting with the bottom surface 63. The bottom surface 63 and bottom opening generally lie in the same plane that is generally perpendicular to the longitudinal axis of the cup. The top surface 61 includes a back 60 of the cup 15 interconnected to a front 62 of the cup 15. The back 60 has a distance from the bottom surface 63 that is greater than a distance from the bottom surface 63 to the top surface at the front 62. The top surface 61 transitions from the back 60 to the front 62 to define a landing surface 64 on either side of the front 62. The landing surfaces 64 on either side of the front 62 are parallel to each other and angled at an angle 66 with respect to the plane of the bottom surface 63 and bottom opening as can be clearly seen in FIGS. 3E-3F. The intersection of each landing surface 64 with the top surface 61 at the front 62 defines a notch 68. The notch 68 dips below the top surface of the front 62 such that the height of the cup 15 at the location of the notch 68 is less than the height of the front 62 from the bottom surface 63. The landing surfaces 64 serve as an abutment against the cup retainer 17 to stop and retain the movement of the cup 15 inside the plate 12. Furthermore, the outer surface of the cup 15 includes flat surfaces 67. The flat surfaces 67 are oppositely disposed and parallel to each other. The flat surfaces 67 are also located on either side in between the front 62 and back 60 of the cup 15. The cup 15 is configured to move, swivel, translate with respect to the plate 12 when inside the cup receiving portion 26. When located in the plate 12, the flat surfaces 67 are oriented and position such that they face the flat surfaces 27 in the cup receiving portion 26 in the plate 12. The flat surfaces 67 correspond and complement the flat surface 27 in the plate 12 to permit rotation relative to the plate 12 about an axis that generally intersects the center of both flat surfaces 27 in the plate 12.

Figure 11:
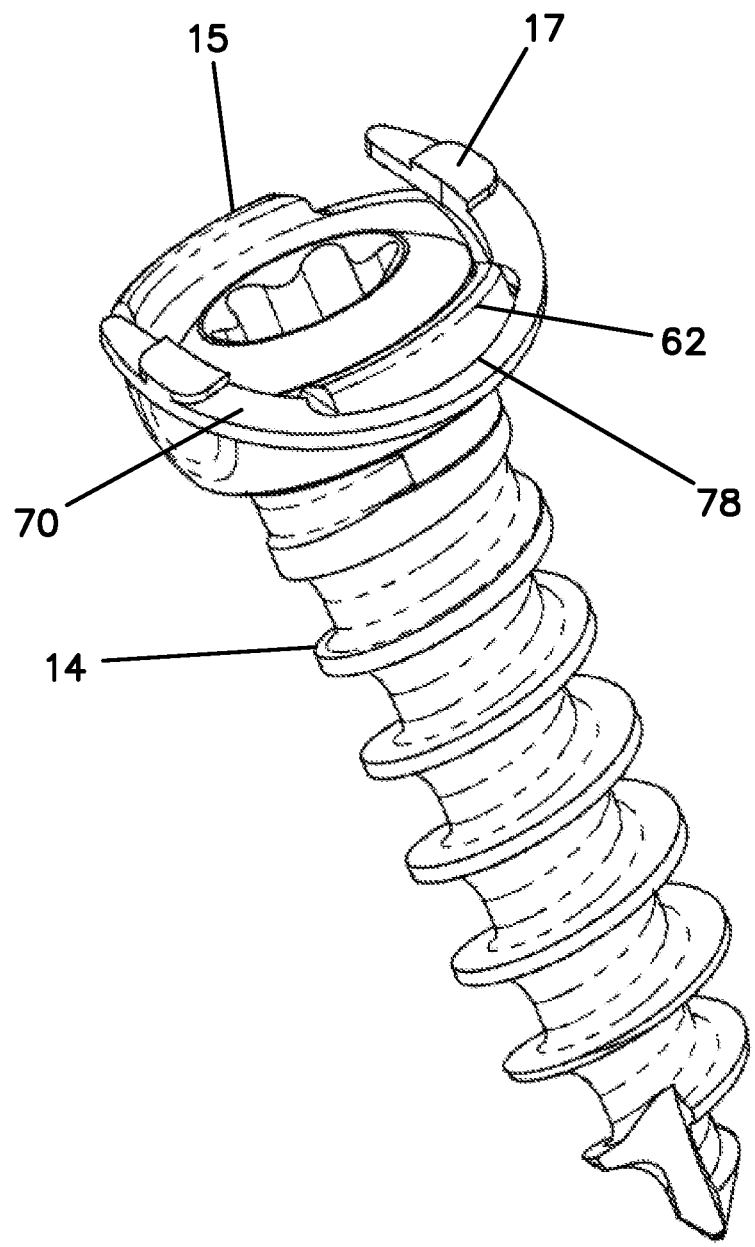
FIG. 11 is a top perspective view of two screws, cups and cup retainers according to the present invention.

Turning now to FIGS. 4A-4E, the cup retainer 17 will now be described. The cup retainer 17 is C-shaped or horseshoe-like in shape. The cup retainer 17 includes a top surface 70 and a bottom surface 72 defining a thickness therebetween and an inner surface an outer surface. The top surface 70 includes two protrusions 74 oppositely disposed from each other. The cup retainer 17 defines a closed end 76 or front of the cup retainer 17 that is substantially opposite from the open end of the C-shape. The inner surface of the cup retainer 17 includes a scallop 78 at the closed end 76. The scallop 78 is a reduced width location at the front 62 of the cup retainer 17 that permits the front 62 of cup retainer to pass through when the fastener 14 is angled forward as shown in FIG. 11. The cup retainer 17 is sized and configured to fit inside the groove 35 of the plate 12. Due to the open C-shape, the cup retainer 17 can flex in order to snap inside the groove 35 and be securely retained therein. The groove 35 prevents the cup retainer 17 from popping out of the plate 12. When located inside the groove 35 of the plate 12, at least a portion of the cup retainer 17 is covered by the cup retainer 17 located inside the channel-like groove 35. When assembled, the bottom surface 72 abuts the landing surface 64 and the closed end 76 loops around the front 62 of the cup 15. Assembly of the plate system 10 will be described in greater detail below.

Turning now to FIGS. 5A-5G, the lock 16 will now be described. The lock 16 includes a main body 48 connected to a post 50. The post 50 extends from the bottom surface 52 of the main body 48 along the longitudinal axis of the lock 16. The post 50 is configured to be inserted into the lock aperture 36 of the plate 12 and be connected to the plate 12 via the lock retainer 18 such that the lock 16 can rotate relative to the plate 12 about the longitudinal axis of the post 50. Whereas the post 50 is inserted into the plate 12, the main body 48 of the lock 16 resides above the upper surface 20 of the plate 12 in the location of the recess 34 next to a through hole 24 or in another variation as shown in the figures in the location of the recess 34 between two adjacent through holes 24 such that the main body 48 of the lock 16 does not substantially extend beyond the outer profile of the plate 12 maintaining the smooth low profile of the plate 12.

Still referencing FIGS. 5A-5G, the main body 48 of the lock 16 will now be described. The main body 48 includes a bottom surface 52 and a top surface 54. The top surface includes a socket 56 that is elongate in shape. The socket 56 is configured to receive an instrument such as a driver having a complementary shaped tip for engaging and rotating the lock 16 between an unlocked position and a locked position. The lock post 50 extends downwardly from the bottom surface 52 of the main body 48. The lock post 50 includes an outer surface configured for step-lock engagement with the lock retainer 18 which will be described in greater detail below. The top surface 54 and the bottom surface 52 of the main body 48 are interconnected by two locking ends 58 and two sides 59. The two locking ends 58 and the two sides 59 are opposite to each other and define an elongate, rectangular-like/elliptical-like shape when viewed from the top with the two sides 59 having a length that is greater than the length of each of the two locking ends 58. Although a rectangular or elongate shape is shown in the figures, the main body 48 can have any other suitable shape.

With continued reference to FIGS. 5A-5G, the lock post 50 includes an outer surface that forms two parallel, oppositely disposed end flats 80 and two parallel oppositely disposed side flats 82. The end flats 80 are perpendicular to the side flats 82. The flats 80, 82 are interconnected by curved surfaces 84. The flats 80, 82 and curved surfaces 84 extend along the length of the post 50. The distal end of the post 50 includes a circumferential flange 86. The flats 80, 82 are configured to engage the lock retainer 18 such that rotation of the lock 16 relative to the lock retainer 18 moves the lock 16 through a rotation of 90 degrees between adjacent flats wherein the intermediate curved surface 84 provides a smooth transition between the locked positions at the flats 80, 82 which will be described in greater detail below.

Turning now to FIGS. 6A-6E, the lock retainer 18 will now be described. The lock retainer 18 includes a cylindrical base 88 with two upwardly extending prongs 90 forming a Y-shape. Each prong 90 includes a flat surface 92 at the distal end of each prong 90. The flat surfaces 92 extend inwardly to form a hook-like configuration. The flat surfaces 92 are parallel to each other and parallel to and sized and configured to engage with the end flats 80 and side flats 82 on the lock post 50. The lock retainer 18 is sized and configured to be inserted from the lower surface 22 into the lock aperture 36 formed in the plate 12 and positioned such that the flat surfaces 92 of the lock retainer 18 engage the lock post 50. The lock 16 is prevented from falling out by abutment of the hook-like prongs 90 against the flange 86. When assembled, the Y-shaped prongs 90 flex slightly outwardly to permit rotation across the curved surfaces 84 between the flats 80, 82. When engaged with the end flats 80 and side flats 82, the flat surfaces 92 of the lock retainer 18 define unlocked and locked positions, respectively, for the lock 16. The locked and unlocked configurations will be described in greater detail below.

Figure 7A:
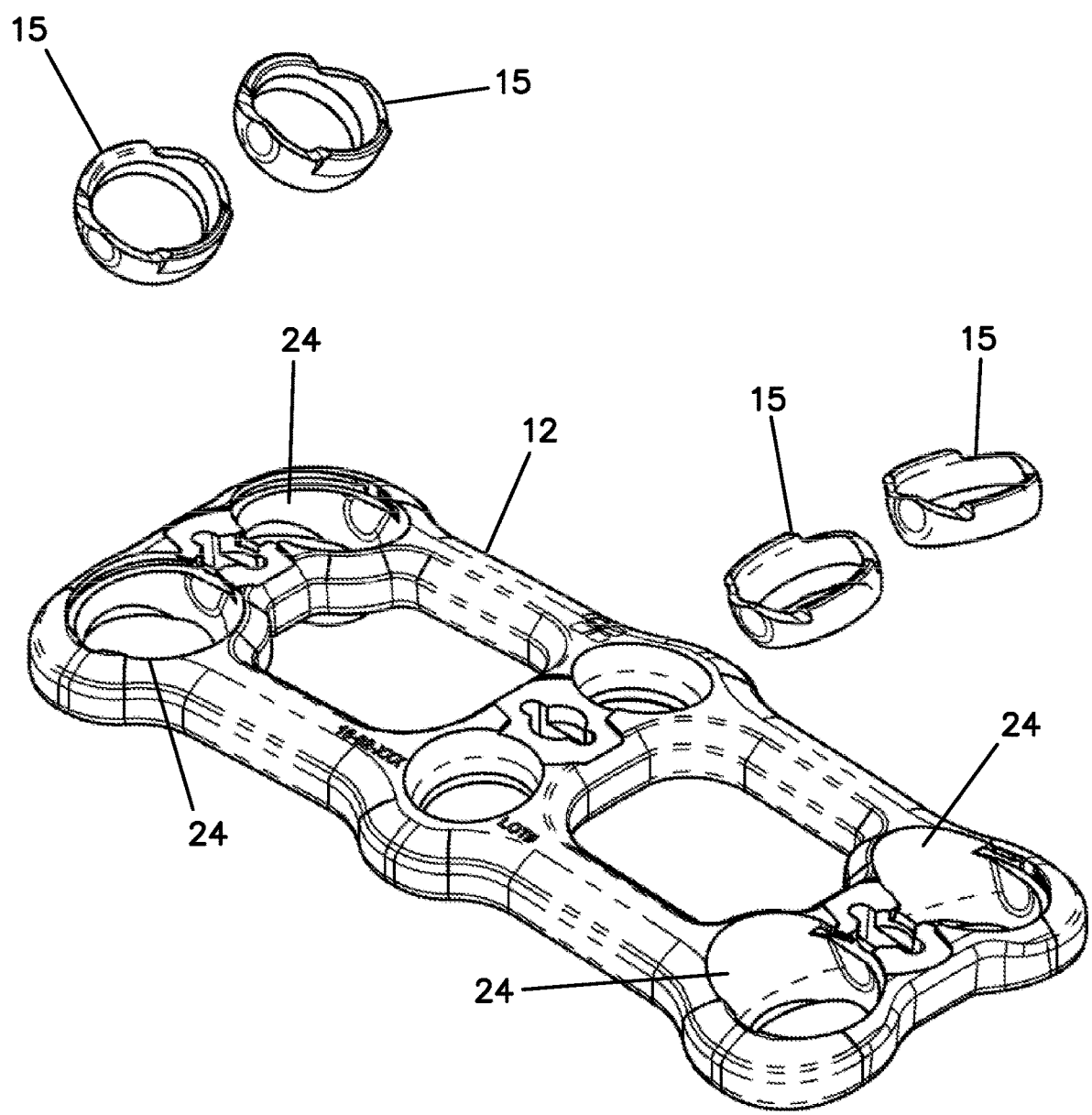
FIG. 7A is a top perspective, exploded view of a plate and cups according to the present invention.
Figure 7B:
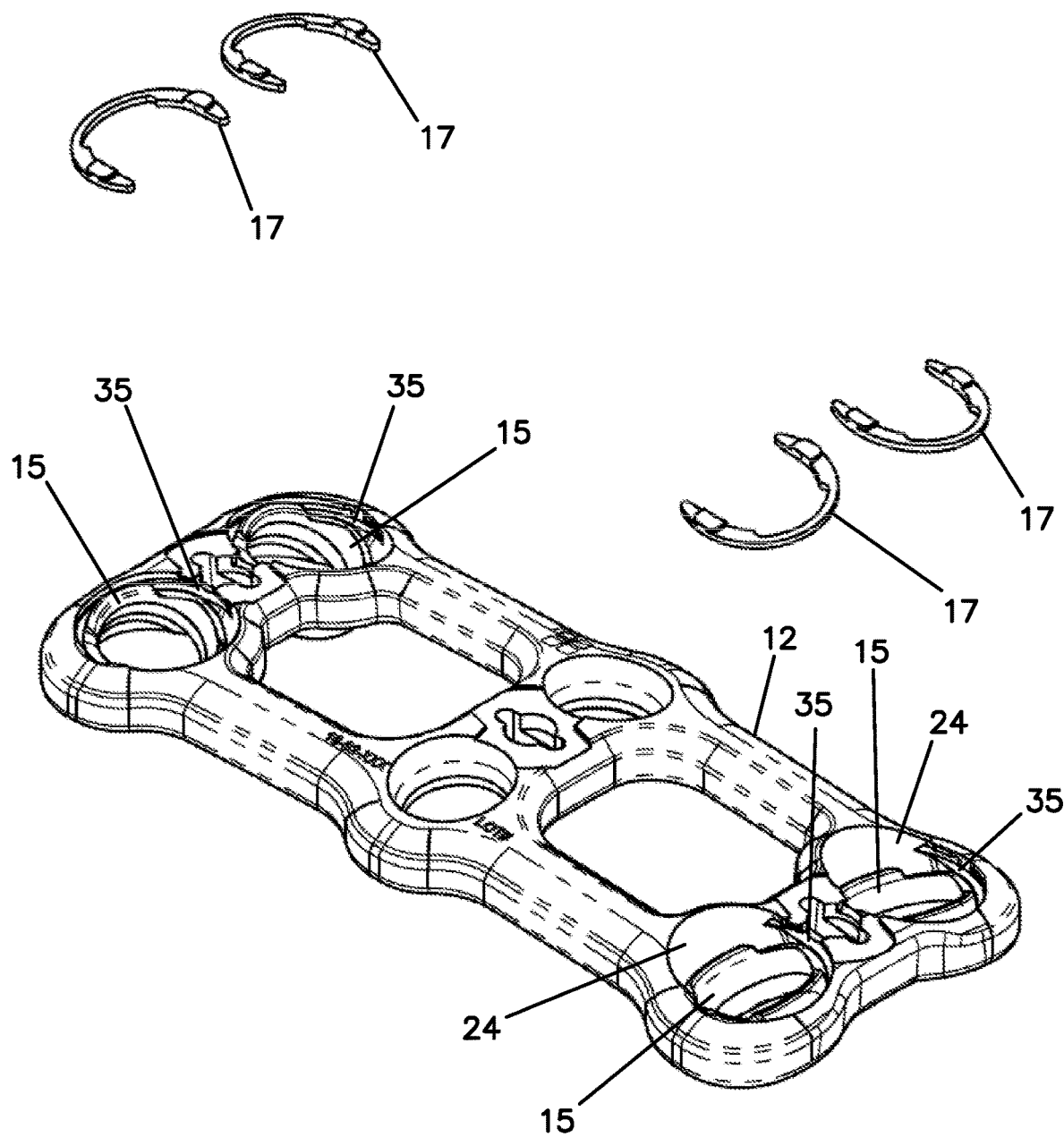
FIG. 7B is a top perspective, partially-exploded view of a plate, cups and cup retainers according to the present invention.
Figure 7C:
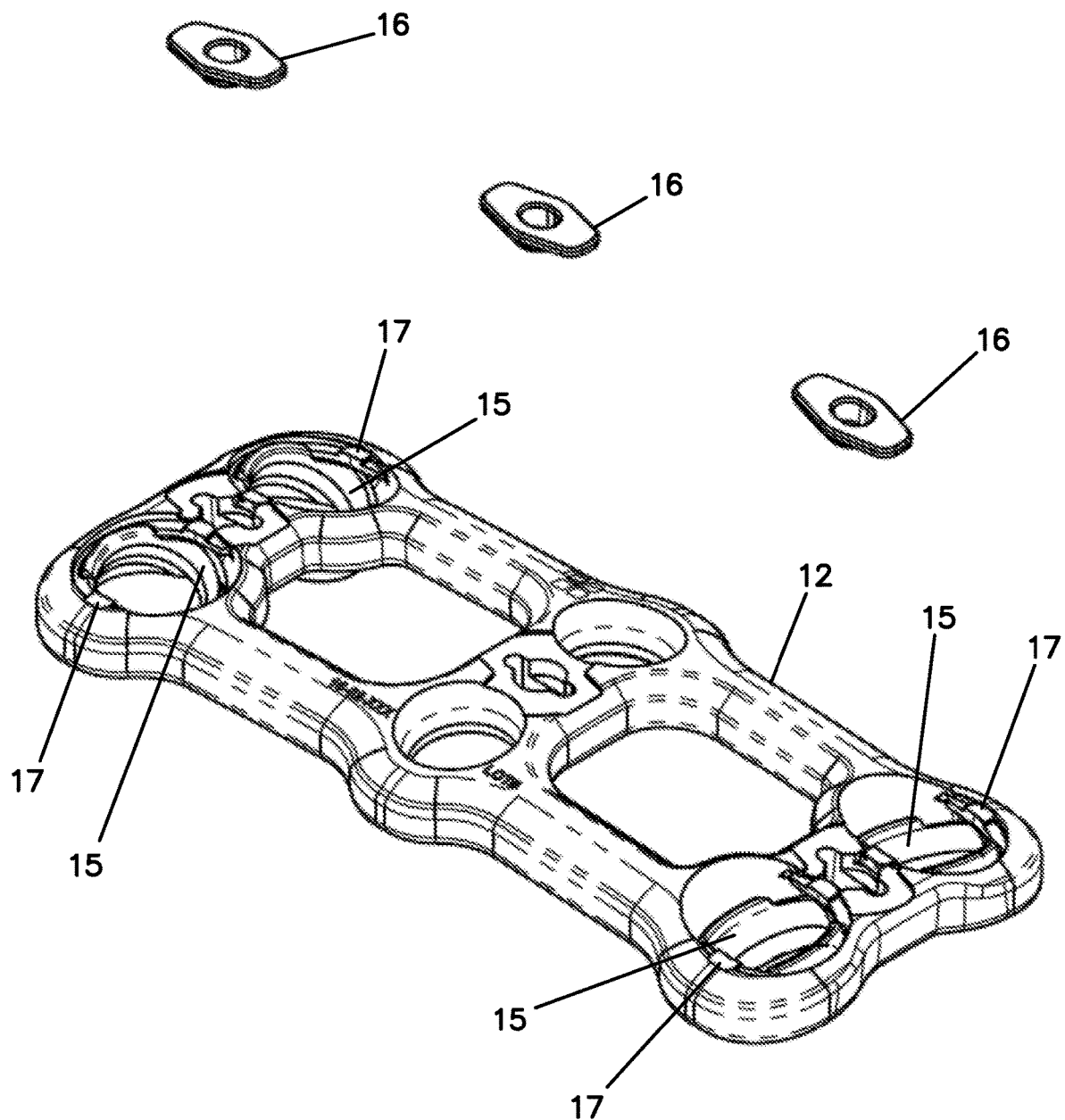
FIG. 7C is a top perspective, partially-exploded view of a plate, cups, cup retainers and locks according to the present invention.
Figure 7D:
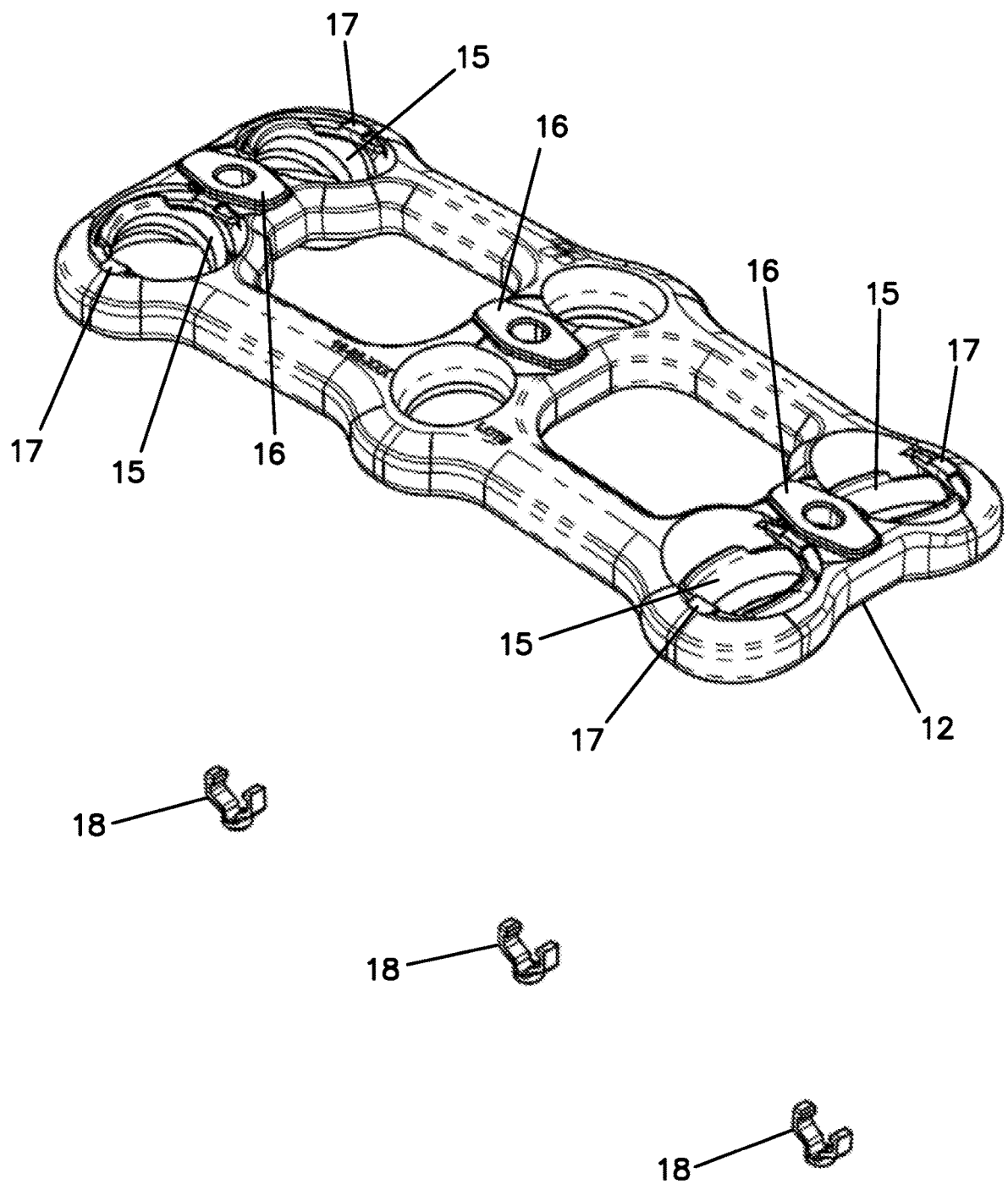
FIG. 7D is a top perspective, partially-exploded view of a plate, cups, cup retainers, locks and lock retainers according to the present invention.

Turning now to FIGS. 7A-7D, the assembly of the plate system 10 will be described. The cups 15 are inserted into the through holes 24 at the top and bottom ends of the plate 12 as shown in FIG. 7A. The cups 15 do not fall through the exit opening 30 in the lower surface 22 of the plate 12 because the cups 15 have a larger diameter near the top surface 61 relative to the bottom surface 63. The taper of the cup 15 can be seen in FIGS. 3D-3F. Also, the through hole 24 at the lower surface 22 has a smaller diameter relative to the diameter of the top of the cup 15. The cups 15 are oriented such that the front 62 faces away from and toward the ends of the plate 12 and the back 60 faces in toward the center of the plate 12. After the four cups 15 are positioned inside the through holes 24, the cup retainers 17 are snapped inside the grooves 35 of the plate 12 as shown in FIG. 7B. Each groove 35 is partially circumferential around the inner surface of the through hole 24 to correspond with the horseshoe-like shape. When snapped inside the groove 25, the cup 15 cannot be removed as it is retained inside the through hole 24 by the cup retainer 17. Yet, the cup 15 is permitted to angulate/pendulate/rotate forward and backward wherein the cup's 15 range of motion is limited by the cup retainer 17 and the plate 12. The flats 67 on the cup and flat surfaces 27 on the cup receiving portion 26 of the plate 12 are juxtaposition and prevent off-axis rotation of the cup 15 with respect to the plate 12 wherein the axis is centered across the flats on the cup and cup receiving portion. The scallop 78 in the cup retainer 17 allows passage of the front 62 of the cup 15 such that the landing surfaces 64 engage the bottom surface 72 of the cup retainer 17. With particular reference to FIG. 7C, with the four cup retainers 17 in position inside the plate 12, the lock 16 is inserted into the lock aperture 36 from the upper surface 20 of the plate 12. The lock 16 is oriented in an unlocked configuration and placed into the lock aperture 36. After the locks 16 are in position as shown in FIG. 7D, the lock retainers 18 are inserted into the lock aperture 36 from the lower surface 22 of the plate 12. As the lock retainer 18 is inserted, the prongs 90 will flex outwardly around the flange 86 on the lock post 50 and snap into position such that the lock retainers 18 are secured and do not fall out of the lock aperture 36. The lock retainer 18 cannot be removed proximally through the lock aperture 36 due to a ledge reducing the diameter of the lock aperture 36 at the bottom of the lock aperture 36 When assembled, the lock 16 is permitted to rotate with respect to the plate 12 and with respect to the stationary lock retainer 18.

Figure 8A:
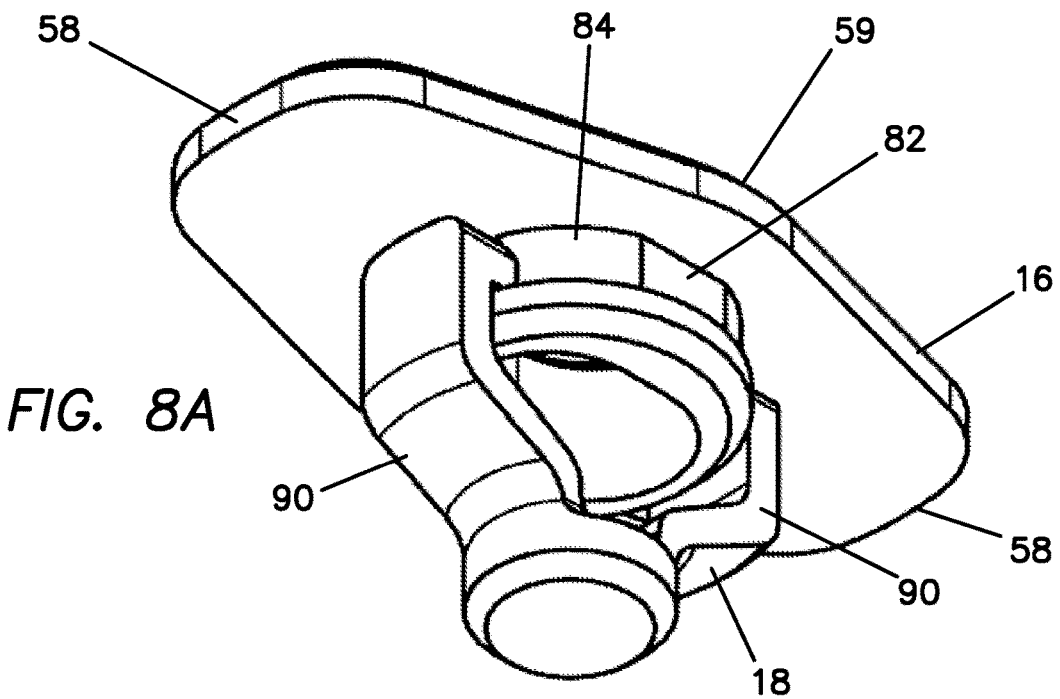
FIG. 8A is a bottom perspective view of a lock and lock retainer in an unlocked configuration according to the present invention.
Figure 8B:
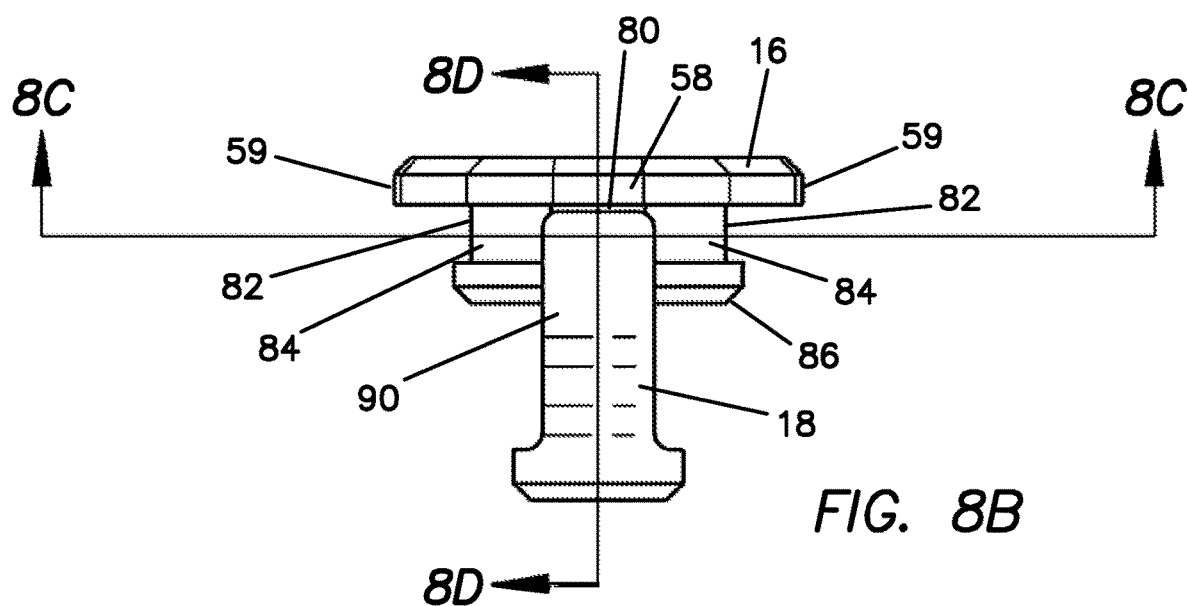
FIG. 8B is an end elevational view of a lock and lock retainer in an unlocked configuration according to the present invention.
Figure 8C:
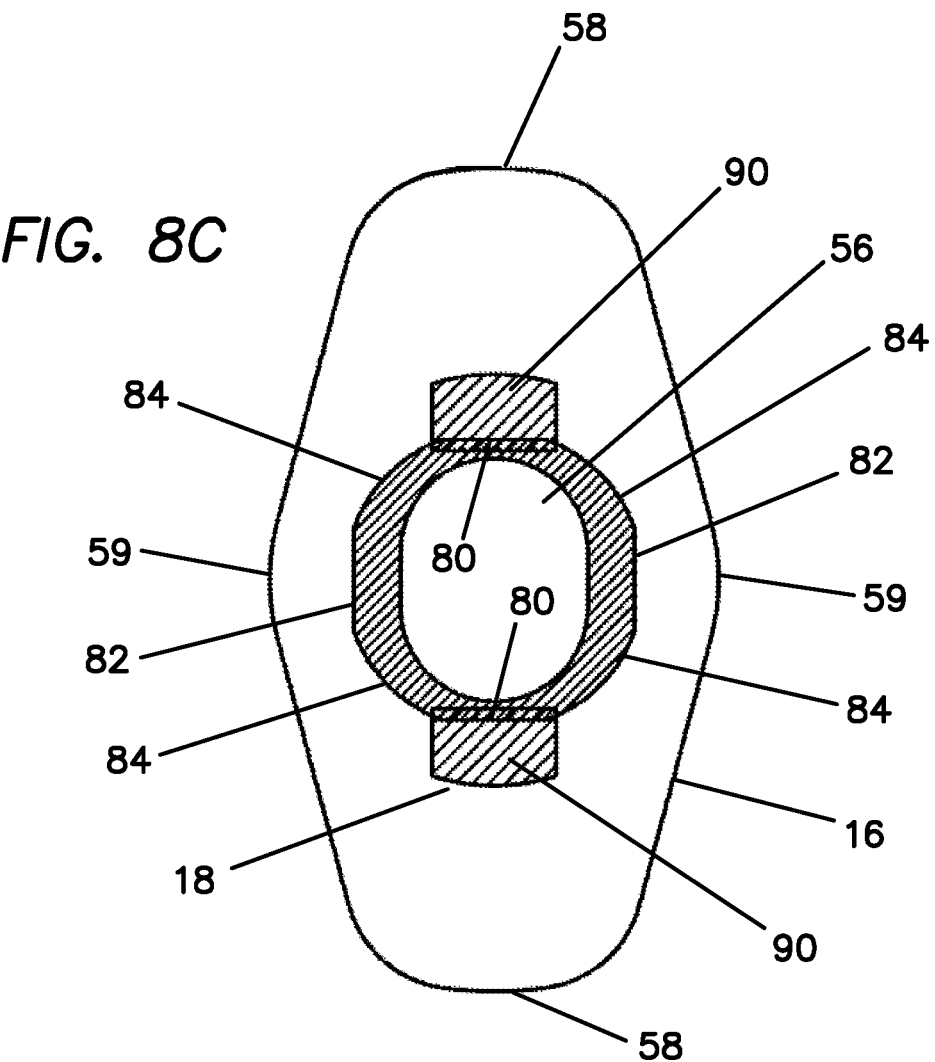
FIG. 8C is a cross-sectional view taken along line 8C-8C of FIG. 8B of a lock and lock retainer in an unlocked configuration according to the present invention.
Figure 8D:
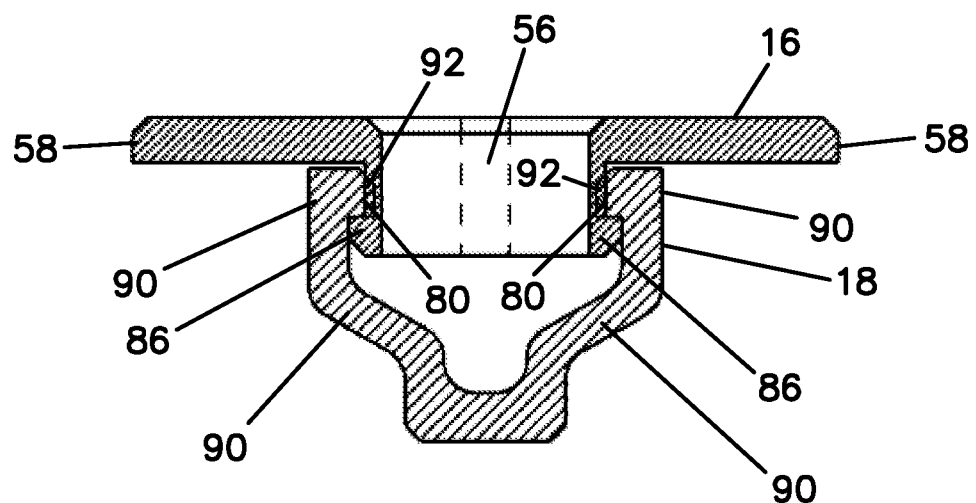
FIG. 8D is a cross-sectional view taken along line 8D-8D of FIG. 8B of a lock and lock retainer in an unlocked configuration according to the present invention.
Figure 9A:
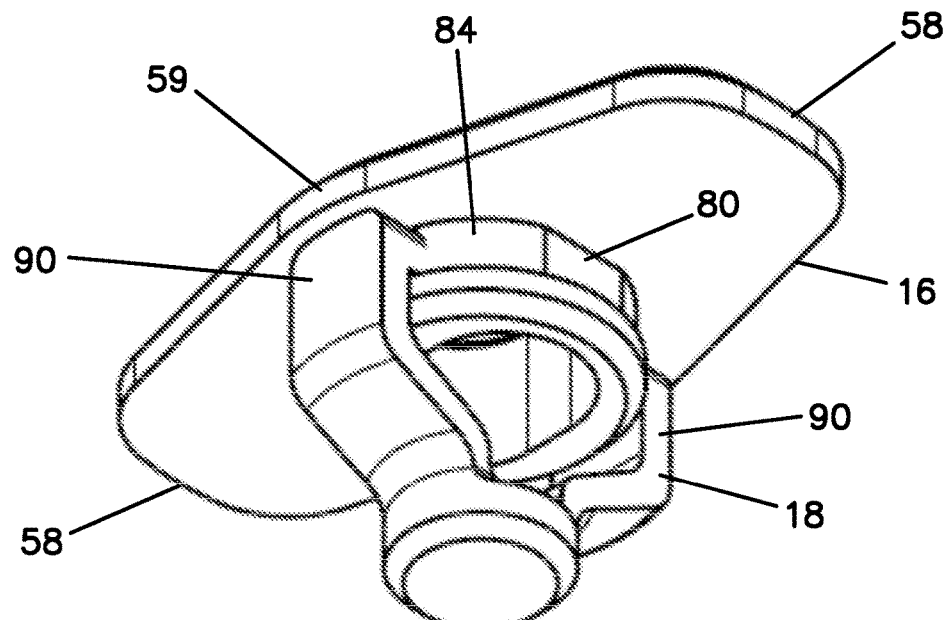
FIG. 9A is a bottom perspective view of a lock and lock retainer in a locked configuration according to the present invention.
Figure 9B:
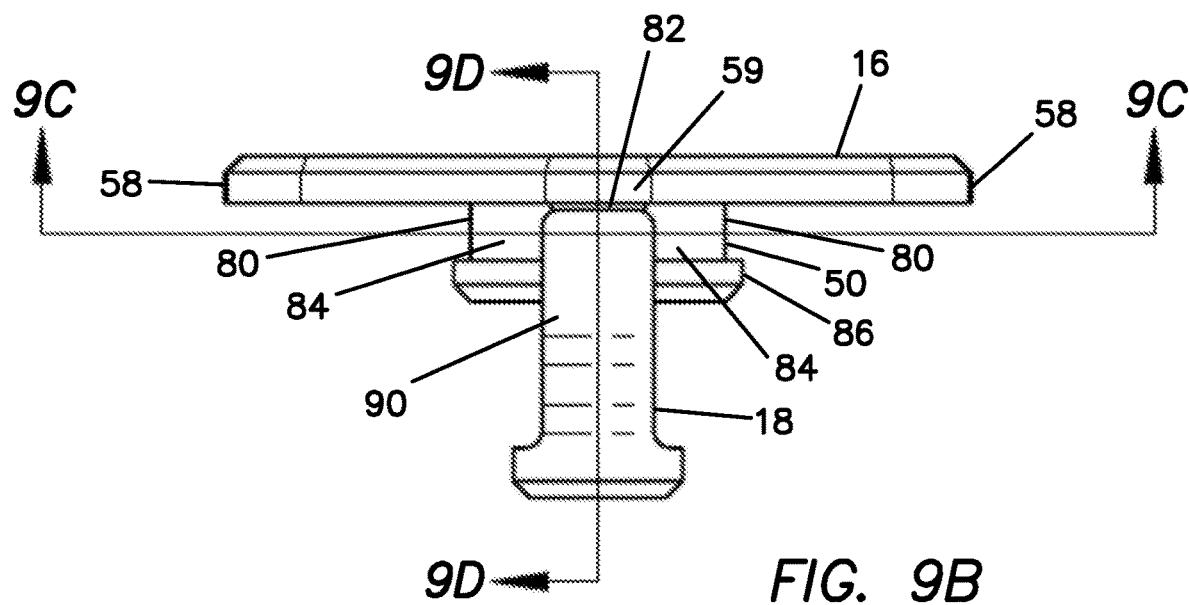
FIG. 9B is a side elevational view of a lock and lock retainer in a locked configuration according to the present invention.
Figure 9C:
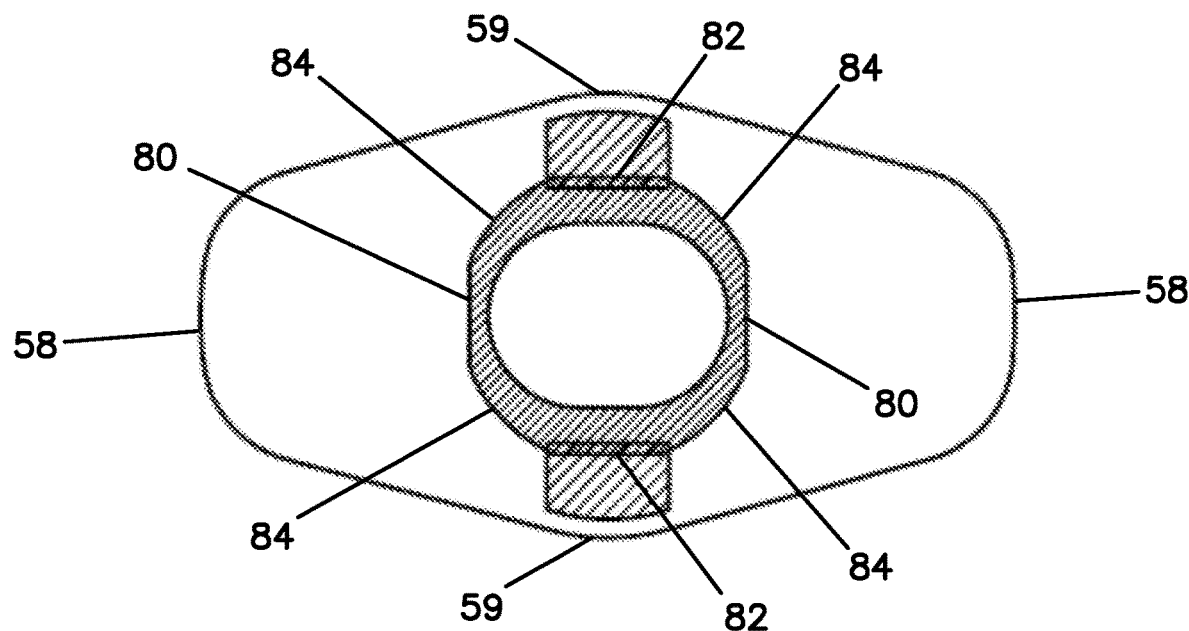
FIG. 9C is a cross-sectional view taken along line 9C-9C of FIG. 9B of a lock and lock retainer according to the present invention.
Figure 9D:
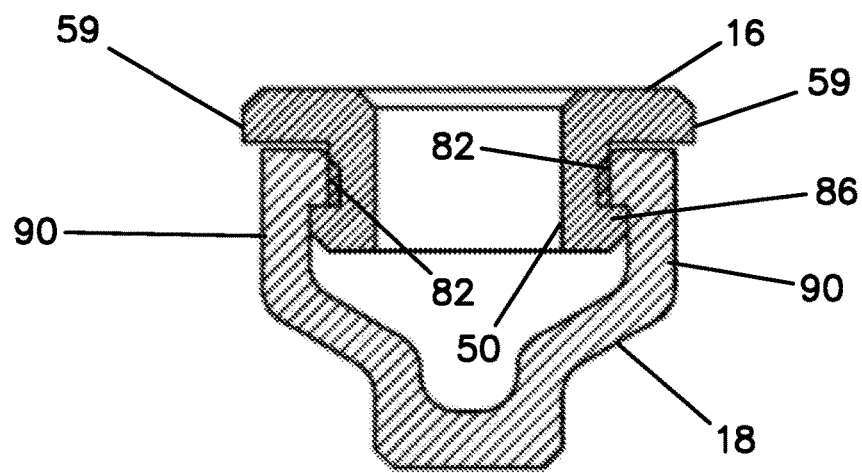
FIG. 9D is a cross-sectional view taken along line 9D-9D of FIG. 9B of a lock and lock retainer according to the present invention.

Turning now to FIGS. 8A-8D, the unlocked configuration between the lock 16 and lock retainer 18 are shown. When in an unlocked configuration, the lock 16 is rotated away from the through hole 24 such that the through hole is not blocked by the lock 16 and a fastener 14 may be inserted and removed into the plate. When the lock 16 is disposed between two through holes 24, both through holes 24 are simultaneously uncovered in the unlocked configuration. When in the unlocked configuration, the flat surfaces 92 on the lock retainer 18 contact the oppositely disposed end flats 80 on the lock post 50. As can be seen in FIG. 8D, the flange 86 on the lock post 50 is hooked underneath the flat surfaces 92 of the prongs 90, thereby, preventing the lock 16 from separating from the lock retainer 18. The lock 16 is rotatable relative to the plate 12 and relative to the lock retainer 18 between the unlocked configuration and the locked configuration. When in the locked configuration, the lock 16 is rotated to cover the through holes between the lock 16 and the lock retainer 18 such that the through holes 24 are blocked by the lock 16. In particular, the bottom surface 52 of the lock 16 covers the through holes 24 such that back-out protection is provided for fasteners 14 inserted into the plate 12. In particular, the lock 16 covers the top of the fastener 14 such that a loosened fastener will abut the lock 16 and advantageously remain implanted in the patient. The locked configuration is depicted in FIGS. 9A-9D. When in the locked configuration, the flat surfaces 92 on the lock retainer 18 contact the oppositely disposed side flats 82 on the lock post 50. When moving from the unlocked position to the locked position, the prongs 90 flex slightly outwardly to ride over the oppositely disposed curved surfaces 84 on the lock post 50. After a rotation of 90 degrees, the prongs 90 will land on the side flats 82. The lock 16 is rotated by use of an instrument inserted into the socket 56 at the top surface 54 of the lock 16. The lock 16 is rotatable clockwise or counterclockwise to and from the locked and unlocked positions. From the locked position, the lock 16 is rotatable clockwise or counterclockwise to the unlocked position as desired. When moving from the locked position to the unlocked position, the prongs 90 again flex slightly outwardly to ride over the oppositely disposed curved surface 84 on the lock post 50 simultaneously. The diameter of the lock post 50 in the location of the curved surfaces 84 is slightly greater than the distance between oppositely disposed end flats 80 and side flats 84. After a rotation of 90 degrees, the prongs 90 land on the end flats 82 and the plate 12 is unlocked and the fasteners are free to move proximally outwardly from the plate 12 or adjust and driven distally into the vertebral bone. The lock 16 need not rotate a full 90 degrees to effect a locked configuration and a rotation of less than 90 degrees may still be effective in preventing the fastener 14 from backing out in difficult conditions due to variances in anatomy. The transition from the prongs 90 being in contact with the curved surfaces 84 to being in contact with the flat surfaces 80 or 82 advantageously provides a tactile feedback to the user as the prongs 90 snap in position against the flats 80 or 82.

Figure 10:
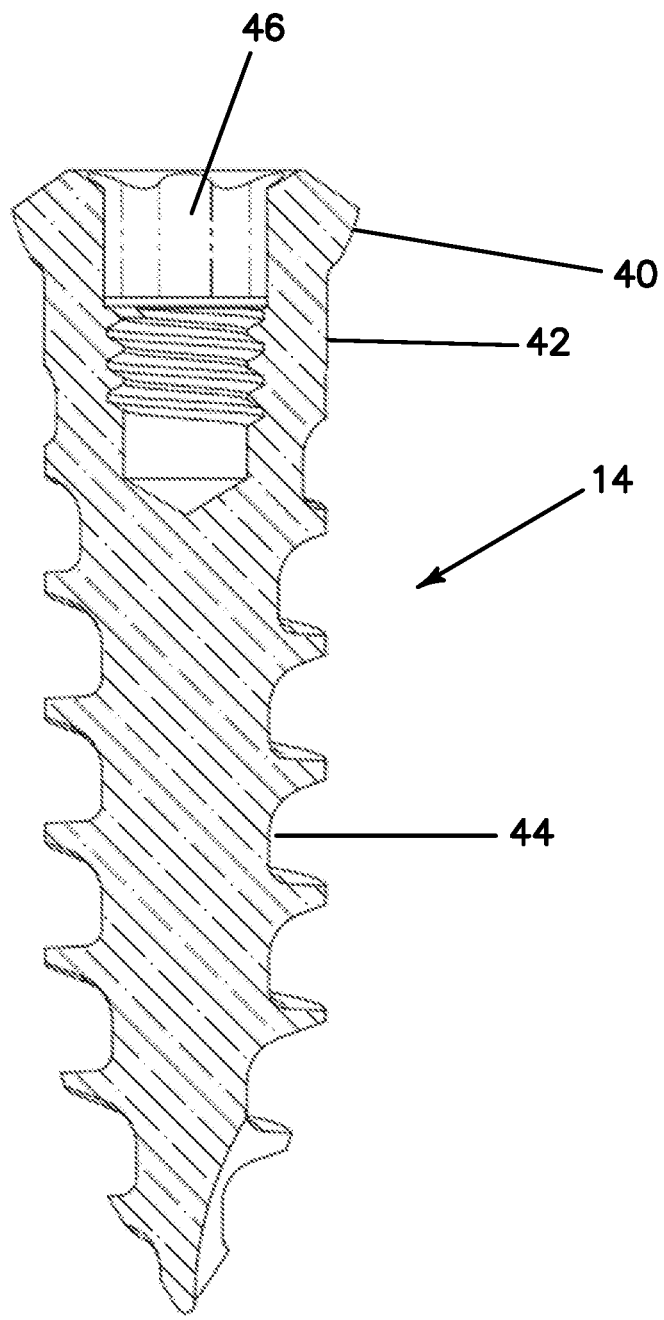
FIG. 10 is a cross-sectional view of a screw according to the present invention.

Turning now to FIG. 10, an exemplary orthopedic fastener 14 that is preferably used with the cervical plate system 10 of the present invention is a bone screw 14. The bone screw 14 includes a screw head 40, neck 42 and threaded shank 44. The head 40 includes an instrument recess 46 for receiving a complementary tip of a surgical tool. The instrument recess 46 allows a surgical tool to drive the bone screws 14 into the vertebral column. In one variation, the instrument recess 46 includes a distal threaded section for threadingly engaging the instrument for insertion and/or removal of a fastener 14. The head 40 of the bone screw 14 corresponds to the shape of the interior of the cup 15. Various bone screws 14 may be employed including ones capable of poly-axial, variable angle or fixed angled orientation with respect to the plate 12 with or without the ability to be locked down at a desired angle or orientation with respect to the plate 12. The bone screws 14 are preferably self-tapping, however, other screws requiring holes to be drilled or pre-tapped can also be employed.

In use, the anterior cervical plate 12 according to the present invention is placed or attached adjacent to a vertebral column. The placement of the plate 12 relative to the vertebral bone in a patient may be pre-operatively determined based on a pre-operative examination of the patient's spine using non-invasive imaging techniques known in the art. Any additional preparation or work may be done on and around the desired vertebrae prior to positioning the plate 12. Once the plate 12 is appropriately positioned, it may be necessary to keep the plate 12 in the desired position while inserting fasteners 14. Setting pins may be employed to assist in keeping the plate 12 in position against the bone. Next, bone fasteners 14 are inserted into through holes 24 of the plate 12 while the lock 16 is in an unlocked position. To insert a bone fastener 14, an instrument is inserted into the instrument recess 46 of the fastener 14 and the fastener 14 is driven or screwed into the desired bone location. FIG. 11 illustrates an isolated view of a fastener 14, cup 15 and cup retainer 17. As can be seen in FIG. 11, the scallop 78 in the cup retainer 17 allows the front 62 of the cup 15 to protrude above the top surface 70 of the cup retainer 16 when the fastener 14 is angulated. The unlocked configuration of the plate 12 is depicted in FIGS. 12A-12J. Once the fasteners 14 are correctly positioned in the through holes 24, the lock 16 is rotated from the unlocked configuration towards the locked configuration. To rotate the lock 16, an instrument is inserted into the socket 56 and the lock 16 is rotated from an unlocked position. As the lock 16 is rotated, the flat surfaces 92 of the lock retainer 18 move from contact with the end flats 80 over the curved surfaces 84 and into contact with the side flats 82 in the locked configuration covering the screw heads 40 of the inserted fasteners 14. The screw heads 40 of adjacent fasteners 14 are covered simultaneously by one lock 16 as shown in FIGS. 13A-13I. When any portion of the bottom surface 52 of the lock 16 covers the screw head 40 at least partially, back-out protection is achieved and a locked condition is effected. The surgeon may choose to continue with the rotation of the lock 16 such that a greater portion of the screw head 40 is covered by the lock 16. However, this is not necessary and sometimes anatomically not possible because positioning of the fastener 14 may result in the fastener 14 being angled with respect to the upper surface of the plate 12 such that a portion of the screw head 40 projects above the plate; however, due to the ability of the plate system 10 of the present invention to accommodate extreme angles, this situation is advantageously alleviated in a greater number of cases making it less likely that a partial locking orientation or more likely that a full locking orientation of the lock is achieved. It is up to the surgeon's discretion to determine if the lock 16 is adequately positioned to prevent the backing out of the fasteners 14 and is more easily achievable with the plate system 10. In some circumstances, the surgeon may opt to move the lock into an unlocked configuration and further drive the bone screw deeper into the bone such that the screw head 40 is more recessed and then rotate the lock back into the locked position. The locked condition prevents the bone screw 14 from loosening before migrating back out of the through hole 24 and keeps the bone screw 14 inside the through hole 24. When all of the fasteners 14 are inserted and in position, the setting pins are removed and all of the locks 16 are turned to their locked conditions and the surgical procedure is finalized.

Figure 14A:
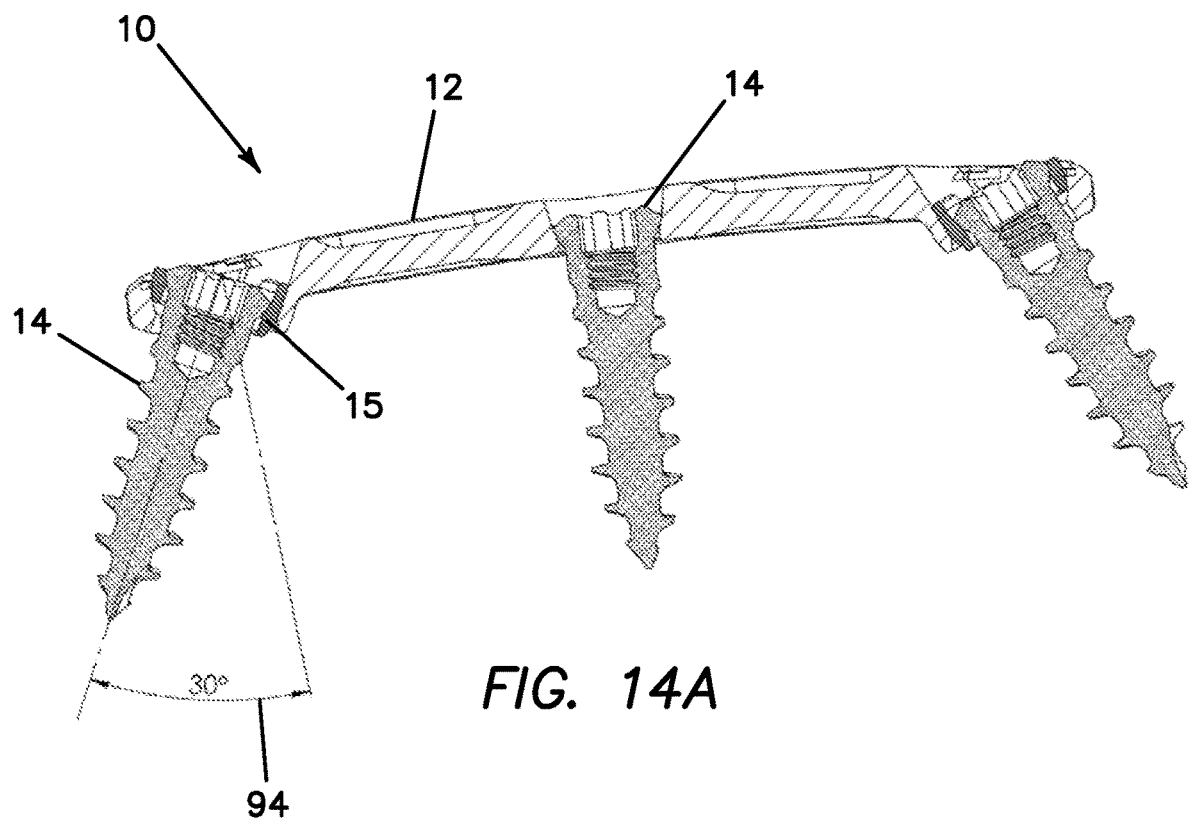
FIG. 14A is a cross-sectional view of the plate system according to the present invention.
Figure 14B:
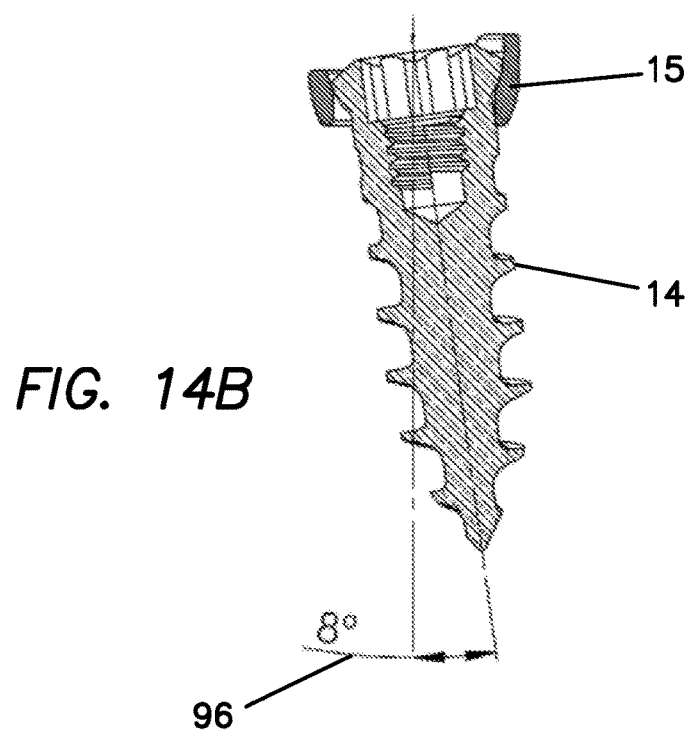
FIG. 14B is a cross-sectional view of a fastener inside a cup according to the present invention.

Turning now to FIGS. 14A and 14B, there is shown a plate system 10 according to present invention. In FIG. 14A, the cup 15 is shown angulated with respect to the plate 12 in a direction forwards such that the fasteners are pointing away from the plate 12. In FIG. 14A, the maximum angulation of the cup 15 with respect to the fastener 14 is 30 degrees. In FIG. 14B, the maximum angulation of the fastener 14 with respect to the cup 15 is 8 degrees. The fastener 14 has a conical angulation of 16 degrees with respect to cup 15. This combination of angulation of the cup 15 with respect to the plate 12 and the fastener 14 with respect to the cup 15 is 38 degrees.

Figure 15A:
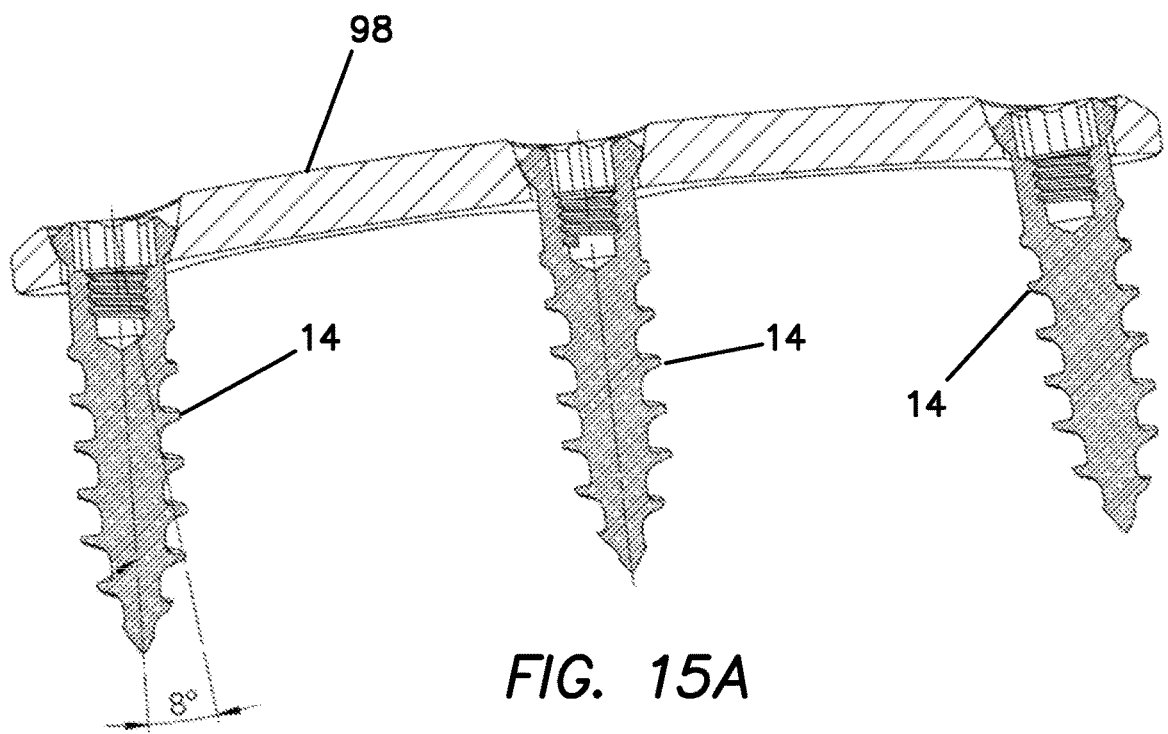
FIG. 15A is a cross-sectional view of a plate system.
Figure 15B:
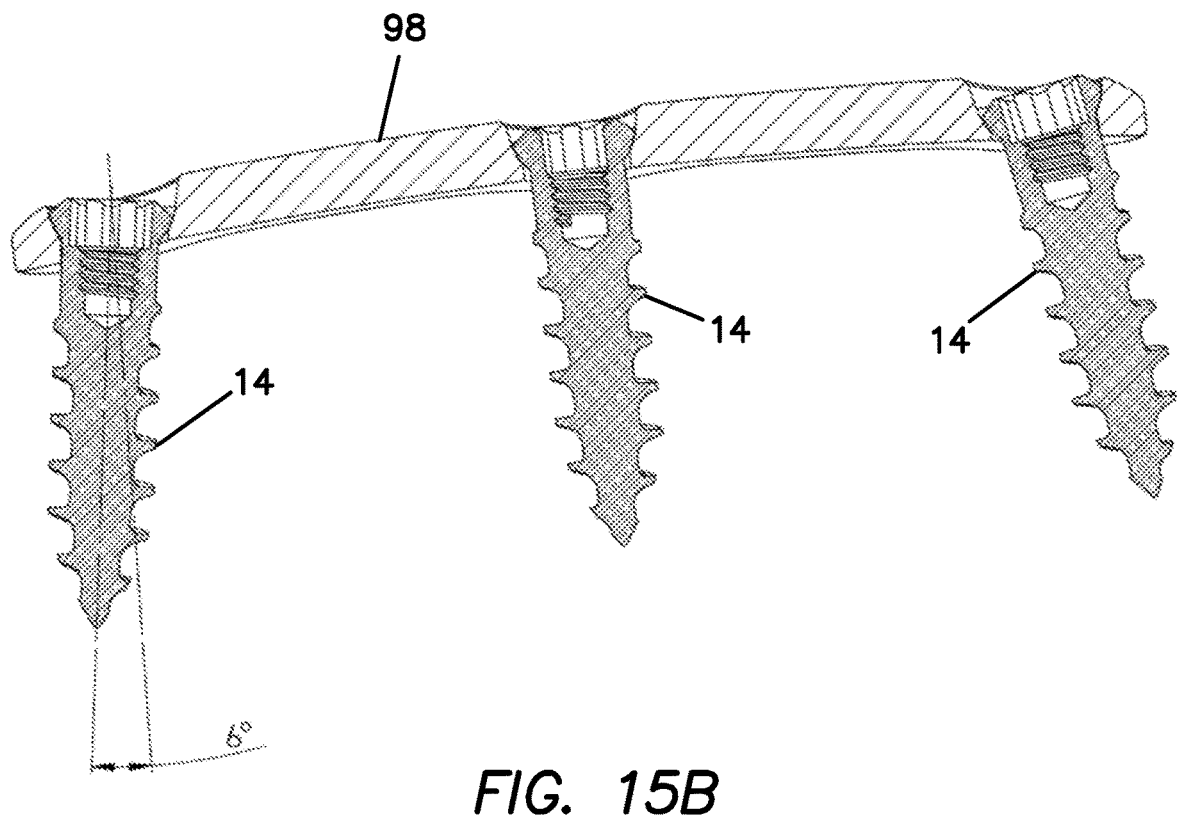
FIG. 15B is a cross-sectional view of a plate system.

In contrast, in a conventional plate system such as the one depicted in FIGS. 15A-15B produced by NeuroStructures, Inc. in Irvine, Calif., the maximum angulation of the fastener 14 with respect to the plate 98 is 8 degrees in the backward direction such that the fasteners 14 are pointing toward the plate 12. The maximum angulation in the forward direction is 6 degrees. Hence, the maximum angulation of the plate system 10 according to the present invention is significantly larger than a conventional plate 98. The configuration of the present invention advantageously provides a full 38 degrees of maximum angulation in the forward and 38 degrees in the backward directions. The plates 12, 98 in FIGS. 14-15 are 35 millimeter plates.

To remove the bone plate 12 from a patient, the same instrument is used to rotate the locks 16 from the locked position to the unlocked configuration in which the locks 16 are not adjacent or covering the fasteners 14. Then an instrument can be inserted into the instrument recess 46 on the screw head 40 to remove the bone screws 14. The instrument is used to back out the screw 14.

The anterior cervical plate system 10 of the present invention provides several advantages over previous designs. For example, if the patient's anatomy requires a highly-angled placement of the bone fastener, the present invention permits such placement of the fastener and still allows the back-out protection to be employed by the user. The present invention sets forth a novel plate system with a number of advantages that include a lower profile and less impingement on surrounding tissue, a locking condition that can be effected more easily and in greater anatomical conditions.

Although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above.

We claim:

1. A bone plate system, comprising:
    a plate having at least one through hole configured to receive a bone screw; the plate having an upper surface and a lower surface interconnected by side surfaces; the plate includes a lock aperture adjacent to the at least one through hole; two oppositely disposed flat surfaces formed inside the at least one through hole; the plate including a groove formed at the at least one through hole;
    a bone screw having a head portion connected to a shank portion; the bone screw being sized and configured for insertion into the through hole;
    a lock retainer located inside the lock aperture;
    a lock having a main body connected to a lock post; the lock being connected to the plate by the lock retainer such that the lock is permitted to rotate with respect to the plate between an unlocked position in which the main body of the lock does not cover the head of the bone screw inside the through hole permitting passage of the bone screw in or out of the through hole and a locked position in which at least part of the main body is above the head portion of the bone screw to prevent the bone screw from backing out of the through hole;
    a cup located inside the at least one through hole; the cup having an inner surface and an outer surface; the inner surface defining a lumen sized and configured to receive at least a portion of the bone screw; the outer surface of the cup including two oppositely disposed flat surfaces; and
    a cup retainer located inside the groove; the cup retainer being sized and configured to retain the cup inside the at least one through hole;
    wherein the cup is retained inside the at least one through hole such that the flat surfaces of the cup face the flat surfaces inside the through hole and the cup is movable with respect to the plate.

2. The bone plate system of claim 1 wherein the plate includes an extending portion depending from the lower surface of the plate.

3. The bone plate system of claim 1 wherein the upper surface of the plate includes at least two stops configured to limit rotation of the lock between the at least two stops.

4. The bone plate system of claim 3 wherein the lock is positioned between the two stops and rotatable 90 degrees in either direction between the two stops.

5. The bone plate system of claim 1 wherein the plate includes a recess surrounding the lock aperture and configured to recess the main body of the lock.

6. The bone plate system of claim 1 wherein the cup retainer includes a scallop configured to provide clearance for the cup.

7. A bone plate system, comprising:
    a plate having at least one through hole configured to receive a bone screw; the plate having an upper surface and a lower surface interconnected by side surfaces and a longitudinal axis;
    a bone screw having a head portion connected to a shank portion; and
    a cup located inside at least one through hole; the cup having an inner surface and an outer surface; the inner surface defining a lumen sized and configured to receive at least a portion of the bone screw;
    wherein the cup is connected to the plate such that the cup is retained and permitted to angulate with respect to the plate; and
    wherein the bone screw is connected to the plate such that the head portion of the bone screw is located inside the cup and the bone screw is permitted to angulate with respect to the cup.

8. The bone plate system of claim 7 further including two oppositely disposed flat surfaces formed inside the at least one through hole and two oppositely disposed flat surfaces formed on the outer surface of the cup; wherein the cup is located inside the through hole such that the flat surfaces on the cup face the flat surfaces inside the through hole.

9. The bone plate system of claim 8 wherein the center of the flat surfaces inside the through hole define an axis of angulation about which the cup is permitted to rotate relative to the plate.

10. The bone plate system of claim 8 wherein the axis of angulation is perpendicular to the longitudinal axis of the plate.

11. The bone plate system of claim 7 wherein the bone screw angulates polyaxially with respect to the cup defining a conical range of motion.

12. The bone plate system of claim 11 wherein the conical range of motion is approximately 14-18 degrees.

13. The bone plate system of claim 7 wherein the cup angulates approximately 25-35 degrees forward and approximately 25-35 degrees backward with respect to the plate.

14. The bone plate system of claim 7 wherein the plate includes an extending portion at the lower surface of the plate in the location of the at least one through hole; the extending portion extending downwardly from the lower surface of the plate.

15. The bone plate system of claim 14 wherein at least a portion of the cup is located inside the at least one through hole and is located below the lower surface of the plate.

16. The bone plate system of claim 7 wherein the plate includes a groove formed near the upper surface of the plate in the location of the at least one through hole;
and further including a cup retainer located inside the groove; the cup retainer being sized and configured to retain the cup inside the at least one through hole.

17. A bone plate system, comprising:
a plate having at least one through hole configured to receive a bone screw; the plate having an upper surface and a lower surface interconnected by side surfaces and a longitudinal axis; and a groove formed near the upper surface of the plate in the location of the at least one through hole;
a bone screw having a head portion connected to a shank portion; and
a cup located inside at least one through hole; the cup having an inner surface and an outer surface interconnected by a top surface and a bottom surface; the inner surface defining a lumen sized and configured to receive at least a portion of the bone screw; the cup having a shorter front relative to a longer back; and
a cup retainer located inside the groove; the cup retainer being sized and configured to retain the cup inside the at least one through hole such that the cup is permitted to angulate with respect to the plate; the cup retainer includes a scallop sized and configured to permit angulation of the back of the cup through the scallop; and
wherein the bone screw is connected to plate such that the bone screw is permitted to angulate with respect to the cup.

18. The bone plate system of claim 17 further including a lock movable with respect to the plate between an unlocked position in which the lock does not cover the head of the bone screw permitting passage of the bone screw in or out of the through hole and a locked position in which the lock is above the head portion of the bone screw to prevent the bone screw from backing out of the through hole.

19. The bone plate system of claim 17 wherein at least a portion of the top surface of the cup is angled with respect to the bottom surface of the cup.

20. The bone plate system of claim 17 wherein the cup is permitted to angulate only about an axis perpendicular to the longitudinal axis of the plate.

\* \* \* \* \*